United States Patent
Ma et al.

(10) Patent No.: US 10,500,577 B2
(45) Date of Patent: Dec. 10, 2019

(54) OXALIC AMIDE LIGANDS, AND USES THEREOF IN COPPER-CATALYZED COUPLING REACTION OF ARYL HALIDES

(71) Applicant: CE Pharm CO., LTD, Taizhou (CN)

(72) Inventors: Dawei Ma, Shanghai (CN); Wei Zhou, Shanghai (CN); Mengyang Fan, Shanghai (CN); Haibo Wu, Shanghai (CN); Junli Yin, Shanghai (CN); Shanghua Xia, Shanghai (CN)

(73) Assignee: CE Pharm CO., LTD, Taizhou (CN)

( * ) Notice: Subject to any disclaimer, the term of this patent is extended or adjusted under 35 U.S.C. 154(b) by 0 days.

(21) Appl. No.: 15/746,646

(22) PCT Filed: Apr. 15, 2016

(86) PCT No.: PCT/CN2016/079500
§ 371 (c)(1),
(2) Date: Jan. 22, 2018

(87) PCT Pub. No.: WO2017/012379
PCT Pub. Date: Jan. 26, 2017

(65) Prior Publication Data
US 2018/0207628 A1    Jul. 26, 2018

(30) Foreign Application Priority Data
Jul. 20, 2015 (CN) .......................... 2015 1 0428566

(51) Int. Cl.
*C07D 207/325* (2006.01)
*B01J 31/22* (2006.01)
(Continued)

(52) U.S. Cl.
CPC ........... *B01J 31/2243* (2013.01); *B01J 31/22* (2013.01); *C07B 41/02* (2013.01); *C07B 43/04* (2013.01); *C07B 45/06* (2013.01); *C07C 41/26* (2013.01); *C07C 45/64* (2013.01); *C07C 209/08* (2013.01); *C07C 209/10* (2013.01); *C07C 213/02* (2013.01); *C07C 213/08* (2013.01); *C07C 221/00* (2013.01); *C07C 231/02* (2013.01); *C07C 231/12* (2013.01); *C07C 231/14* (2013.01); *C07C 233/56* (2013.01); *C07C 253/30* (2013.01); *C07C 315/04* (2013.01); *C07C 319/14* (2013.01); *C07C 319/20* (2013.01); *C07D 207/06* (2013.01); *C07D 207/14* (2013.01); *C07D 207/27* (2013.01); *C07D 207/325* (2013.01); *C07D 207/335* (2013.01); *C07D 209/08* (2013.01); *C07D 209/86* (2013.01); *C07D 211/72* (2013.01); *C07D 213/40* (2013.01); *C07D 213/65* (2013.01); *C07D 213/73* (2013.01); *C07D 213/74* (2013.01); *C07D 213/89* (2013.01); *C07D 215/20* (2013.01); *C07D 215/38* (2013.01); *C07D 215/40* (2013.01); *C07D 217/22* (2013.01); *C07D 223/12* (2013.01); *C07D 223/22* (2013.01); *C07D 231/12* (2013.01); *C07D 233/60* (2013.01); *C07D 239/42* (2013.01); *C07D 239/545* (2013.01); *C07D 241/18* (2013.01); *C07D 241/20* (2013.01); *C07D 241/42* (2013.01); *C07D 263/56* (2013.01); *C07D 277/64* (2013.01); *C07D 277/66* (2013.01); *C07D 295/00* (2013.01); *C07D 295/096* (2013.01); *C07D 295/135* (2013.01); *C07D 307/22* (2013.01); *C07D 307/52* (2013.01); *C07D 307/81* (2013.01); *C07D 317/28* (2013.01); *C07D 317/58* (2013.01); *C07D 317/64* (2013.01); *C07D 317/66* (2013.01); *C07D 333/20* (2013.01); *C07D 333/36* (2013.01); *C07D 333/54* (2013.01); *C07D 333/58* (2013.01);
(Continued)

(58) Field of Classification Search
CPC ..................................................... B01J 31/2243
See application file for complete search history.

(56) References Cited

FOREIGN PATENT DOCUMENTS

CN    102159534 A    8/2011
CN    104610088 A  * 5/2013
(Continued)

OTHER PUBLICATIONS

Kajal et al., Agric. Food Chem., vol. 54, (5), pp. 1868-1873 (2006).*
(Continued)

*Primary Examiner* — Paul V Ward
(74) *Attorney, Agent, or Firm* — Wolf, Greenfield & Sacks, P.C.

(57) ABSTRACT

The present invention provides oxalic amide ligands and uses thereof in copper-catalyzed coupling reaction of aryl halides. Specifically, the present invention provides a use of a compound represented by formula I, wherein definitions of each group are described in the specification. The compound represented by formula I can be used as a ligand in copper-catalyzed coupling reaction of aryl halides for the formation of C—N, C—O and C—S bonds.

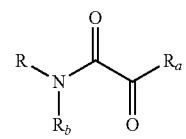

13 Claims, 2 Drawing Sheets

Figure 1:
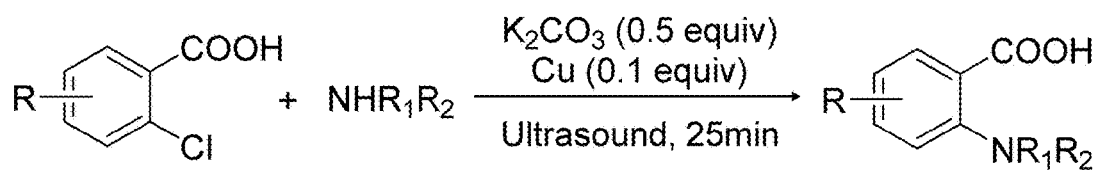

(51) Int. Cl.

| | |
|---|---|
| C07C 231/02 | (2006.01) |
| C07C 233/56 | (2006.01) |
| C07B 41/02 | (2006.01) |
| C07B 43/04 | (2006.01) |
| C07B 45/06 | (2006.01) |
| C07C 41/26 | (2006.01) |
| C07C 45/64 | (2006.01) |
| C07C 209/08 | (2006.01) |
| C07C 209/10 | (2006.01) |
| C07C 213/02 | (2006.01) |
| C07C 213/08 | (2006.01) |
| C07C 221/00 | (2006.01) |
| C07C 231/12 | (2006.01) |
| C07C 231/14 | (2006.01) |
| C07C 253/30 | (2006.01) |
| C07C 315/04 | (2006.01) |
| C07C 319/14 | (2006.01) |
| C07C 319/20 | (2006.01) |
| C07D 207/06 | (2006.01) |
| C07D 207/14 | (2006.01) |
| C07D 207/335 | (2006.01) |
| C07D 209/86 | (2006.01) |
| C07D 213/40 | (2006.01) |
| C07D 213/65 | (2006.01) |
| C07D 213/73 | (2006.01) |
| C07D 213/89 | (2006.01) |
| C07D 215/20 | (2006.01) |
| C07D 215/38 | (2006.01) |
| C07D 215/40 | (2006.01) |
| C07D 217/22 | (2006.01) |
| C07D 231/12 | (2006.01) |
| C07D 233/60 | (2006.01) |
| C07D 239/42 | (2006.01) |
| C07D 241/18 | (2006.01) |
| C07D 241/20 | (2006.01) |
| C07D 241/42 | (2006.01) |
| C07D 263/56 | (2006.01) |
| C07D 277/64 | (2006.01) |
| C07D 277/66 | (2006.01) |
| C07D 295/00 | (2006.01) |
| C07D 295/096 | (2006.01) |
| C07D 295/135 | (2006.01) |
| C07D 307/22 | (2006.01) |
| C07D 307/52 | (2006.01) |
| C07D 307/81 | (2006.01) |
| C07D 317/28 | (2006.01) |
| C07D 317/58 | (2006.01) |
| C07D 317/64 | (2006.01) |
| C07D 317/66 | (2006.01) |
| C07D 333/20 | (2006.01) |
| C07D 335/16 | (2006.01) |
| C07D 471/04 | (2006.01) |
| C07D 495/04 | (2006.01) |
| C07D 333/58 | (2006.01) |
| C07D 213/74 | (2006.01) |
| C07D 223/12 | (2006.01) |
| C07D 223/22 | (2006.01) |
| C07D 333/36 | (2006.01) |
| C07D 333/54 | (2006.01) |
| C07D 239/545 | (2006.01) |
| C07D 207/27 | (2006.01) |
| C07D 209/08 | (2006.01) |
| C07D 211/72 | (2006.01) |

(52) U.S. Cl.
CPC ......... *C07D 335/16* (2013.01); *C07D 471/04* (2013.01); *C07D 495/04* (2013.01); *B01J 2231/4283* (2013.01); *B01J 2231/4288* (2013.01); *B01J 2231/4294* (2013.01); *B01J 2531/16* (2013.01)

(56) References Cited

FOREIGN PATENT DOCUMENTS

| | | |
|---|---|---|
| CN | 104610088 A | 5/2015 |
| JP | 2-502181 | 7/1990 |
| JP | 2009-519947 | 5/2009 |
| WO | 1988/006154 A1 | 8/1988 |
| WO | 2008/097692 A1 | 8/2008 |
| WO | 2012/019076 A1 | 2/2012 |
| WO | 2014/070983 A1 | 5/2014 |

OTHER PUBLICATIONS

Maha et al., BioOrganic & Medicinal Chem., vol. 19 (16), pp. 4746-4771, (2011).*
Chakraborty et al., Chemical hybridizing agents for chickpea (*Cicer arietinum* L.): leads from QSAR analysis of ethyl oxanilates and pyridones. J Agric Food Chem. Mar. 8, 2006;54(5):1868-73.
Fan et al., Assembly of Primary (Hetero)Arylamines via CuI/Oxalic Diamide-Catalyzed Coupling of Aryl Chlorides and Ammonia. Org Lett. Dec. 4, 2015;17(23):5934-7. doi: 10.1021/acs.orglett.5b03230. Epub Nov. 24, 2015.
Fan et al., CuI/Oxalamide Catalyzed Couplings of (Hetero)aryl Chlorides and Phenols for Diaryl Ether Formation. Angew Chem Int Ed Engl. May 17, 2016;55(21):6211-5. doi: 10.1002/anie.201601035. Epub Apr. 13, 2016.
Habash et al., Ligand-based modelling followed by synthetic exploration unveil novel glycogen phosphorylase inhibitory leads. Bioorg Med Chem. Aug. 15, 2011;19(16):4746-71. doi: 10.1016/j.bmc.2011.06.086. Epub Jul. 7, 2011.
Pistillo et al., Molecular characterization and applications of recombinant scFv antibodies to CD152 co-stimulatory molecule. Tissue Antigens. Mar. 2000;55(3):229-38.
Zhang et al., CuI/DMPAO-catalyzed N-arylation of acyclic secondary amines. Org Lett. Jun. 15, 2012;14(12):3056-9. doi: 10.1021/ol301135c. Epub Jun. 4, 2012.
Zhou et al., CuI/Oxalic Diamide Catalyzed Coupling Reaction of (Hetero)Aryl Chlorides and Amines. J Am Chem Soc. Sep. 23, 2015;137(37):11942-5. doi: 10.1021/jacs.5b08411. Epub Sep. 11, 2015.
PCT/CN2016/079500, dated Jul. 25, 2016, International Search Report and Written Opinion.
Blum et al., Synthesis of N-Heterocyclic Carbene-Containing Metal Complexes from 2-(Pentafluorophenyl)Imidazolidines. Supplemental Information. 44 pages. Jan. 1, 2007.
CAS RN-349401-51-0 2. Jul. 29, 2001.
CAS RN-920366-91-2. Feb. 11, 2007.
Cremlyn, Synthesis and spectral data for some derivatives of n-arlyoxamic acid hydrazides. J Chem Eng Data. 1974; 19(3):288-294.
Gross et al., Uber die Reaktion 1,3-disubstituierter 2,2-dichlor-4,5-imid-azolidindione mit sek. Chem ber. 1973; 106:2315-2323.
Mengyang et al., Supporting Information cul/oxalamide catalyzed couplings of (hetero)aryl chlorides and phenols for diaryl ether formation. Apr. 13, 2016.
Ritter et al., Rate Acceleration in Olefin Metathesis through a Fluorine-Ruthenium Interaction. 145 pages. Supplemental Information. Sep. 1, 2006.
Singh et al. Synthesis of N-arylisatins using different heterogeneous catalyst under microwave irradiations. Asian J Chemistry. Jan. 1, 2013; 25(8):4935-4938.

(56) References Cited

OTHER PUBLICATIONS

Stylianides et al., Cyclometalated and alkoxyphenyl-substituted palladium imidazolin-2-ylidene complexes. Synthetic, structural, and catalytic studies. Organometallics. 2007; 26:5627-5635.

Zhang et al., 1-D Structures of assemblies containing oxamidato dicopper building blocks controlled by ditopic N-donor spacers. J Chem Soc Dalton Trans. 2001; 1664-1669.

* cited by examiner

R = Me, OMe, COCH₃, NO₂, CN; R' = Me, OMe, F, ᵗBu

Reaction conditions B reaction conditions D

OXALIC AMIDE LIGANDS, AND USES THEREOF IN COPPER-CATALYZED COUPLING REACTION OF ARYL HALIDES

RELATED APPLICATIONS

This application is a national stage filing under 35 U.S.C. § 371 of International Application PCT/CN2016/079500 entitled "OXALIC ACID MONOAMIDE LIGAND, AND USES THEREOF IN COUPLING REACTION OF COPPER-CATALYZED ARYL HALOGEN SUBSTITUTE" filed Apr. 15, 2016, which claims priority to CN Application No. 201510428566.9, filed Jul. 20, 2015, the entire disclosure of each of which is incorporated by reference herein in its entirety.

TECHNICAL FIELD

The present invention relates to the field of organic synthesis. Specifically, the present invention provides a copper-catalyzed coupling reaction of aryl halide promoted by an oxalic amide ligand, and particularly a coupling reaction of C—N, C—O and C—S bonds formation.

BACKGROUND

Oxalic amides are usually widely concerned due to their various biological activities. For example, monomethyl oxalate can be used as chemical hybridization reagent for *Cicer arietinum*, and oxalate aryldiamide compounds are useful as glycogen phosphorylase inhibitors, or as a small molecule modulator that acts on the CD4-gp120 protein. Until recently, the team led by Dawei Ma uses oxalate 2,6-dimethylphenyl monoamide carboxylic acid as a ligand for copper-catalyzed C—N coupling reaction of aryl iodides and bromides with amines, thus opening up new uses of these compounds. However, this reaction is mainly applicable to the coupling reaction of aryl iodides and bromides.

The transition metal-catalyzed coupling reaction of aryl halides with suitable nucleophiles, such as amines, active methylene compounds, alkynes, phenols, alcohols, thiophenols, sodium sulfinics, sodium sulfides, phosphates and the like, is very efficient for the formation of C—N, C—C, C—O, C—S, and C—P bonds. Generally, due to the high reactivity of aryl iodides and aryl bromides, the corresponding coupling reaction proceeds well under the catalysis of transition metals such as palladium, copper and nickel. Aryl chlorides are cheaper and more readily available, and have more application prospects compared with aryl bromides (iodides). However, high energy of C—Cl bond makes the oxidative addition of transition metal to aryl chlorides hardly occur, and the coupling reaction is more difficult than that of aryl bromides and iodides. Palladium and nickel catalyzed C—N coupling reactions of aryl chlorides have been reported by using sterically hindered phosphine ligands. In 2005, Hartwig and coworkers described the coupling reaction of (hetero)aryl chlorides with primary amines was promoted by a large sterically hindered phosphine ligand with a ferrocene structure. The loading of catalysts and ligands in this system can even be reduced to one hundred thousandth molar equivalent. Such reaction can be accomplished at room temperature for some particular heteroaryl substrates. In addition, a wide range of functionalized (hetero)aryl chlorides were compatible for this transformation. In 2011, Buchwald's group found that the use of different phosphine ligands allowed the coupling reaction of aryl chlorides with primary and secondary amines respectively. The system has a very wide compatibility with substrates. In addition to common aliphatic amines, the aromatic amines with heterocyclic rings also are suitable nucleophiles.

Although the catalysis of metallic palladium and nickel are highly efficient in the amination of aryl chlorides, there are still some problems in large-scale applications: 1. it is required to add large sterically hindered and complex phosphine ligands or N-heterocyclic carbenes ligands; 2. palladium catalyst is expensive, and for zero-valent nickel catalyzed reaction, the operation is quite harsh. In contrast, copper catalysts are cheap, stable and readily available, and the useful ligands are simple. However, the substrates of copper-catalyzed coupling reaction reported so far are mostly limited to aryl iodides and bromides.

In 2007, Pellón's group reported the coupling of 2-chlorobenzoic acid and aliphatic amines with assistance of ortho-substituent effect and ultrasound. Both primary and secondary amines can provide the corresponding coupling products in good yields. However, only aryl chlorides with ortho-carboxyl substituent are suitable for this transformation (Docampo, M. L.; Pellón, R. F.; Estevez-Braun, A.; Ravelo, A. G. *Eur. J. Org. Chem.* 2007, 4111.). This reaction should undergo a nucleophilic substitution process rather than a coupling reaction. In addition, the high reaction temperature is still required. A schematic of this reaction is shown in FIG. 1.

Figure 2:
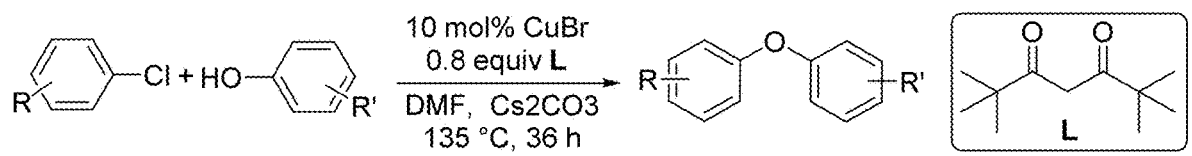

Another report on Ullmann coupling reaction of aryl chlorides came from Taillefer's group. They used 2,2,6,6-tetramethyl-3,5-heptanedione as a ligand to achieve C—O coupling of benzyl chlorides with phenols. However, the addition of large amount ligand as much as 0.8 equivalents made the reaction less economically (Xia, N.; Taillefer, M. *Chem. Eur. J.* 2008, 14, 6037.). A schematic of this reaction is shown in FIG. 2.

In summary, there is no catalytic system for copper-catalyzed coupling reaction of aryl chlorides in the art that enables the reaction to be carried out efficiently.

SUMMARY OF THE INVENTION

The object of the present invention is to provide a catalytic system that is useful for copper-catalyzed coupling reaction of aryl halides, especially aryl chlorides.

In the first aspect of the present invention, it provides a use of a compound of formula I:

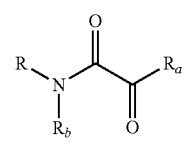

wherein R is selected from the group consisting of a substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O or S; the cycloalkyl or heterocyclic group may be a monocyclic, polycyclic, spiro or bridged ring structure;

$R_a$ is selected from (a) or (b):

(a) OR'; wherein R' is selected from the group consisting of a substituted or unsubstituted C1-C6 alkyl; or (b) N(R")$_2$; wherein each R" is independently selected from the group consisting of H, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure (preferably, N(R")$_2$ is NHR");

$R_b$ is selected from the group consisting of H, and C1-C6 alkyl;

or $R_b$ and R, together with adjacent nitrogen atom, form a substituted or unsubstituted 3- to 20-membered heteroaryl, or substituted or unsubstituted 3- to 20-membered heterocyclic group;

the term "substituted" means that one or more hydrogen atoms on the group is substituted by a substituent selected from the group consisting of halogen, C1-C6 alkyl, halogenated C1-C6 alkyl, C1-C6 alkoxy, C6-C10 aryl, C6-C10 aryl-oxy, C2-C10 ester group (alkyl-COO—), C2-C10 acyl-alkoxy (alkyl-OOC—), C2-C10 acyl (alkyl-CO—), C2-C10 acylamino(alkyl/aryl-NHC(O)—), —COOH, nitro, hydroxy, amino, and amino substituted by one or two C1-C6 alkyl;

wherein it is used as a ligand for copper-catalyzed coupling reaction of aryl halide; wherein the aryl halide is selected from the group consisting of aryl chloride, aryl bromide, aryl iodide, and the combinations thereof.

In another preferred embodiment, R is selected from the group consisting of substituted or unsubstituted phenyl, substituted or unsubstituted naphthyl, substituted or unsubstituted benzyl, substituted or unsubstituted quinolinyl, substituted or unsubstituted

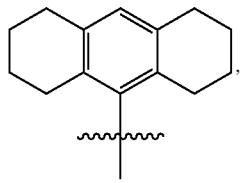 [SMILES: *c1c2c(cc3c1CCCC3)CCCC2]

substituted or unsubstituted adamantyl substituted or unsubstituted C1-C6 alkyl, substituted or unsubstituted

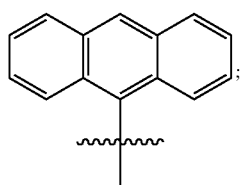 [SMILES: *c1c2ccccc2cc2ccccc12]

or R and $R_b$ together with adjacent nitrogen atom, form a substituted or unsubstituted group selected from the group consisting of

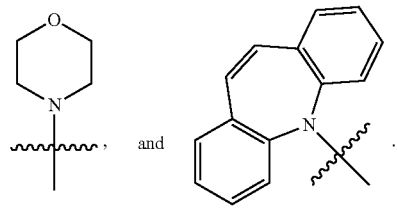 [SMILES: *N1CCOCC1 ; *N1c2ccccc2C=Cc2ccccc21]

In another preferred embodiment, R is selected from the group consisting of substituted or unsubstituted phenyl, substituted or unsubstituted naphthyl, substituted or unsubstituted benzyl, C1-C4 alkyl, pyridyl, and adamantyl;

$R_a$ is selected from (a) or (b):

(a) OR'; wherein R' is selected from the group consisting of substituted or unsubstituted C1-C6 alkyl; or (b) N(R")$_2$; wherein each R" is independently selected from the group consisting of H, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure.

In another preferred embodiment, when $R_a$ is NHR", R" is selected from the group consisting of substituted or unsubstituted phenyl, substituted or unsubstituted naphthyl, substituted or unsubstituted benzyl, C1-C4 alkyl, pyridyl, and adamantyl.

In another preferred embodiment, $R_a$ is NHR".

In another preferred embodiment, the substitution means that one or more hydrogen atoms on the group is substituted by a substituent selected from the group consisting of halogen, methyl, trifluoromethyl, ethyl, isopropyl, tert-butyl, dimethylamino, methoxy, tert-butoxy, —Ac, CH$_3$NHC(O)—, phenyl, phenoxy, —COOH, ester group, nitro, cyano, and hydroxy.

In another preferred embodiment, the aryl halide is aryl chloride.

In the second aspect of the present invention, it provides a coupling reaction method of aryl halide, which comprises carrying out a coupling reaction by using copper as a catalyst and a compound represented by the following formula I as a ligand:

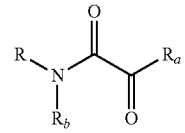

wherein R is selected from the group consisting of substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, Spiro or bridged ring structure;

$R_a$ is selected from (a) or (b):

(a) OR'; wherein R' is selected from the group consisting of substituted or unsubstituted C1-C6 alkyl; or (b) N(R")$_2$; wherein each R" is independently selected from the group consisting of H, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, Spiro or bridged ring structure;

$R_b$ is selected from the group consisting of H, and C1-C6 alkyl;

or $R_b$ and R, together with adjacent nitrogen atom, form a substituted or unsubstituted 3- to 20-membered heteroaryl, or substituted or unsubstituted 3- to 20-membered heterocyclic group;

the term "substituted" means that one or more hydrogen atoms on the group is substituted by a substituent selected from the group consisting of halogen, C1-C6 alkyl, halogenated C1-C6 alkyl, C1-C6 alkoxy, C6-C10 aryl, C6-C10 aryl-oxy, C2-C10 ester group (alkyl-COO—), C2-C10 acyl-alkoxy (alkyl-OOC—), C2-C10 acyl (alkyl-CO—), C2-C10 acylamino (alkyl/aryl-NHC(O)—), —COOH, nitro, cyano, hydroxy, amino, and amino substituted by one or two C1-C6 alkyl;

wherein the aryl halide is selected from the group consisting of aryl chloride, aryl bromide, aryl iodide, and the combinations thereof.

In another preferred embodiment, the copper catalyst is selected from the group consisting of CuI, CuBr, CuCl, CuTc, Cu(OAc)$_2$, CuSO$_4$, Cu$_2$O, CuBr$_2$, CuCl$_2$, CuO, CuSCN, CuCN, Cu(acac)$_2$, and the combinations thereof; preferably is CuI, Cu$_2$O, or Cu(acac)$_2$.

In another preferred embodiment, the reaction is carried out in the presence of a base.

In another preferred embodiment, the base is selected from the group consisting of potassium carbonate, cesium carbonate, potassium phosphate, sodium bicarbonate, potassium bicarbonate, sodium carbonate, lithium hydroxide, sodium hydroxide, and/or hydrates of the base, and the combinations thereof; and preferably is potassium phosphate, cesium carbonate, or lithium hydroxide; and most preferably is potassium phosphate.

In another preferred embodiment, in the reaction, the molar ratio of the ligand to the reactant of aryl halide is 1~50:100, and preferably 5~20:100; and the molar ratio of the ligand to the copper catalyst is 1..5:1, and preferably 1~2:1.

In another preferred embodiment, the reaction comprises:

carrying out reaction of

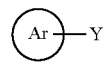

with the coupling reagent in an inert solvent to afford the compound of

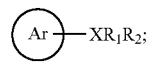

wherein X is selected from the group consisting of N, O and S;

Y is selected from the group consisting of Cl, Br, and I;

is selected from the group consisting of substituted or unsubstituted C6-C20 aryl, and substituted or unsubstituted 3- to 20-membered heteroaryl; wherein the term "substituted" means that one or more hydrogen atoms on the aryl is substituted by a substituent selected from the group consisting of halogen, nitro, cyano, amino unsubstituted or substituted by one or two C1-C6 alkyl or C2-C10 acyl (alkyl-CO—), hydroxy, unsubstituted or halogenated C1-C6 alkyl, C1-C6 alkoxy, C6-C10 aryl, 3- to 20-membered heteroaryl, C6-C10 aryl-oxy, C2-C10 ester group (alkyl-OOO—), C2-C10 acyl (alkyl-CO—), C2-C10 acyl-alkoxy (alkyl-OOC—), C2-C10 acylamino (alkyl-NHC(O)—, aryl-NHC(O)—), —COOH, hydroxy-C1-C10 alkylene, MeS—, sulfuryl, and sulfonamido; wherein two hydrogen atoms on two adjacent carbon atoms of the aryl may be substituted by —(CH$_2$)$_n$— (n is 1, 2, 3, 4, 5 or 6);

the coupling reagent is selected from the group consisting of ammonium hydroxide, ammonia, ammonium salts (preferably ammonium chloride, ammonium carbonate, ammonium sulfate, ammonium hydrogenphosphate, or the combinations thereof)/hydroxide solution (preferably potassium hydroxide solution), C* (having 2 to 19 carbon atoms and may be a saturated, partially unsaturated or aromatic ring), $R_cC(O)NHR_2$, $R_1SO_2M$ (preferably, M is sodium, potassium), sodium azide, NHR$_1$R$_2$, R$_1$OH, R$_1$SH, and hydroxide (preferably lithium hydroxide, or a mixture of potassium phosphate, potassium carbonate, or cesium carbonate and water);

$R_1$, $R_2$, $R_c$ are each independently selected from the group consisting of H, substituted or unsubstituted C1-C6 alkyl, substituted or unsubstituted C1-C6 alkenyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, substituted or unsubstituted C1-C5 alkyl-C3-C20 cycloalkyl, substituted or unsubstituted 3- to 20-membered heterocyclic group, and substituted or unsubstituted C1-C5 alkyl-3- to 20-membered heterocyclic group;

or R$_1$ and R$_2$, together with adjacent nitrogen atom, form a substituted or unsubstituted 3- to 20-membered heterocyclic group, or substituted or unsubstituted 3- to 20-membered hetero aryl;

or R$_c$ and R$_2$, together with adjacent C(O)NH, form a substituted or unsubstituted 3- to 20-membered heterocyclic group, or substituted or unsubstituted 3- to 20-membered heteroaryl;

wherein the heteroaryl or heterocyclic group has 1 to 5 heteroatoms selected from the group consisting of N, O and S; the cycloalkyl or heterocyclic group may be a monocyclic, polycyclic, spiro or bridged ring structure;

the term "substituted" means that one or more hydrogen atoms on the group is substituted by a substituent selected from the group consisting of halogen, cyano, oxo (i.e. two hydrogen atoms on the same carbon atom of the group are substituted by =O), C1-C6 alkyl, halogenated C1-C6 alkyl, C1-C6 alkoxy, C6-C10 aryl, C6-C10 aryl-oxy, C2-C10 ester group (alkyl-OOO—), C2-C10 acyl-alkoxy (alkyl-OOC—), C2-C10 acyl (alkyl-CO—), C2-C10 acylamino (alkyl/aryl-NHC(O)—), —COOH, nitro, hydroxy, amino, amino substituted by one or two C1-C6 alkyl, and C1-C6 alkyl-S—.

In another preferred embodiment, the inert solvent is selected from the group consisting of DMSO, DMF, DMA, NMP, acetonitrile, isopropanol, and the combinations thereof; and preferably is DMSO and/or DMF and/or DMSO/H$_2$O.

In another preferred embodiment, the reaction temperature is 50-180° C., preferably 100-130° C.

In another preferred embodiment, the reaction includes the following (1), (2), (3), (4), (5), (6), (7) or (8):

(1) Carrying out reaction of

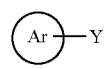

with NHR$_1$R$_2$ in an inert solvent to afford

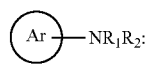

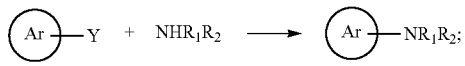

wherein the definition of each group is described as above;

(2) Carrying out reaction of

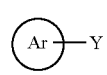

with ammonia source in an inert solvent to afford

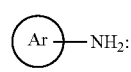

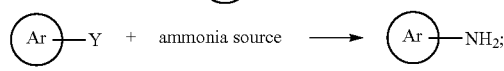

wherein the definition of each group is described as above;

the ammonia source is selected from the group consisting of ammonia, ammonium hydroxide, ammonium chloride, ammonium carbonate, ammonium bicarbonate, ammonium sulfate, ammonium nitrate, ammonium phosphate, diammonium hydrogen phosphate, sodium azide, preferably ammonia, ammonium hydroxide, ammonium chloride and diammonium hydrogen phosphate.

(3) Carrying out reaction of

with R$_1$OH in an inert solvent to afford

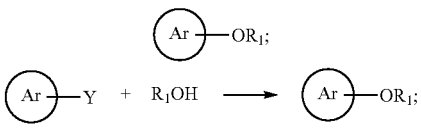

wherein the definition of each group is described as above;

(4) Carrying out reaction of

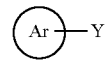

with R$_1$SH in an inert solvent to afford

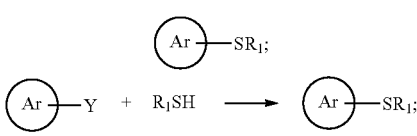

wherein the definition of each group is described as above.

In another preferred embodiment, the reaction includes the following of (5):

(5) Carrying out reaction of

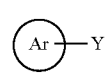

with G* in an inert solvent to afford

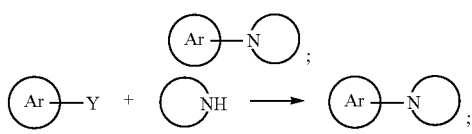

wherein, G* is a substituted or unsubstituted 3- to 20-membered ring containing N atom, and the 3- to 20-membered ring may be saturated, unsaturated or aromatic, while the definition of each of the rest groups is as described above.

In another preferred embodiment, the reaction includes the following reaction (6):

(6) Carrying out reaction of

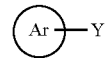

with

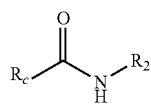

in an inert solvent to afford

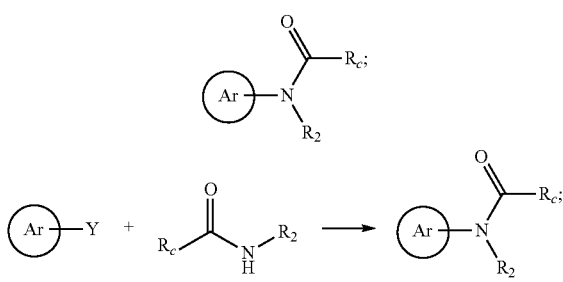

wherein $R_c$ is selected from the group consisting of H, substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure;

or $R_c$ and $R_2$, together with adjacent C(O)NH, form a substituted or unsubstituted 3- to 20-membered heterocyclic group, or substituted or unsubstituted 3- to 20-membered heteroaryl;

the term "substituted" means that one or more hydrogen atoms on the group is substituted by a substituent selected from the group consisting of halogen, C1-C6 alkyl, C1-C6 alkoxy, C6-C10 aryl, C6-C10 aryl-oxy, C2-C10 ester group (alkyl-OOO—), C2-C10 acyl (alkyl-CO—), C2-C10 acylamino (alkyl-NHC(O)—, aryl-NHC(O)—), and —COOH, the definition of each of the rest groups is described as above.

In another preferred embodiment, the reaction includes the following reaction (7):

(7) Carrying out reaction of

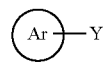

in an inert solvent to afford

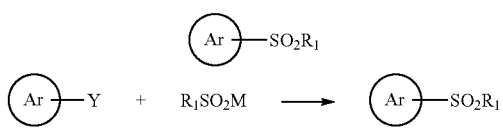

wherein the definition of each group is described as above.

In another preferred embodiment, the reaction includes the following reaction (8):

(8) Carrying out reaction of

with hydroxide or OH⁻ hydrolyzed from base in an inert solvent to afford

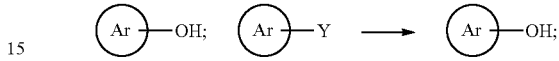

wherein the definition of each group is described as above.

In another preferred embodiment, in reaction (1), the ligand is selected from the group consisting of L-I-25, L-I-27, L-II-7, L-II-9, L-II-31, L-II-38, and L-II-64, and most preferably is L-II-38, L-II-31 or L-II-64.

In another preferred embodiment, in reaction (1), the inert solvent may be DMSO, DMF, DMA, NMP, acetonitrile, isopropanol, THF, or 1,4-dioxane, and preferably DMSO, DMF, DMA or the combinations thereof, and most preferably DMSO.

In another preferred embodiment, in reaction (1), the reaction temperature is at 50-180° C., and preferably 100-130° C.

In another preferred embodiment, in reaction (2), the ligand is selected from the group consisting of L-I-27, L-II-9, L-II-34, L-II-30, L-II-38, L-II-64, L-II-71, and L-II-73, and most preferably is L-II-38, L-II-64 or L-II-71.

In another preferred embodiment, in reaction (2), the base is selected from the group consisting of potassium carbonate, cesium carbonate, potassium phosphate, sodium carbonate, sodium bicarbonate, potassium bicarbonate, and the combinations thereof; and preferably is potassium phosphate.

In another preferred embodiment, in reaction (2), when the ammonia source is ammonium salt, the reaction is carried out in the presence of a strong base (preferably in the presence of KOH).

In another preferred embodiment, in reaction (2), the solvent is selected from the group consisting of DMSO, DMF, DMA, NMP, acetonitrile, and isopropanol, and preferably is DMSO, DMF, DMA or the combinations thereof; and most preferably is DMSO.

In another preferred embodiment, in reaction (2), the reaction temperature is at 50-180° C., preferably 100-130° C.

In another preferred embodiment, in reaction (3), the ligand is preferably L-II-34.

In another preferred embodiment, in reaction (3), the base is selected from the group consisting of potassium carbonate, cesium carbonate, potassium phosphate, sodium carbonate, sodium bicarbonate, potassium bicarbonate, and the combinations thereof; and preferably is potassium phosphate.

In another preferred embodiment, in reaction (3), the solvent is selected from the group consisting of DMSO, DMF, DMA, NMP, acetonitrile, isopropanol, THF, 1,4-dioxane, and the combinations thereof; and preferably is DMSO.

In another preferred embodiment, in reaction (3), the reaction temperature is at 50-180° C., preferably 100-130° C.

In another preferred embodiment, in reaction (4), the ligand is L-II-34.

In another preferred embodiment, in reaction (4), the solvent is selected from the group consisting of DMSO, DMF, DMA, NMP, acetonitrile, isopropanol, THF, 1,4-dioxane, and the combinations thereof; and preferably is DMSO.

In another preferred embodiment, in reaction (4), the reaction temperature is at 50-180° C., and preferably 100-130° C.

In another preferred embodiment, in reaction (5), the ligand is preferably L-II-82.

In another preferred embodiment, in reaction (5), the base is selected from the group consisting of potassium carbonate, cesium carbonate, potassium phosphate, sodium carbonate, sodium bicarbonate, potassium bicarbonate, and the combinations thereof; and preferably is potassium phosphate.

In another preferred embodiment, in reaction (5), the solvent is selected from the group consisting of DMSO, DMF, DMA, NMP, acetonitrile, tert-butanol, isopropanol, THF, 1,4-dioxane, and the combinations thereof; and preferably is DMSO.

In another preferred embodiment, in reaction (5), the reaction temperature is at 50-180° C., preferably 100-130° C.

In another preferred embodiment, in reaction (6), the ligand is preferably L-II-83, L-II-90.

In another preferred embodiment, in reaction (6), the base is selected from the group consisting of potassium carbonate, cesium carbonate, potassium phosphate, sodium carbonate, sodium bicarbonate, potassium bicarbonate, and the combinations thereof; and preferably is potassium phosphate.

In another preferred embodiment, in reaction (6), the solvent is selected from the group consisting of DMSO, DMF, DMA, NMP, acetonitrile, tert-butanol, isopropanol, THF, 1,4-dioxane, and the combinations thereof; and preferably is DMSO.

In another preferred embodiment, in reaction (6), the reaction temperature is at 50-180° C., and preferably 100-130° C.

In another preferred embodiment, in reaction (7), the ligand is preferably L-II-3, L-II-37.

In another preferred embodiment, in reaction (7), the base is selected from the group consisting of potassium carbonate, cesium carbonate, potassium phosphate, sodium carbonate, sodium bicarbonate, potassium bicarbonate, and the combinations thereof; and preferably is potassium phosphate.

In another preferred embodiment, in reaction (7), the solvent is selected from the group consisting of DMSO, DMF, DMA, NMP, acetonitrile, tert-butanol, isopropanol, THF, 1,4-dioxane, and the combinations thereof; and preferably is DMSO.

In another preferred embodiment, in reaction (7), the reaction temperature is at 50-180° C., and preferably 100-130° C.

In another preferred embodiment, in reaction (8), the ligand is preferably L-II-65, L-II-93.

In another preferred embodiment, in reaction (8), the base is selected from the group consisting of potassium carbonate, cesium carbonate, potassium phosphate, sodium carbonate, sodium bicarbonate, potassium bicarbonate, lithium hydroxide, sodium hydroxide, and/or a hydrate of the base, and the combinations thereof; and preferably is lithium hydroxide.

In another preferred embodiment, in reaction (8), the solvent is selected from the group consisting of DMSO, DMF, DMA, NMP, acetonitrile, isopropanol, THF, 1,4-dioxane, tert-butanol, and/or a mixture of one or more of the foregoing solvents and water, and the combinations thereof; and preferably is DMSO/H$_2$O.

In another preferred embodiment, in reaction (8), the reaction temperature is at 50-180° C., and preferably 100-130° C.

In the third aspect of the present invention, it provides a catalyst system for aryl coupling reaction which comprises: a copper catalyst, a ligand, a base, and an organic solvent;

wherein the copper catalyst is selected from the group consisting of CuI, CuBr, CuCl, CuTc, Cu(OAc)$_2$, CuSO$_4$, Cu$_2$O, CuBr$_2$, CuCl$_2$, CuO, CuSCN, CuCN, Cu(acac)$_2$, and the combinations thereof; and preferably is CuI, Cu$_2$O, or Cu(acac)$_2$;

the base is selected from the group consisting of potassium carbonate, cesium carbonate, potassium phosphate, sodium bicarbonate, potassium bicarbonate, sodium carbonate, lithium hydroxide, sodium hydroxide, tetrabutyl ammonium hydroxide, and/or a hydrate of the base, and the combinations thereof; and preferably is potassium phosphate, cesium carbonate, or lithium hydroxide;

the solvent is selected from the group consisting of DMSO, DMF, DMA, NMP, acetonitrile, isopropanol, 1,4-dioxane, tetrahydrofuran, toluene, tert-butanol, and the combinations thereof; and preferably is DMSO and/or DMF and/or DMSO/H$_2$O;

the ligand has a structure as shown by the following formula (I):

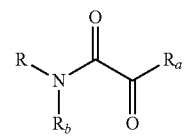

I wherein the definition of each group is as described in the first aspect of the present invention.

In another preferred embodiment, the catalytic system is used for coupling reaction of aryl halide; the aryl halide is selected from the group consisting of aryl chloride, aryl bromide, and aryl iodide.

In another preferred embodiment, the catalytic system is used for coupling reaction of aryl chloride.

In the fourth aspect of the present invention, it provides a compound of the following formula (I):

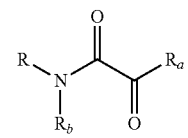

wherein R is selected from the group consisting of substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl- 3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, Spiro or bridged ring structure;

$R_a$ is selected from (a) or (b):

(a) OR'; wherein R' is selected from the group consisting of Me, and Et; or (b) $N(R'')_2$; wherein each R" is independently selected from the group consisting of H, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure;

$R_b$ is selected from the group consisting of H, and C1-C6 alkyl;

or $R_b$ and R, together with adjacent nitrogen atom, form a substituted or unsubstituted 3- to 20-membered heteroaryl, or substituted or unsubstituted 3- to 20-membered heterocyclic group;

and when $R_a$ is selected from (a) and R' is H, R is naphthyl substituted by methyl;

the term "substituted" means that one or more hydrogen atoms on the group is substituted by a substituent selected from the group consisting of halogen, C1-C6 alkyl, halogenated C1-C6 alkyl, C1-C6 alkoxy, C6-C10 aryl, C6-C10 aryl-oxy, C2-C10 ester group (alkyl-COO—), C2-C10 acyl-alkoxy (alkyl-OOC—), C2-C10 acyl (alkyl-CO—), C2-C10 acylamino (alkyl/aryl-NHC(O)—), —COOH, nitro, cyano, hydroxy, amino, and amino substituted by one or two C1-C6 alkyl.

In another preferred embodiment, in the compound, any one of R, $R_a$, $R_b$, R', $R_1$, $R_2$, $R_4$ and

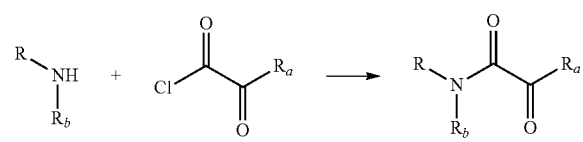

is the corresponding group in the corresponding specific compounds in this application respectively.

In another preferred embodiment, the compounds of formula (I) are those shown in Table 1 or Table 2.

In the fifth aspect of the present invention, it provides a process for preparation of a compound in the fourth aspect of the present invention, which is carried out by a method selected from the process (i), (ii) or (II):

process (i) comprises a step of:

carrying out reaction of R—NH—$R_b$ with

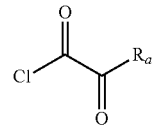

in an inert solvent to afford the compound of formula (I); process (ii) comprises a step of:

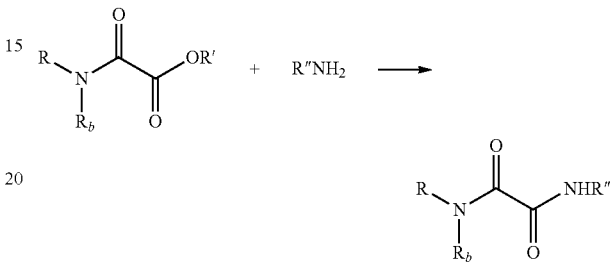

carrying out reaction of R"—$NH_2$ with

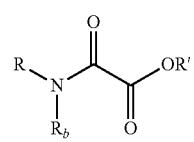

in an inert solvent to afford the compound of formula (I); process (II) comprises a step of:

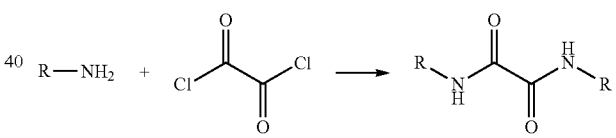

Carrying out reaction of R—$NH_2$ with oxalyl chloride in an inert solvent to afford the compound of formula (I); wherein the definition of each group is as described in the fourth aspect of the present invention.

In another preferred embodiment, in process (i), the inert solvent is selected from the group consisting of tetrahydrofuran, dichloromethane, and DMF.

In another preferred embodiment, in process (i), the reaction is carried out in the presence of triethylamine.

In another preferred embodiment, in process (i), the reaction is carried out at −5° C. to 40° C.

In another preferred embodiment, in process (ii), the inert solvent is selected from the group consisting of tetrahydrofuran, dichloromethane, and DMF.

In another preferred embodiment, in process (ii), the reaction is carried out at 10° C. to 80° C. (preferably room temperature, i.e. 10-40° C.).

In another preferred embodiment, in process (II), the inert solvent is selected from the group consisting of tetrahydrofuran, dichloromethane, and DMF.

In another preferred embodiment, in process (II), the reaction is carried out in the presence of triethylamine.

In another preferred embodiment, in process (II), the reaction is carried out at −5° C. to 40° C.

It should be understood that each of the above technical features of the invention and each technical feature specifically described below (such as in Examples) can be combined with each other within the scope of the present invention so as to constitute new or preferred technical solutions which need not be specified again herein.

DETAIL DESCRIPTION OF THE INVENTION

After a long-term and intensive study, the inventors have provided a class of oxalate (mono, bis) amide ligands suitable for copper-catalyzed coupling reaction of aryl chloride. A suitable catalytic system composed of such ligands and copper reagent, base and solvent can be used for copper-catalyzed coupling reaction of aryl halides, and especially, can effectively promote coupling of copper-catalyzed aryl chloride with various nucleophiles, to generate C—N, C—O, C—S bonds and synthesize many useful small molecules, while such coupling is difficult to occur under the normal condition. Mild reaction conditions and wide reaction scope make this method have good prospect in industrial application.

Terms

As used herein, the term "halogen" refers to fluorine, chlorine, bromine, or iodine.

The term "halo" means that one or more hydrogen atoms on a group are substituted by halogen.

The term "alkyl" refers to a straight or branched alkyl. When alkyl has a precedent carbon atom number limitation (e.g., C1-C6), the alkyl group contains 1-6 carbon atoms, such as methyl, ethyl, propyl, isopropyl, butyl, isobutyl, sec-butyl, tert-butyl, or the like.

The term "cycloalkyl" refers to a saturated or partially saturated monocyclic, bicyclic or tricyclic (fused, bridged or spiro) ring system. The cycloalkyl may have 3 to 20 carbon atoms. When the cycloalkyl has a precedent carbon atom number limitation (e.g., C3-C20), the cycloalkyl contains 3 to 20 carbon atoms, such as cyclopropyl, cyclobutyl, cyclopentyl, cycloheptyl, or the like. The cycloalkyl may be a monocyclic, polycyclic, spiro or bridged ring.

As used herein, the term "alkoxy" refers to an alkyl (e.g., —O-alkyl, wherein alkyl is defined as above) attached through an oxygen atom, such as, but not limited to, methoxy, ethoxy, propoxy, isopropoxy, butoxy, isobutoxy, sec-butoxy, tert-butoxy, or the like. When the alkoxy has a precedent carbon atom number limitation (e.g., C1-C6), the cycloalkyl contains 1-6 carbon atoms.

The term "aryl" refers to a monocyclic, bicyclic, or fused aromatic hydrocarbon group, and the aryl may be substituted or unsubstituted. When an aryl has a precedent carbon atom number limitation (e.g., C6-C20), the aryl contains 6-20 carbon atoms. Examples of aryl include but are not limited to, phenyl, biphenyl, naphthyl, or the like (each carbon atom may be optionally substituted).

The term "heteroaryl" refers to a monocyclic, bicyclic, or fused aromatic group that includes at least one heteroatom selected from N, O, or S. The heteroaryl can be a 3- to 20-membered aromatic ring group which has 1-5 heteroatoms each independently selected from N, O or S. Examples of heteoaryl include, but are not limited to, pyridine, pyrimidine, pyrrole, indazole, indole, furan, benzofuran, thiophene, or the like.

The term "heterocyclic group" refers to a monocyclic or fused ring, which is a saturated or partially saturated substituent comprising at least one same or different heteroatom selected from N, O or S. The heterocyclic group may be a 3- to 20-membered heterocyclic group having 1 to 5 heteroatoms each independently selected from N, O or S. Examples of the heterocyclic group include, but are not limited to, a nitrogen heterocyclic group, an oxygen heterocyclic group, a sulfur heterocyclic group, a nitrogen and oxygen heterocyclic group and so on.

The term "ester group" refers to a group having the structure of "alkyl-OOO—", wherein alkyl is defined as above.

The term "acyl" refers to a group having the structure of "alkyl-CO—", wherein alkyl is defined as above.

The term "acylamino" refers to a group having the structure of "alkyl-NHC(O)—" or "aryl-NHC(O)—", wherein alkyl and aryl are defined above.

Ligand

Unless otherwise specified, the term "ligand" used herein refers to a ligand used in a copper catalyzed coupling reaction of aryl chloride.

The ligand useful in the present invention has the structure shown in the foregoing formula (I), and the preferred ligand has a structure selected from the following group (each group is defined as above):

The first class of ligand: oxalic monoamide mono-methyl/ethyl ester

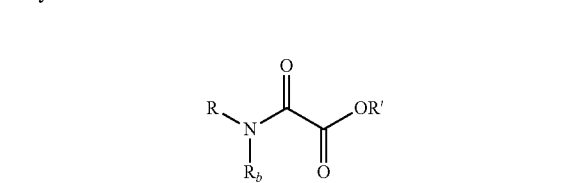

wherein the definition of each group is described as above, and preferably, R is phenyl, substituted phenyl, naphthyl, pyridyl, benzyl, substituted benzyl, adamantyl etc.

More preferred oxalic monoamide mono-methyl/ethyl ester ligands have the structures as shown in Table 1 below:

TABLE 1

| oxalic monoamide mono-methyl/ethyl ester ligand | |
|---|---|
| ![structure] | L-I-1 |
| ![structure] | L-I-2 |
| ![structure] | L-I-3 |
| ![structure] | L-I-4 |

TABLE 1-continued
oxalic monoamide mono-methyl/ethyl ester ligand
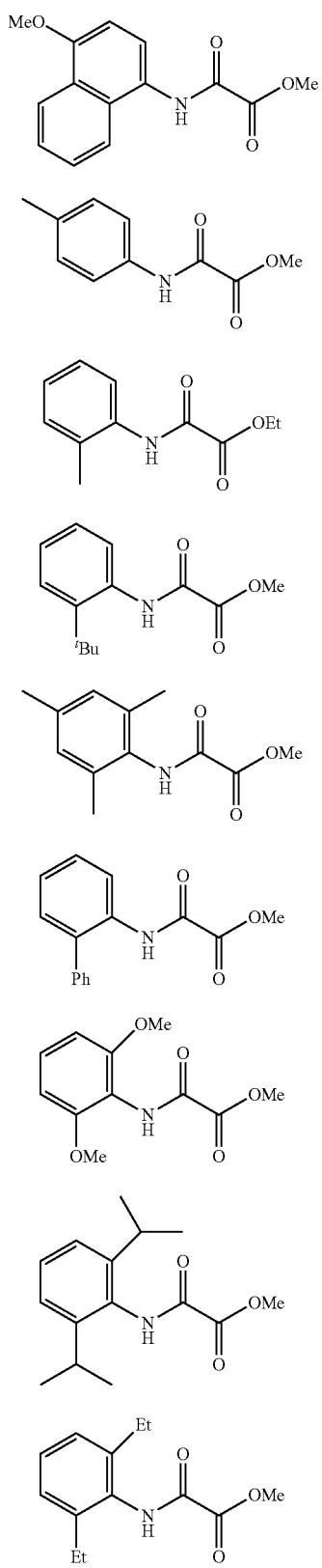
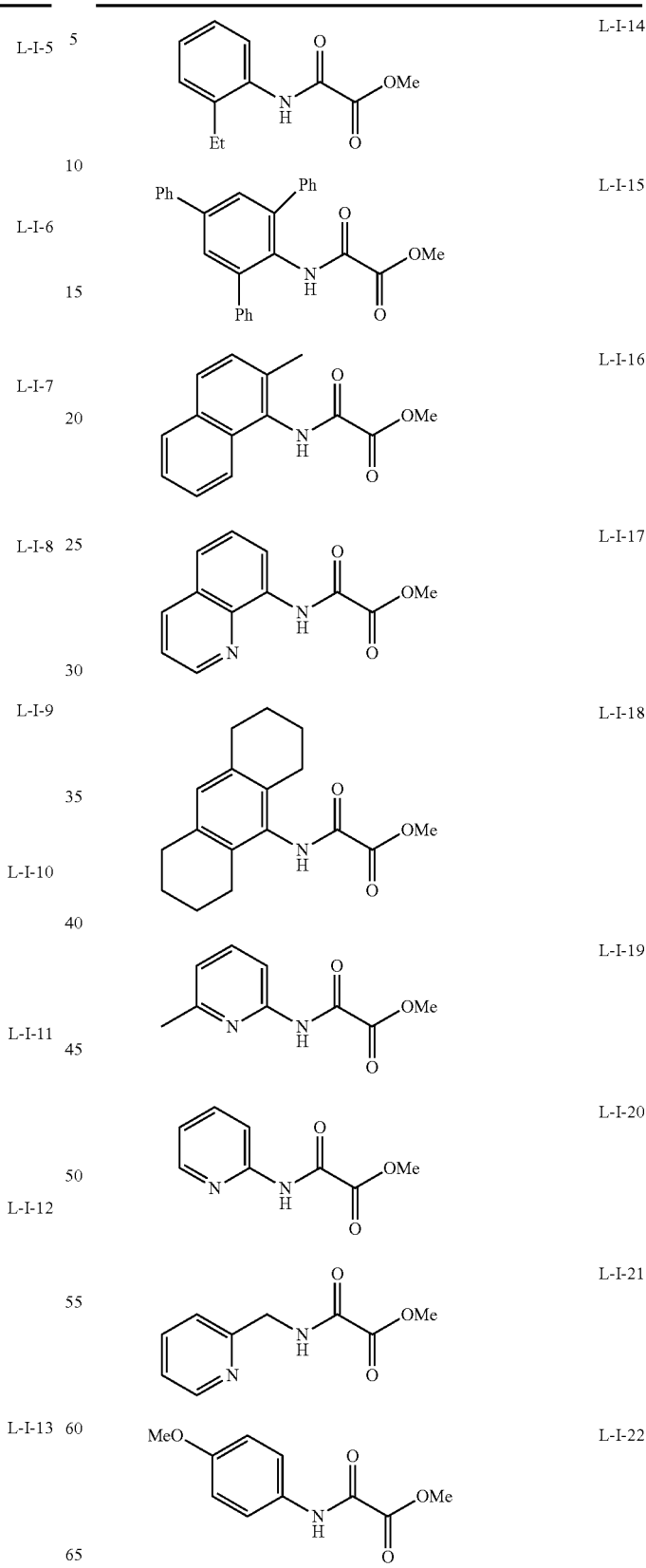

TABLE 1-continued
oxalic monoamide mono-methyl/ethyl ester ligand
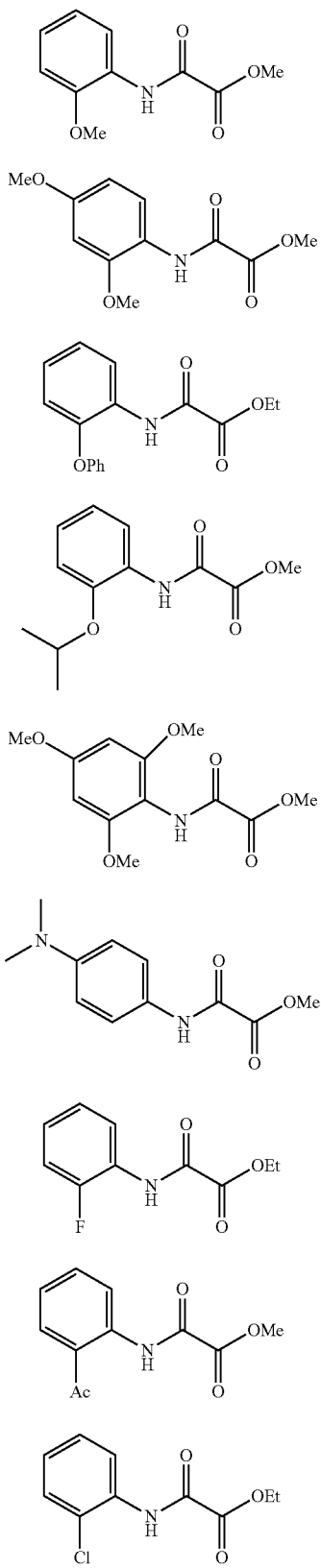
L-I-23
L-I-24
L-I-25
L-I-26
L-I-27
L-I-28
L-I-29
L-I-30
L-I-31
TABLE 1-continued
oxalic monoamide mono-methyl/ethyl ester ligand
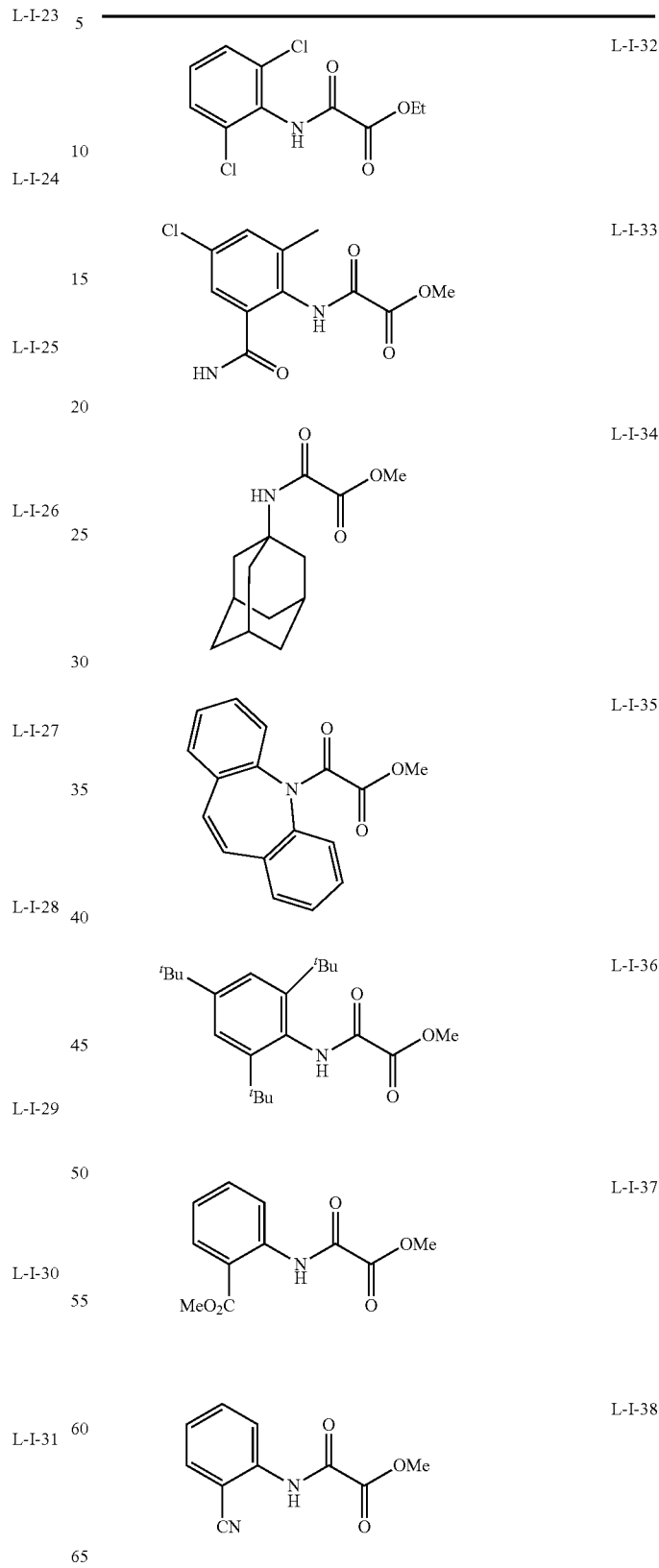
L-I-32
L-I-33
L-I-34
L-I-35
L-I-36
L-I-37
L-I-38

TABLE 1-continued oxalic monoamide mono-methyl/ethyl ester ligand

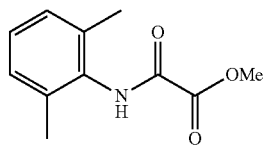

L-I-39

The second class of ligand: Oxalic Diamide

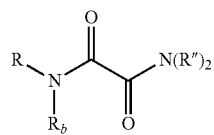

wherein the definition of each group is described as above, and preferably, R is phenyl, substituted phenyl, naphthyl, anthryl, benzyl, substituted benzyl, C1-C4 alkyl, pyridyl, adamantyl etc.; and R" is phenyl, substituted phenyl, naphthyl, benzyl, substituted benzyl, C1-C4 alkyl, pyridyl, adamantyl etc. (R may be equal to or not equal to R").

More preferred oxalic diamide ligands have the structures as shown in Table 2 below:

TABLE 2

Oxalic Diamide

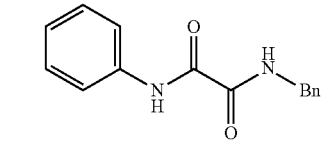 [SMILES: O=C(NCc1ccccc1)C(=O)Nc1ccccc1]

L-II-1

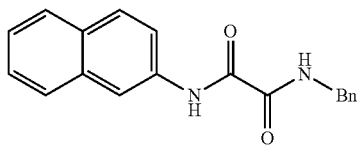 [SMILES: O=C(NCc1ccccc1)C(=O)Nc1ccc2ccccc2c1]

L-II-2

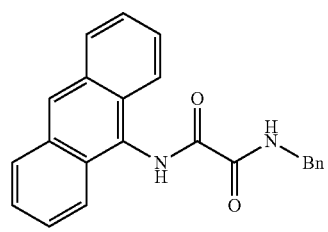 [SMILES: O=C(NCc1ccccc1)C(=O)Nc1c2ccccc2cc2ccccc12]

L-II-3

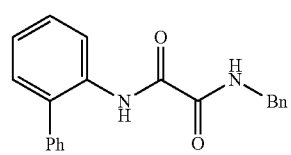 [SMILES: O=C(NCc1ccccc1)C(=O)Nc1ccccc1-c1ccccc1]

L-II-4

TABLE 2-continued

Oxalic Diamide

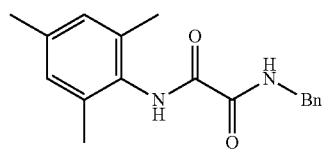 [SMILES: Cc1cc(C)c(NC(=O)C(=O)NCc2ccccc2)c(C)c1]

L-II-5

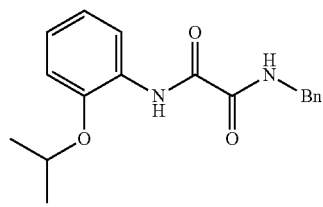 [SMILES: CC(C)Oc1ccccc1NC(=O)C(=O)NCc1ccccc1]

L-II-6

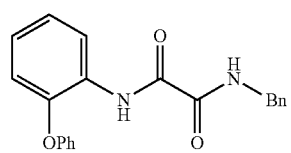 [SMILES: O=C(NCc1ccccc1)C(=O)Nc1ccccc1Oc1ccccc1]

L-II-7

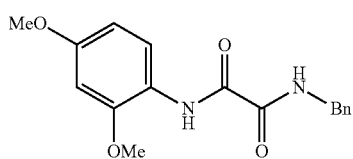 [SMILES: COc1ccc(NC(=O)C(=O)NCc2ccccc2)c(OC)c1]

L-II-8

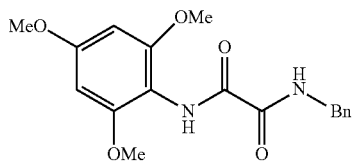 [SMILES: COc1cc(OC)c(NC(=O)C(=O)NCc2ccccc2)c(OC)c1]

L-II-9

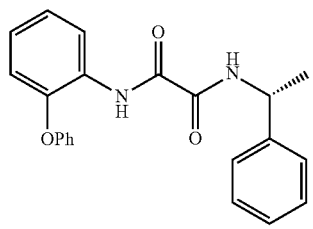 [SMILES: C[C@@H](NC(=O)C(=O)Nc1ccccc1Oc1ccccc1)c1ccccc1]

L-II-10

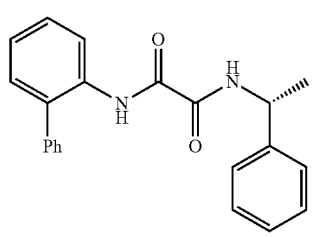 [SMILES: C[C@@H](NC(=O)C(=O)Nc1ccccc1-c1ccccc1)c1ccccc1]

L-II-11

TABLE 2-continued

Oxalic Diamide

L-II-12 through L-II-29 (chemical structures)

TABLE 2-continued

Oxalic Diamide

| Compound | ID |
|---|---|
| 2,4,6-trimethylphenyl on both sides of oxalamide | L-II-30 |
| 2-phenoxyphenyl on both sides | L-II-31 |
| 2-isopropoxyphenyl on both sides | L-II-32 |
| 2,6-dimethoxyphenyl on both sides | L-II-33 |
| 2,6-diethylphenyl on both sides | L-II-34 |
| 2,6-diisopropylphenyl on both sides | L-II-35 |
| 2,4-dimethoxyphenyl on both sides | L-II-36 |
| 2-biphenyl on both sides | L-II-37 |
| 2,4,6-trimethoxyphenyl on both sides | L-II-38 |
| 2-methylnaphthyl–C(O)C(O)–NHBn | L-II-39 |
| 2-methoxyphenyl–NHC(O)C(O)–NHBn | L-II-40 |
| 1-naphthyl–NHC(O)C(O)–NHBn | L-II-41 |
| 2-tert-butylphenyl–NHC(O)C(O)–NHBn | L-II-42 |
| 4-nitro-2-phenylphenyl–NHC(O)C(O)–NHBn | L-II-43 |
| 4-fluoro-2-phenylphenyl–NHC(O)C(O)–NHBn | L-II-44 |
| 4-trifluoromethyl-2-phenylphenyl–NHC(O)C(O)–NHBn | L-II-45 |
| 4-methoxycarbonyl-2-phenylphenyl–NHC(O)C(O)–NHBn | L-II-46 |

TABLE 2-continued

Oxalic Diamide

| Structure | ID |
|---|---|
| 4-methyl-2-phenyl-phenyl-NH-C(O)-C(O)-NH-Bn | L-II-47 |
| 2,4-diphenyl-phenyl-NH-C(O)-C(O)-NH-Bn | L-II-48 |
| 4-MeO-2-Ph-phenyl-NH-C(O)-C(O)-NH-Bn | L-II-49 |
| 4-(Et₂N)-2-Ph-phenyl-NH-C(O)-C(O)-NH-Bn | L-II-50 |
| 4-F-2,6-dimethyl-phenyl-NH-C(O)-C(O)-NH-Bn | L-II-51 |
| 4-NO₂-2,6-dimethyl-phenyl-NH-C(O)-C(O)-NH-Bn | L-II-52 |
| 4-NMe₂-2,6-dimethyl-phenyl-NH-C(O)-C(O)-NH-Bn | L-II-53 |
| 4-HO-2,6-dimethyl-phenyl-NH-C(O)-C(O)-NH-Bn | L-II-54 |
| 2,6-dimethyl-phenyl-NH-C(O)-C(O)-NH-Bn | L-II-55 |
| 4-tBu-2,6-dimethyl-phenyl-NH-C(O)-C(O)-NH-Bn | L-II-56 |
| bis(2-methyl-naphthalen-1-yl) oxalamide | L-II-57 |
| bis(4-fluoro-2,6-dimethyl-phenyl) oxalamide | L-II-58 |
| bis(4-MeO₂C-2,6-dimethyl-phenyl) oxalamide | L-II-59 |
| bis(4-HO₂C-2,6-dimethyl-phenyl) oxalamide | L-II-60 |
| bis(4-NO₂-2,6-dimethyl-phenyl) oxalamide | L-II-61 |
| bis(2,6-dimethyl-phenyl) oxalamide | L-II-62 |
| bis(4-tBu-2,6-dimethyl-phenyl) oxalamide | L-II-63 |

TABLE 2-continued

Oxalic Diamide

L-II-64: 4-MeO-2,6-dimethylphenyl / 2,6-dimethyl-4-MeO-phenyl oxalamide

L-II-65: 4-HO-2,6-dimethylphenyl / 2,6-dimethyl-4-HO-phenyl oxalamide

L-II-66: 4-(dimethylamino)-2,6-dimethylphenyl / 2,6-dimethyl-4-(dimethylamino)phenyl oxalamide L-II-67: 4-nitro-2-phenylphenyl / 2-phenyl-4-CF$_3$-phenyl oxalamide L-II-68: 4-fluoro-2-phenylphenyl / 2-phenyl-4-fluorophenyl oxalamide L-II-69: 4-CF$_3$-2-phenylphenyl / 2-phenyl-4-CF$_3$-phenyl oxalamide L-II-70: 4-(MeO$_2$C)-2-phenylphenyl / 2-phenyl-4-(CO$_2$Me)phenyl oxalamide L-II-71: 4-methyl-2-phenylphenyl / 2-phenyl-4-methylphenyl oxalamide L-II-72: 2,4-diphenylphenyl / 2,4-diphenylphenyl oxalamide L-II-73: 4-MeO-2-phenylphenyl / 2-phenyl-4-OMe-phenyl oxalamide L-II-74: 4-(diethylamino)-2-phenylphenyl / 2-phenyl-4-(diethylamino)phenyl oxalamide L-II-75: 2-(methoxycarbonyl)phenyl / N-benzyl oxalamide L-II-76: 2-cyanophenyl / N-benzyl oxalamide L-II-77: 2,4,6-trimethoxy-3-(CO$_2$Me)phenyl / 2-(MeO$_2$C)-3,4,6-trimethoxyphenyl oxalamide L-II-78: 2,4-dimethoxy-6-fluorophenyl / 2-fluoro-4,6-dimethoxyphenyl oxalamide L-II-79: bis(benzo[d][1,3]dioxol-5-ylmethyl) oxalamide TABLE 2-continued
Oxalic Diamide
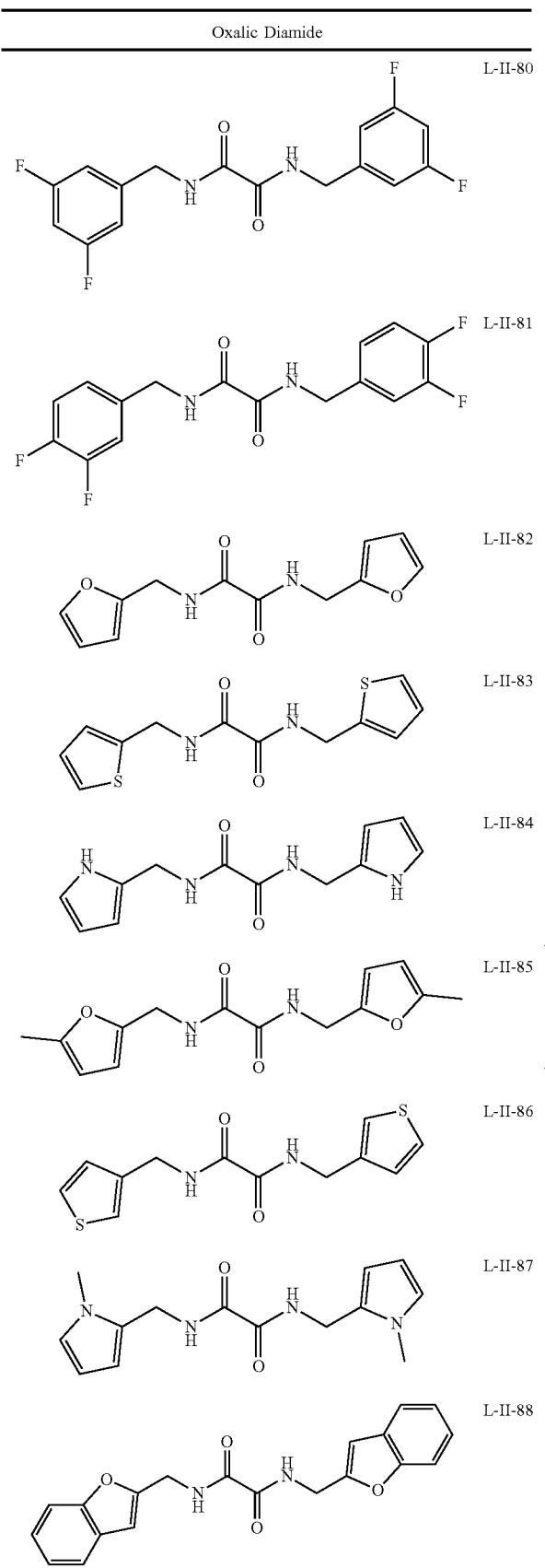
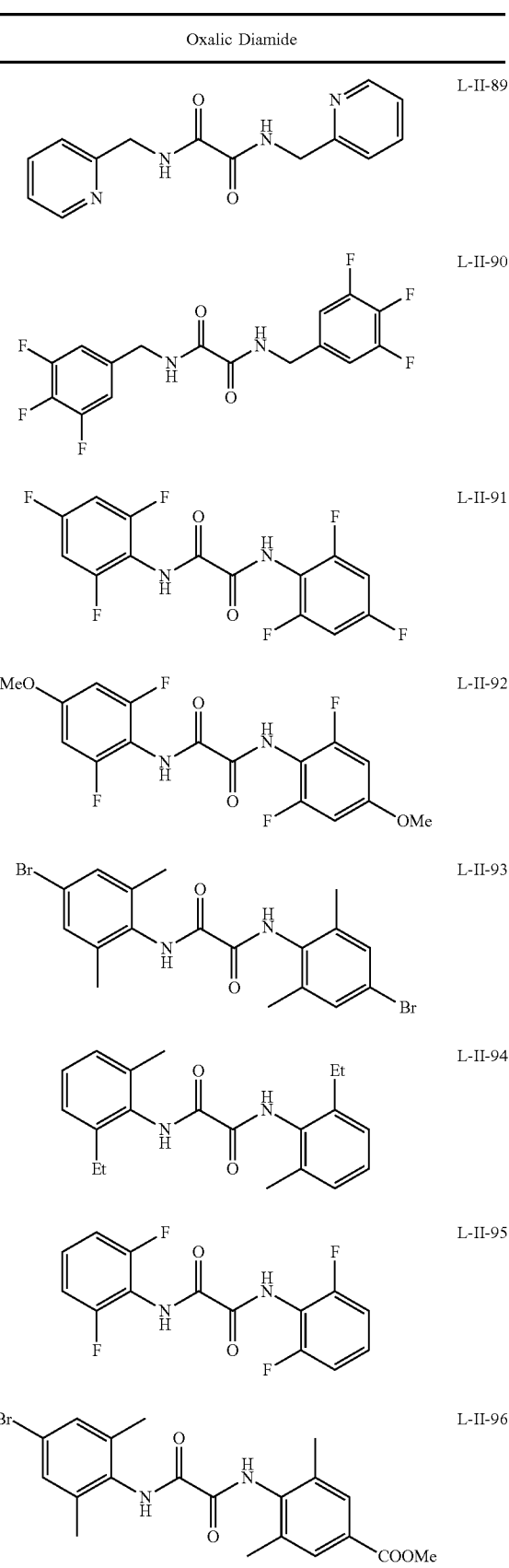

TABLE 2-continued

Oxalic Diamide

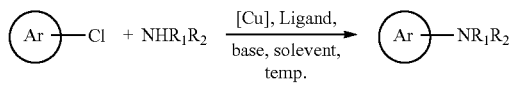

Each of the above ligands can be obtained commercially or can be prepared by the preferred method provided in the present invention.

It should be understood that the coupling reaction of aryl bromide and aryl iodide can occur more easily than that of aryl chloride under the same condition because the bond energies of C—Br and C—I bonds are lower than that of the C—Cl bond. Thus, in addition to the coupling reaction of aryl chloride, the above ligands are also applicable to the coupling reactions of aryl bromide and aryl iodide which are conventional in the art.

Copper-Catalyzed Coupling Reaction of Aryl Chloride

The present invention also provides a method for copper catalyzed coupling reaction of aryl chloride, which comprises carrying out the above reactions using a compound of formula (I) as described hereinabove as a ligand.

Generally, due to the high reactivity of aryl iodides and aryl bromides, the corresponding coupling reactions proceed well under the catalysis of transition metals such as palladium, copper and nickel. Aryl chlorides are cheaper and more readily available, and have more application prospects compared with aryl bromides (iodides). However, high energy of C—Cl bond makes the coupling reaction of aryl chlorides difficult to react under the conventional catalytic conditions of aryl bromides and aryl iodides.

The ligands and reaction conditions can be optimized for different reactants within the scope of the present disclosure so as to choose the most suitable ligand types and reaction conditions (e.g., temperature, solvent, reactant ratio, reaction time, etc.). The above optimization is within the skill of one in the art after reading the disclosure of the present application.

Several of the most preferred copper-catalyzed coupling reactions of aryl chloride are as follows:

1. Copper-Catalyzed C—N Coupling Reaction of Aryl Chloride Promoted by oxalic (Mono, bis) Amide Ligand In C—N coupling reaction, the selection of coupling reagent is not particularly limited, and may be the corresponding primary or secondary amines, or other ammonia sources such as ammonia, ammonium hydroxide or ammonium salt, sodium azide, N-containing heteroaromatic ring, etc. The specific reaction process is as follows:

In cases where the coupling reagent is a primary or secondary amine, the reaction is represented by the formula:

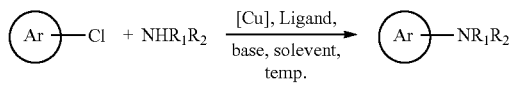

wherein the definition of each group is described as above,

is selected from the group consisting of substituted or unsubstituted C6-C20 aryl, substituted or unsubstituted 3- to 20-membered heteroaryl; wherein the substitution means that one or more hydrogen atoms on the aryl is substituted by a substituent selected from the group consisting of halogen, nitro, cyano, substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 acylamino (alkyl-NHC(O)—, aryl-NHC(O)—), —COOH, hydroxy-C1-C10 alkylene, MeS—, sulfuryl, and sulfonamido;

$R_1$, $R_2$ are each independently selected from the group consisting of H, substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group, or $R_1$ and $R_2$ together with the adjacent nitrogen atom to form a 3- to 20-membered ring (such as substituted or unsubstituted pyrrole, indole, azoles, benzoxazole and aromatic heterocycles), or $R_1$ is $R_cC(O)$—, wherein $R_c$ is selected from: H, substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, or substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure;

the substitution means that one or more hydrogen atoms on the group is substituted by a substituent selected from the group consisting of halogen, C1-C6 alkyl, C1-C6 alkoxy, C6-C10 aryl, C6-C10 aryl-oxy, C2-C10 ester group (alkyl-OOO—), C2-C10 acyl (alkyl-CO—), C2-C10 acylamino (alkyl-NHC(O)—, aryl-NHC(O)—), and —COOH.

In the above reaction process, the copper catalyst can be CuI, CuBr, CuCl, CuTc, Cu(OAc)$_2$, CuSO$_4$, Cu$_2$O, CuBr$_2$, CuCl$_2$, CuO, CuSCN, CuCN, or Cu(acac)$_2$, and preferably CuI.

The ligand is not specifically limited, and may be any one of the above ligands. It preferably is L-I-25, L-I-27, L-II-7, L-II-9, L-II-31, L-II-38, or L-II-64, and most preferably L-II-31, L-II-38 or L-II-64.

The preferred base may be potassium carbonate, cesium carbonate, potassium phosphate, sodium carbonate, sodium bicarbonate, potassium bicarbonate, preferably potassium phosphate, or cesium carbonate, and most preferably is potassium phosphate.

The solvent may be DMSO, DMF, DMA, NMP, acetonitrile, tert-butanol, isopropanol, THF, or 1,4-dioxane, and preferably is DMSO, or DMF, and most preferably DMSO.

The reaction temperature is at 50-180° C., and preferably 100-130° C.

In cases where the coupling reagents are other ammonia sources, the reaction is as follows:

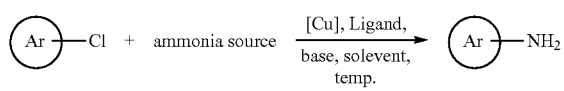

wherein the definition of each group is described as above,

is selected from the group consisting of substituted or unsubstituted C6-C20 aryl, and substituted or unsubstituted 3- to 20-membered heteroaryl; wherein the substitution means that one or more hydrogen atoms on the aryl is substituted by a substituent selected from the group consisting of halogen, nitro, cyano, substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-OOO—), C2-C10 acyl (alkyl-CO—, aryl-NHC (O)—), C2-C10 acylamino (alkyl-NHC(O)—), —COOH, hydroxy-C1-C10 alkylene, MeS—, sulfuryl, and sulfonamido;

the ammonia source is selected from the group consisting of ammonia, ammonium hydroxide, ammonium chloride, ammonium carbonate, ammonium bicarbonate, ammonium sulfate, ammonium nitrate, ammonium phosphate, diammonium hydrogen phosphate, sodium azide, preferably ammonia, ammonium hydroxide, ammonium chloride and diammonium hydrogen phosphate.

the copper catalyst may be CuI, CuBr, CuCl, CuTc, Cu(OAc)$_2$, CuSO$_4$, Cu$_2$O, CuBr$_2$, CuCl$_2$, CuO, CuSCN, CuCN, or Cu(acac)$_2$, and preferably CuI.

The ligand 1 (Ligand) can be any one of the above, and preferably L-I-27, L-II-9, L-II-38, L-II-64, L-II-71, L-II-72, and most preferably L-II-38 or L-II-71.

The base may be potassium carbonate, cesium carbonate, potassium phosphate, sodium carbonate, sodium bicarbonate, or potassium bicarbonate, and preferably cesium carbonate, or potassium phosphate, and most preferably potassium phosphate.

The solvent may be DMSO, DMF, DMA, NMP, acetonitrile, tert-butanol, isopropanol, THF, or 1,4-dioxane, and preferably DMSO, DMF, and most preferably DMSO.

The reaction temperature is at 50-180° C., and preferably 100-130° C.

In a preferred embodiment of the present invention, the coupling reaction of aryl chloride with the N-containing aromatic heterocycles is represented by the following formula:

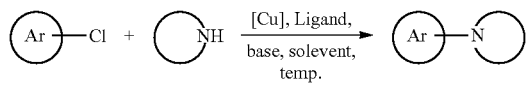

wherein the definition of each group is described as above,

is selected from the group consisting of substituted or unsubstituted C6-C20 aryl, and substituted or unsubstituted 3- to 20-membered heteroaryl; wherein the substitution means that one or more hydrogen atoms on the aryl is substituted by a substituent selected from the group consisting of halogen, nitro, cyano, substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 acylamino (alkyl-NHC(O)—, aryl-NHC(O)—), —COOH, hydroxy-C1-C10 alkylene, MeS—, sulfuryl, and sulfonamido;

C* is a substituted or unsubstituted 3- to 20-membered ring containing nitrogen atoms, the 3- to 20-membered ring can be saturated or unsaturated (preferably selected from the group consisting of pyrrole, indole, azoles, benzoxazole as well as the corresponding aromatic heterocycles with substituents);

In the above reaction process, the copper catalyst can be CuI, CuBr, CuCl, CuTc, Cu(OAc)$_2$, CuSO$_4$, Cu$_2$O, CuBr$_2$, CuCl$_2$, CuO, CuSCN, CuCN, or Cu(acac)$_2$, and preferably Cu$_2$O.

The ligand is not specifically limited, and may be any one of the above ligands, and preferably L-II-82.

The preferred base may be potassium carbonate, cesium carbonate, potassium phosphate, sodium carbonate, sodium bicarbonate, or potassium bicarbonate, and preferably potassium phosphate, cesium carbonate, and most preferably potassium phosphate.

The solvent can be DMSO, DMF, DMA, NMP, acetonitrile, tert-butanol, isopropanol, THF, or 1,4-dioxane, and preferably DMSO, DMF, and most preferably DMSO.

The reaction temperature is at 50-180° C., and preferably 100-130° C.

In a preferred embodiment of the present invention, the coupling reaction of aryl chloride with amide is represented by the following formula:

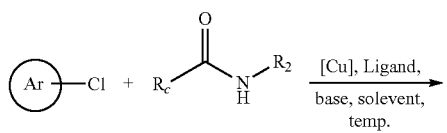

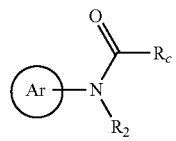

wherein the definition of each group is described as above,

is selected from the group consisting of substituted or unsubstituted C6-C20 aryl, and substituted or unsubstituted 3- to 20-membered heteroaryl; wherein the substitution means that one or more hydrogen atoms on the aryl is substituted by a substituent selected from the group consisting of halogen, nitro, cyano, substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 acylamino (alkyl-NHC(O)—, aryl-NHC(O)—), —COOH, hydroxy-C1-C10 alkylene, MeS—, sulfuryl, and sulfonamido;

each of 12, and $R_2$ is independently selected from the group consisting of H, substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O or S; the cycloalkyl or heterocyclic group may be a monocyclic, polycyclic, spiro or bridged ring structure;

or $R_c$ and $R_2$ together with adjacent C(O)NH, form a substituted or unsubstituted C3-C20 cycloalkyl, or substituted or unsubstituted 3- to 20-membered heterocyclic group;

the substitution means that one or more hydrogen atoms on the group is substituted by a substituent selected from the group consisting of halogen, C1-C6 alkyl, C1-C6 alkoxy, C6-C10 aryl, C6-C10 aryl-oxy, C2-C10 ester group (alkyl-OOO—), C2-C10 acyl (alkyl-CO—), C2-C10 acyl amino (alkyl-NHC(O)—, aryl-NHC(O)—), and —COOH.

In the above reaction process, the copper catalyst can be CuI, CuBr, CuCl, CuTc, Cu(OAc)$_2$, CuSO$_4$, Cu$_2$O, CuBr$_2$, CuCl$_2$, CuO, CuSCN, CuCN, or Cu(acac)$_2$, and preferably Cu$_2$O.

The ligand is not specifically limited, and may be any one of the above ligands, and preferably L-II-83, L-II-90.

The preferred base may be potassium carbonate, cesium carbonate, potassium phosphate, sodium carbonate, sodium bicarbonate, or potassium bicarbonate, and preferably potassium phosphate, or cesium carbonate, and most preferably potassium phosphate.

The solvent can be DMSO, DMF, DMA, NMP, acetonitrile, tert-butanol, isopropanol, THF, or 1,4-dioxane, and preferably DMSO, or DMF, and most preferably DMSO.

The reaction temperature is at 50-180° C., and preferably 100-130° C.

2. Copper-Catalyzed C—O Coupling Reaction of Aryl Chloride Promoted by Oxalic (Mono, Bis) Amide Ligand

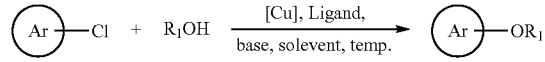

wherein the definition of each group is described as above,

is selected from the group consisting of substituted or unsubstituted C6-C20 aryl, or substituted or unsubstituted 3- to 20-membered heteroaryl; wherein the substitution means that one or more hydrogen atoms on the aryl is substituted by a substituent selected from the group consisting of halogen, nitro, cyano, substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 acyl amino (alkyl-NHC(O)—, aryl-NHC(O)—), —COOH, hydroxy-C1-C10 alkylene, MeS—, sulfuryl, and sulfonamido;

$R_1$ is selected from the group consisting of substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure;

the substitution means that one or more hydrogen atoms on the group is substituted by a substituent selected from the group consisting of halogen, C1-C6 alkyl, C1-C6 alkoxy, C6-C10 aryl, C6-C10 aryl-oxy, C2-C10 ester group (alkyl-OOO—), C2-C10 acyl (alkyl-CO—), C2-C10 acyl amino (alkyl-NHC(O)—, aryl-NHC(O)—), —COOH, —CN, MeS—, sulfuryl, and sulfonamido.

The copper catalyst can be CuI, CuBr, CuCl, CuTc, Cu(OAc)$_2$, CuSO$_4$, Cu$_2$O, CuBr$_2$, CuCl$_2$, CuO, CuSCN, CuCN, or Cu(acac)$_2$, and preferably CuI.

The ligand is any one of 1, and preferably L-II-34.

The base can be potassium carbonate, cesium carbonate, potassium phosphate, sodium carbonate, sodium bicarbonate, or potassium bicarbonate, and preferably potassium phosphate.

The solvent can be DMSO, DMF, DMA, NMP, acetonitrile, tert-butanol, isopropanol, THF, or 1,4-dioxane, and preferably DMSO.

The reaction temperature is at 50-180° C., and preferably 100-130° C.

3. Copper-Catalyzed C—S Coupling Reaction of Aryl Chloride Promoted by Oxalic (Mono, Bis) Amide Ligand

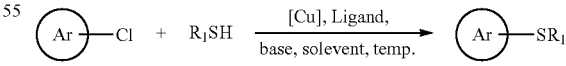

wherein the definitinn of each group is described as above,

is selected from the group consisting of substituted or unsubstituted C6-C20 aryl, and substituted or unsubstituted 3- to 20-membered heteroaryl; wherein the substitution means that one or more hydrogen atoms on the aryl is substituted by a substituent selected from the group consisting of halogen, nitro, cyano, substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 acyl amino(alkyl-NHC(O)—, aryl-NHC(O)—), —COOH, hydroxy-C1-C10 alkylene, MeS—, sulfuryl, and sulfonamido;

$R_1$ is selected from the group consisting of substituted or unsubstituted C1-C6 alkyl, substituted or unsubstituted C6-C20 aryl, substituted or unsubstituted 3- to 20-membered heteroaryl, substituted or unsubstituted C7-C25 alkylaryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure;

the substitution means that one or more hydrogen atoms on the group is substituted by a substituent selected from the group consisting of halogen, C1-C6 alkyl, C1-C6 alkoxy, C6-C10 aryl, C6-C10 aryl-oxy, C2-C10 ester group (alkyl-OOO—), C2-C10 acyl (alkyl-CO—), C2-C10 acyl amino (alkyl-NHC(O)—, aryl-NHC(O)—), —COOH, —CN, MeS—, sulfuryl, and sulfonamido.

The copper catalyst can be CuI, CuBr, CuCl, CuTc, $Cu(OAc)_2$, $CuSO_4$, $Cu_2O$, $CuBr_2$, $CuCl_2$, CuO, CuSCN, CuCN, and $Cu(acac)_2$, and preferably CuI.

The ligand is any one of 1, and preferably L-II-34.

The base can be potassium carbonate, cesium carbonate, potassium phosphate, sodium carbonate, sodium bicarbonate, or potassium bicarbonate, and preferably potassium phosphate.

The solvent can be DMSO, DMF, DMA, NMP, acetonitrile, tert-butanol, isopropanol, THF, or 1,4-dioxane, and preferably DMSO.

The reaction temperature is at 50-180° C., and preferably 100-130° C.

4. Copper-Catalyzed C—S Coupling Reaction of Aryl Chloride Promoted by Oxalic (Mono, Bis) Amide Ligand

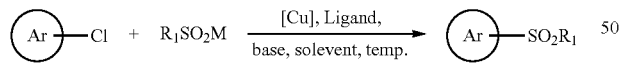

wherein the definition of each group is described as above,

is selected from the group consisting of substituted or unsubstituted C6-C20 aryl, and substituted or unsubstituted 3- to 20-membered heteroaryl; wherein the substitution means that one or more hydrogen atoms on the aryl is substituted by a substituent selected from the group consisting of halogen, nitro, cyano, substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-OOO—), C2-C10 acyl (alkyl-CO—), C2-C10 acyl amino(alkyl-NHC(O)—, aryl-NHC(O)—), —COOH, hydroxy-C1-C10 alkylene, MeS—, sulfuryl, and sulfonamido;

$R_1$ is selected from the group consisting of substituted or unsubstituted C1-C6 alkyl, substituted or unsubstituted C6-C20 aryl, substituted or unsubstituted 3- to 20-membered heteroaryl, substituted or unsubstituted C7-C25 alkylaryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure;

the substitution means that one or more hydrogen atoms on the group is substituted by a substituent selected from the group consisting of halogen, C1-C6 alkyl, C1-C6 alkoxy, C6-C10 aryl, C6-C10 aryl-oxy, C2-C10 ester group (alkyl-OOO—), C2-C10 acyl (alkyl-CO—), C2-C10 acyl amino (alkyl-NHC(O)—, aryl-NHC(O)—), —COOH, —CN, MeS—, sulfuryl, and sulfonamido.

The copper catalyst can be CuI, CuBr, CuCl, CuTc, $Cu(OAc)_2$, $CuSO_4$, $Cu_2O$, $CuBr_2$, $CuCl_2$, CuO, CuSCN, CuCN, or $Cu(acac)_2$, and preferably CuI.

The ligand is any one of 1, preferably L-II-3, L-II-37.

The base can be potassium carbonate, cesium carbonate, potassium phosphate, sodium carbonate, sodium bicarbonate, or potassium bicarbonate, and preferably potassium phosphate.

The solvent can be DMSO, DMF, DMA, NMP, acetonitrile, tert-butanol, isopropanol, THF, or 1,4-dioxane, and preferably DMSO.

The reaction temperature is at 50-180° C., and preferably 100-130° C.

5. Copper-Catalyzed C—O Coupling Reaction of Aryl Chloride Promoted by Oxalic (Mono, Bis) Amide Ligand

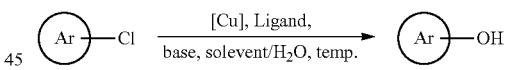

wherein the definition of each group is described as above,

is selected from the group consisting of substituted or unsubstituted C6-C20 aryl, and substituted or unsubstituted 3- to 20-membered heteroaryl; wherein the substitution means that one or more hydrogen atoms on the aryl is substituted by a substituent selected from the group consisting of halogen, nitro, cyano, substituted or unsubstituted amino, hydroxy, unsubstituted or halogenated C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 acyl amino (alkyl-NHC(O)—, aryl-NHC(O)—), —COOH, hydroxy-C1-C10 alkylene, MeS—, sulfuryl, and sulfonamido;

the substitution means that one or more hydrogen atoms on the group is substituted by a substituent selected from the group consisting of halogen, C1-C6 alkyl, C1-C6 alkoxy, C6-C10 aryl, C6-C10 aryl-oxy, C2-C10 ester group (alkyl-OOO—), C2-C10 acyl (alkyl-CO—), C2-C10 acyl amino (alkyl-NHC(O)—, aryl-NHC(O)—), —COOH, —CN, MeS—, sulfuryl, and sulfonamido.

The copper catalyst can be CuI, CuBr, CuCl, CuTc, Cu(OAc)$_2$, CuSO$_4$, Cu$_2$O, CuBr$_2$, CuCl$_2$, CuO, CuSCN, CuCN, or Cu(acac)$_2$, and preferably Cu(acac)$_2$.

The ligand is any one of 1, and preferably L-II-65, or L-II-93.

The base can be potassium carbonate, cesium carbonate, potassium phosphate, sodium carbonate, sodium bicarbonate, potassium bicarbonate, lithium hydroxide, sodium hydroxide, tetrabutyl ammonium hydroxide, and/or a hydrate of the base, and preferably lithium hydroxide.

The solvent can be DMSO, DMF, DMA, NMP, acetonitrile, tert-butanol, isopropanol, THF, 1,4-dioxane, tert-butanol, and/or a mixture of one or more of the foregoing solvents and water, preferably DMSO/H$_2$O.

The reaction temperature is at 50-180° C., and preferably 100-130° C.

Compared with the Prior Art, the Main Advantages of the Present Invention Include:

1. It provides a class of catalytic systems capable of carrying out copper-catalyzed coupling reaction of aryl chloride with high efficiency. The catalytic system can make the coupling reaction of aryl chloride proceed successfully which is difficult to be carried out in common coupling conditions for aryl bromide and aryl iodide. Further, the coupling reaction has good compatibility with substrates and wide scope of application.

2. Compared with the coupling reaction method of aryl chloride in the prior art, the method of the present invention uses the copper catalytic system which is of lower cost. Moreover, the ligand has a simple structure, can be easily prepared, has a low catalytic loading, thus making the reaction more economical.

3. The aryl chlorides used in the catalytic system of the present invention have lower cost and wider sources than other aryl halides, and have good prospect in large-scale application.

The present invention will be further illustrated below with reference to the specific examples. It should be understood that these examples are only to illustrate the invention but not to limit the disclosure of the invention. The experimental methods without specific conditions in the following embodiments are generally carried out according to conventional conditions, or in accordance with the conditions recommended by the manufacturer. Unless indicated otherwise, parts and percentage are calculated by weight.

Example 1. Synthesis of Ligands (L-I-27, L-II-9, L-II-31 as Examples)

Process i:

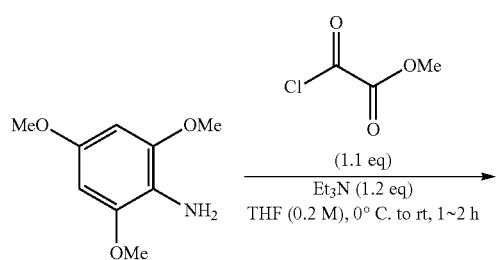

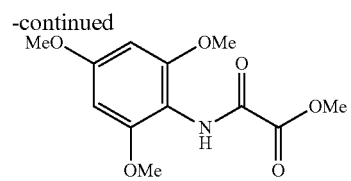

2,4,6-Trimethoxyaniline (30 mmol) and triethylamine (36 mmol) were dissolved in 150 mL of tetrahydrofuran, and the concentration of 2,4,6-trimethoxyaniline was 0.2 mol/L. The mixture was cooled in an ice-water bath, and stirred. Then oxalyl chloride monomethyl ester (33 mmol) was added dropwise, the system became cloudy and triethylamine hydrochloride was produced. After the addition was completed, ice water bath was removed, and mixture was naturally restored to room temperature, and stirring was continued for 1 to 2 hours until 2,4,6-trimethoxyaniline was completely consumed (monitored by TLC).

Then the reaction mixture was filtered and triethylamine hydrochloride was removed. The filter cake was rinsed with a small amount of tetrahydrofuran (Do not flush with ethyl acetate, otherwise triethylamine hydrochloride will be dissolved). After the filtrate was concentrated, the residue was purified by silica gel chromatography using petroleum ether: ethyl acetate=5:1 as eluent to give a light yellow solid (7.48 g, 93% yield).

Oxalyl chloride monomethyl ester was replaced by oxalyl chloride monoethyl ester when oxalic monoamide monoethyl ester was prepared.

$^1$H NMR (400 MHz, CDCl$_3$) δ 8.12 (s, 1H), 6.16 (s, 2H), 3.94 (s, 3H), 3.81 (s, 9H); $^{13}$C NMR (100 MHz, CDCl$_3$) δ 161.49, 160.64, 156.07, 154.55, 105.72, 91.18, 56.10, 55.66, 53.73; HRMS (ESI) calcd. for C$_{12}$H$_{16}$NO$_6$ (M+H)$^+$: 270.0972, Found: 270.0973.

Process ii:

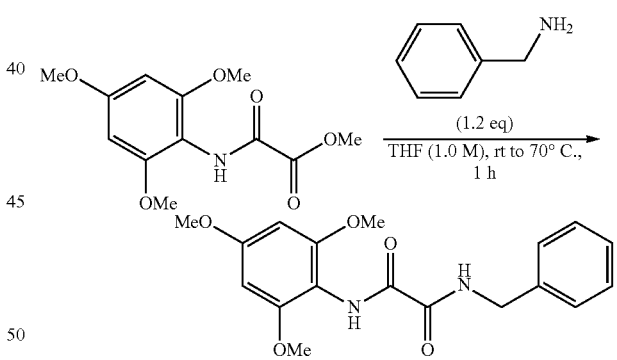

The oxalate monomethyl ester (10 mmol) obtained above was dissolved in 10 mL of THF, and the substrate concentration was 1.0 mol/L. 1.3 mL of benzylamine (12 mmol) was then added. The mixture was heated to 70-80° C. and stirred until the raw materials disappeared (monitored by TLC after 1 hr). The heater was removed and the mixture in reaction flask was stood to cool to room temperature in the air, and then frozen in refrigerator. The product was precipitated out as a white solid. Then the mixture was filtered under reduced pressure with filter paper, dried in an infrared oven, and dried with an oil pump to produce a white solid (2.94 g, 86% yield).

Benzylamine was replaced by other aliphatic amines (such as methylamine solution, diethylamine, etc.) to afford other amides.

¹H NMR (400 MHz, CDCl₃) δ 3.80 (s, 6H), 3.81 (s, 3H), 4.53 (d, J=6.4 Hz, 2H), 6.16 (s, 2H), 7.30-7.38 (m, 5H), 7.79 (br s, 1H), 8.51 (s, 1H); ¹³C NMR (100 MHz, CDCl₃) δ 160.40, 159.95, 158.24, 156.03, 136.92, 128.80, 128.03, 127.83, 105.69, 90.96, 55.96, 55.53, 43.86; HRMS (ESI) calcd. for $C_{18}H_{21}N_2O_5$ (M+H)⁺: 345.1445, Found: 345.1444.

Process II:

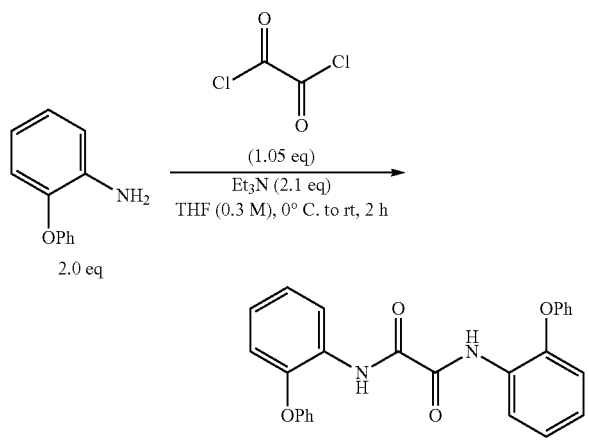

2-Phenoxyaniline (30 mmol) and triethylamine (31.5 mmol) were dissolved in 100 mL of tetrahydrofuran, and the concentration of 2-phenoxyaniline was 0.3 mol/L. The mixture was cooled in an ice-water bath, and stirred. Then oxalyl chloride (15.8 mmol) was added dropwise. The system turned to turbid and triethylamide hydrochloride was formed. The ice-water bath was then removed and the mixture was warmed to room temperature in the air, and continuously stirred for 2 hours until 2-phenoxyaniline was completely consumed (monitored by TLC). Then the stirring was stopped for post process.

The stirring bar was removed by a magnetic bar, and tetrahydrofuran was removed by evaporation under reduced pressure. 50 mL of distilled water was added to the resultant residue. The solid on the flask wall was scraped off and immersed into distilled water, and stirred to form slurry. Et₃N.HCl was completely dissolved in water while the oxalic diamide was left undissolved. Then the slurry was filtered under reduced pressure, and the solid on filter paper was washed with cold diethyl ether. The residue was removed and dried in an infrared oven, and then dried with an oil pump to afford a white solid (5.45 g, 86% yield).

¹H NMR (400 MHz, CDCl₃) δ 9.96 (s, 2H), 8.46 (dd, J=8.0, 1.7 Hz, 2H), 7.43-7.30 (m, 4H), 7.22-7.01 (m, 10H), 6.89 (dd, J=8.0, 1.5 Hz, 2H); ¹³C NMR (100 MHz, CDCl₃) δ 157.36, 156.06, 146.73, 129.97, 127.97, 125.40, 124.18, 123.75, 120.49, 119.02, 117.60; HRMS (ESI) calcd. for $C_{26}H_{21}N_2O_4$ (M+H)⁺: 425.1496, Found: 425.1492.

Synthesis of Other Ligands (New Compounds):

| ligand (new compound) | Characterization Data |
| --- | --- |
| L-I-5, process i, yield 91% | ¹H NMR (400 MHz, CDCl₃) δ 9.17 (s, 1H), 8.33 (d, J = 8.3 Hz, 1H), 7.95 (d, J = 8.3 Hz, 1H), 7.82 (d, J = 8.5 Hz, 1H), 7.64-7.57 (m, 1H), 7.57-7.51 (m, 1H), 6.84 (d, J = 8.5 Hz, 1H), 4.03 (s, 3H), 4.02 (s, 3H); ¹³C NMR (100 MHz, CDCl₃) δ 161.94, 154.52, 154.30, 127.90, 127.45, 126.00, 125.80, 123.59, 123.09, 121.20, 120.26, 103.41, 55.85, 54.19; HRMS (ESI) calcd. for $C_{14}H_{14}NO_4$ (M + H)⁺: 260.0923, found: 260.0917. |
| L-I-11, process i, yield 79% | ¹H NMR (400 MHz, CDCl₃) δ 8.27 (s, 1H), 7.19 (t, J = 8.4 Hz, 1H), 6.57 (d, J = 8.5 Hz, 2H), 3.91 (s, 3H), 3.80 (s, 6H); ¹³C NMR (100 MHz, CDCl₃) δ 161.20, 155.07, 153.99, 128.45, 112.35, 104.31, 55.97, 53.62: LC-MS (ESI, m/z): 240.1 (M + H)⁺. |
| L-I-15, process i, yield 85% | ¹H NMR (400 MHz, d6-DMSO) δ 10.51 (s, 1H), 7.80 (d, J = 7.2 Hz, 2H), 7.62 (s, 2H), 7.52-7.34 (m, 13H), 3.65 (s, 3H); ¹³C NMR (100 MHz, CDCl₃) δ 160.73, 155.01, 141.44, 141.02 (2C), 140.00, 139.16 (2C), 129.01 (2C), 128.91 (2C), 128.75 (4C), 128.62 (4C), 127.95 (2C), 127.88 (2C), 127.36 (2C), 53.75; HRMS-ESI: m/z calcd for $C_{27}H_{22}O_3N$ (M + H)⁺: 408.1594, found: 408.1592. |

-continued

| ligand (new compound) | Characterization Data |
|---|---|
| 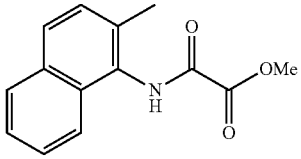<br>L-I-16<br>process i, yield 55% | $^1$H NMR (400 MHz, CDCl$_3$) δ 8.81 (s, 1H), 7.84 (d, J = 8.8 Hz, 1H), 7.81 (d, J = 8.4 Hz, 1H), 7.78 (d, J = 8.4 Hz, 1H), 7.54-7.50 (m, 1H), 7.49-7.45 (m, 1H), 7.39 (d, J = 8.4 Hz, 1H), 4.04 (s, 3H), 2.43 (s, 3H); $^{13}$C NMR (100 MHz, CDCl$_3$) δ 161.27, 154.93, 133.07, 132.55, 129.64, 128.65, 128.15 (2C), 127.85, 126.79, 125.46, 121.73, 53.84, 18.62; HRMS-ESI: m/z calcd for C$_{14}$H$_{14}$O$_3$N (M + H)$^+$: 244.0968, found: 244.0968. |
| 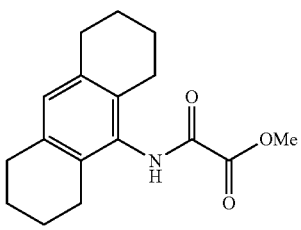<br>L-I-18<br>process i, yield 89% | $^1$H NMR (400 MHz, CDCl$_3$) δ 8.23 (s, 1H), 6.85 (s, 1H), 3.97 (s, 3H), 2.72 (m, 4H), 2.56 (m, 4H), 1.76-1.74 (m, 8H); $^{13}$C NMR (100 MHz, CDCl$_3$) δ 161.53, 154.50, 135.39, 131.40 (4C), 130.10, 53.93, 29.39 (2C), 25.27 (2C), 23.00 (2C), 22.83 (2C); HRMS-ESI: m/z calcd for C$_{17}$H$_{22}$O$_3$N (M + H)$^+$: 288.1594, found: 288.1594. |
| 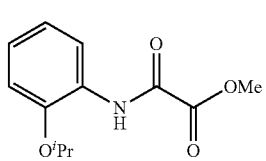<br>L-I-26<br>process i, yield 84% | $^1$H NMR (500 MHz, CDCl$_3$) δ 1.40 (d, J = 7.5 Hz, 6H), 3.97 (s, 3H), 4.62 (hept, 1H), 6.91-6.70 (m, 2H), 7.07-7.12 (m, 1H), 8.39-8.43 (m, 1H), 9.59 (brs, 1H); $^{13}$C NMR (100 MHz, CDCl$_3$) δ 161.34, 153.18, 146.66, 127.00, 125.13, 120.94, 119.86, 112.84, 71.61, 53.78, 21.99; HRMS-ESI: m/z calcd for C$_{12}$H$_{16}$NO$_4$ (M + H)$^+$: 238.1074, found: 238.1079. |
| 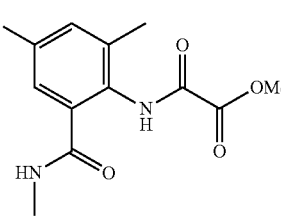<br>L-I-33<br>process i, yield 87% | $^1$H NMR (400 MHz, CDCl$_3$) δ 10.35 (s, 1H), 7.32 (s, 1H), 7.26 (s, 1H), 6.39 (br s, 1H), 3.96 (s, 3H), 2.93-2.90 (m, 3H), 2.24 (s, 3H): $^{13}$C NMR (100 MHz, d6-DMSO) δ 166.24, 160.60, 154.96, 138.21, 134.52, 131.71, 131.58, 130.87, 125.51, 53.27, 26.18, 18.07; HRMS-ESI: m/z calcd for C$_{12}$H$_{14}$O$_4$N$_2$Cl (M + H)$^+$: 285.0637, found: 285.0639. |
| 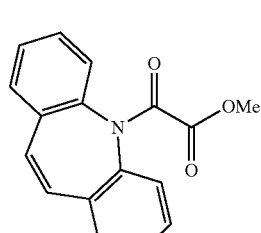<br>L-I-35<br>process i, yield 63% | $^1$H NMR (400 MHz, CDCl$_3$) δ 7.51 (m, 2H), 7.38-7.33 (m, 6H), 6.96 (s, 2H), 3.52 (s, 3H): $^{13}$C NMR (100 MHz, CDCl$_3$) δ 162.46, 161.52, 137.79, 137.23, 135.10, 133.31, 130.93, 129.76, 129.63, 129.42, 129.35, 129.04, 128.71, 128.14, 127.60, 126.93, 52.22: HRMS-ESI: m/z calcd for C$_{17}$H$_{14}$O$_3$N (M + H)$^+$: 280.0968, found: 280.0968. |
| 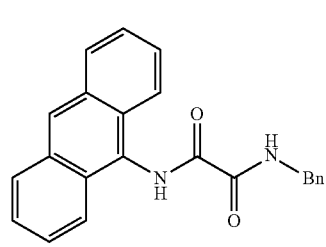<br>L-II-3<br>process ii, yield 87% | $^1$H NMR (400 MHz, CDCl$_3$) δ 4.66 (d, J = 6.0 Hz, 2H), 7.35-7.42 (m, 5H), 7.48-7.58 (m, 4H), 7.92 (br s, 1H), 8.00-8.07 (m, 4H), 8.51 (s, 1H), 9.63 (s, 1H); $^{13}$C NMR (100 MHz, d6-DMSO) δ 160.61, 160.09, 138.75, 131.18, 128.55, 128.38, 127.76, 127.59, 127.01, 126.35, 126.27, 125.59, 123.59, 42.65: HRMS-ESI: m/z calcd for C$_{23}$H$_{19}$N$_2$O$_2$ (M + H)$^+$: 355.1441, found: 355.1446. |

-continued

| ligand (new compound) | Characterization Data |
|---|---|
| 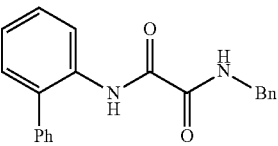<br>L-II-4<br>process ii, yield 82% | $^1$H NMR (400 MHz, CDCl$_3$) δ 9.55 (s, 1H), 8.43 (dd, J = 8.2, 0.9 Hz, 1H), 7.88 (s, 1H), 7.56-7.49 (m, 2H), 7.47-7.37 (m, 4H), 7.37-7.22 (m, 7H), 4.48 (d, J = 6.2 Hz, 1H); $^{13}$C NMR (100 MHz, CDCl$_3$) δ 159.75, 157.19, 137.25, 136.66, 133.40, 132.89, 130.37, 129.24, 129.16, 128.81, 128.45, 128.35, 127.88, 127.80, 125.21, 120.24, 43.88; LC-MS (ESI, m/z): 331.0 (M + H)$^+$. |
| 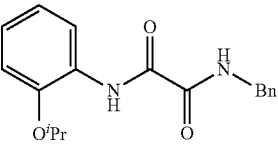<br>L-II-6<br>process ii, yield 79% | $^1$H NMR (400 MHz, CDCl$_3$) δ 1.41 (d, J = 6.0 Hz, 6H), 4.56 (d, J = 6.4 Hz, 2H), 4.62 (hept, 1H), 6.92-6.99 (m, 2H), 7.07-7.12 (m, 1H), 7.30-7.38 (m, 5H), 7.86 (br s, 1H), 8.36 (dd, J = 8.0, 1.6 Hz, 1H), 9.97 (s, 1H); $^{13}$C NMR (100 MHz, CDCl$_3$) δ 160.06, 157.11, 147.12, 136.86, 128.87, 127.90, 127.85. 127.16, 125.07, 120.90, 119.77, 113.04, 71.64, 43.94, 22.11: HRMS-ESI: m/z calcd for C$_{18}$H$_{21}$N$_2$O$_3$ (M + H)$^+$: 313.1547, found: 313.1550. |
| 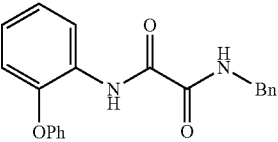<br>L-II-7<br>process ii, yield 86% | $^1$H NMR (400 MHz, CDCl$_3$) δ 9.91 (s, 1H), 8.43 (dd, J = 7.9, 1.6 Hz, 1H), 7.91 (s, 1H), 7.43-7.26 (m, 7H), 7.19-7.00 (m, 5H), 6.88 (dd, J = 8.0, 1.3 Hz, 1H), 4.53 (d, J = 6.2 Hz, 1H); $^{13}$C NMR (100 MHz, CDCl$_3$) δ 159.67, 157.40, 156.07, 146.73, 136.74, 129.94, 128.83, 128.00, 127.89, 127.85, 125.30, 124.13, 123.70, 120.55, 119.00, 117.63, 43.96: LC-MS (ESI, m/z): 347.0 (M + H)$^+$. |
| 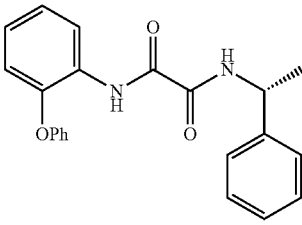<br>L-II-10<br>process ii, yield 78% | $^1$H NMR (400 MHz, CDCl$_3$) δ 9.88 (s, 1H), 8.43 (dd, J = 8.0, 1.6 Hz, 1H), 7.80 (d, J = 8.0 Hz, 1H), 7.43-7.22 (m, 6H), 7.18-6.98 (m, 5H), 6.87 (dd, J = 8.1, 1.4 Hz, 1H), 5.16-4.99 (m, 1H), 1.58 (d, J = 6.9 Hz, 3H): $^{13}$C NMR (100 MHz, CDCl$_3$) δ 158.83, 157.48, 156.04, 146.70, 141.91, 129.91, 128.80, 128.02, 127.75, 126.14, 125.24, 124.10, 123.67, 120.46, 118.98, 117.58, 49.77, 21.63: LC-MS (ESI, m/z): 383.0 (M + Na)$^+$. |
| 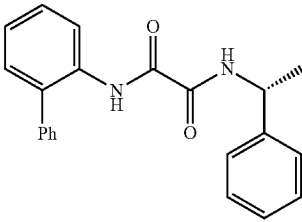<br>L-II-11<br>process ii, yield 82% | $^1$H NMR (400 MHz, CDCl$_3$) δ 9.56 (s, 1H), 8.46 (dd, J = 8.2, 0.7 Hz, 1H), 7.87 (d, J = 8.1 Hz, 1H), 7.56-7.45 (m, 2H), 7.46-7.20 (m, 10H), 5.06 (dq, J = 14.2, 7.0 Hz, 1H), 1.55 (d, J = 7.0 Hz, 3H); $^{13}$C NMR (100 MHz, CDCl$_3$) δ 158.92, 157.35, 141.94, 137.27, 133.46, 132.87, 130.40, 129.24, 129.15, 128.79, 128.45, 128.33, 127.72, 126.11, 125.18, 120.21, 49.64, 21.76: LC-MS (ESI, m/z): 367.0 (M + Na)$^+$. |
| 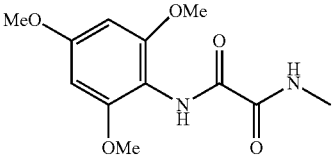 [SMILES: CNC(=O)C(=O)Nc1c(OC)cc(OC)cc1OC]<br>L-II-13<br>process ii, yield 91% | $^1$H NMR (400 MHz, CDCl$_3$) δ 2.94 (d, J = 5.2 Hz, 3H), 3.78 (s, 6H), 3.81 (s, 3H), 6.16 (s, 2H), 7.49 (br s, 1H), 8.48 (s, 1H): $^{13}$C NMR (100 MHz, CDCl$_3$) δ 160.69, 160.38, 158.36, 156.04, 105.67, 90.94, 55.94, 55.52, 26.21; HRMS (DART) calcd. for C$_{12}$H$_{17}$N$_2$O$_5$ (M + H)$^+$: 269.1132, Found: 269.1131. |

-continued

| ligand (new compound) | Characterization Data |
|---|---|
| 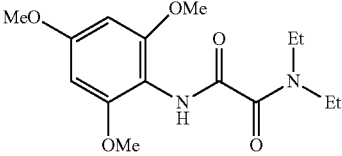 [SMILES: CCN(CC)C(=O)C(=O)Nc1c(OC)cc(OC)cc1OC]<br>L-II-14<br>process ii, yield 79% | $^1$H NMR (400 MHz, CDCl$_3$) δ 1.22 (t, J = 6.8 Hz, 3H), 1.28 (t, J = 6.8 Hz, 3H), 3.46 (a, J = 7.2 Hz, 2H), 3.76-3.83 (m, 11H), 6.16 (s, 2H), 8.25 (s, 1H); $^{13}$C NMR (100 MHz, CDCl$_3$) δ 162.21, 160.19, 160.09, 155.99, 106.12, 90.93, 55.91, 55.47, 43.31, 41.79, 14.69, 12.54; HRMS-ESI: m/z calcd for C$_{15}$H$_{23}$N$_2$O$_5$ (M + H)$^+$: 311.1601, found: 311.1610. |
| 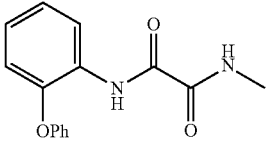 [SMILES: CNC(=O)C(=O)Nc1ccccc1Oc1ccccc1]<br>L-II-15<br>process ii, yield 83% | $^1$H NMR (400 MHz, CDCl$_3$) δ 2.94 (d, J = 5.2 Hz, 3H), 6.87-6.90 (m, 1H), 7.03-7.16 (m, 5H), 7.32-7.37 (m, 2H), 7.74 (br s, 1H), 8.41-8.44 (m, 1H), 9.89 (s, 1H); $^{13}$C NMR (100 MHz, CDCl$_3$) δ 160.43, 157.57, 156.16, 146.76, 129.98, 128.11, 125.32, 124.13, 123.75, 120.63, 118.95, 117.80, 26.44; HRMS-ESI: m/z calcd for C$_{15}$H$_{15}$N$_2$O$_3$ (M + H)$^+$: 271.1077, found: 271.1082. |
| 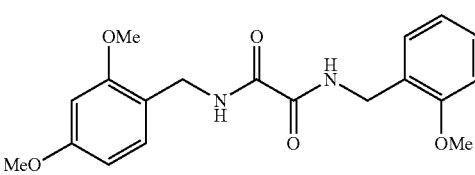<br>L-II-20<br>process II, yield 74% | $^1$H NMR (400 MHz, CDCl$_3$) δ 7.84 (s, 2H), 7.15 (d, J = 8.2 Hz, 2H), 6.44 (d, J = 2.4 Hz, 2H), 6.42 (d, J = 2.4 Hz, 1H), 6.40 (d, J = 2.4 Hz, 1H), 4.38 (d, J= 6.2 Hz, 4H), 3.82 (s, 6H), 3.79 (s, 6H); $^{13}$C NMR (100 MHz, CDCl$_3$) δ 160.92, 159.66, 158.76, 130.59, 117.72, 104.01, 98.71, 55.54, 55.50, 39.33; HRMS-ESI: m/z calcd for C$_{20}$H$_{25}$N$_2$O$_6$ (M + H)$^+$: 389.1713, found: 389.1707. |
| 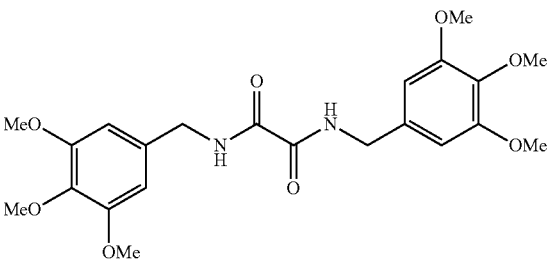<br>L-II-21<br>process II, yield 69% | $^1$H NMR (400 MHz, CDCl$_3$) δ 7.78 (t, J = 6.1 Hz, 2H), 6.50 (s, 4H), 4.42 (d, J = 6.1 Hz, 4H), 3.84 (s, 12H), 3.82 (s, 6H); $^{13}$C NMR (100 MHz, CDCl$_3$) δ 159.66, 153.64, 137.82, 132.46, 105.18, 60.98, 56.30, 44.29; HRMS-ESI: m/z calcd for C$_{22}$H$_{29}$N$_2$O$_8$ (M + H)$^+$: 449.1924, found: 449.1915. |
| 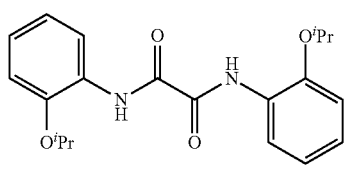 [SMILES: CC(C)Oc1ccccc1NC(=O)C(=O)Nc1ccccc1OC(C)C]<br>L-II-32<br>process II, yield 81% | $^1$H NMR (400 MHz, CDCl$_3$) δ 1.43 (d, J = 6.0 Hz, 12H), 4.63 (hept, 2H), 6.93-7.02 (m, 4H), 7.08-7.14 (m, 2H), 8.42-8.45 (m, 2H), 10.04 (s, 2H); $^{13}$C NMR (100 MHz, CDCl$_3$) δ 157.46, 147.17, 127.23, 125.13, 120.94, 119.80, 113.12, 71.73, 22.14; HRMS-ESI: m/z calcd for C$_{20}$H$_{25}$N$_2$O$_4$ (M + H)$^+$: 357.1809, found: 357.1813. |
| 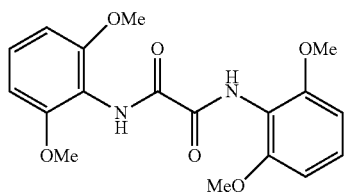 [SMILES: COc1cccc(OC)c1NC(=O)C(=O)Nc1c(OC)cccc1OC]<br>L-II-33<br>process II, yield 92% | $^1$H NMR (400 MHz, CDCl$_3$) δ 8.71 (s, 2H), 7.22 (t, J = 8.4 Hz, 2H), 6.61 (d, J = 8.5 Hz, 4H), 3.84 (s, 12H); $^{13}$C NMR (100 MHz, CDCl$_3$) δ 157.97, 155.18, 128.14, 112.84, 104.29, 56.01; LC-MS (ESI, m/z): 361.0 (M + H)$^+$. |

| ligand (new compound) | Characterization Data |
|---|---|
| 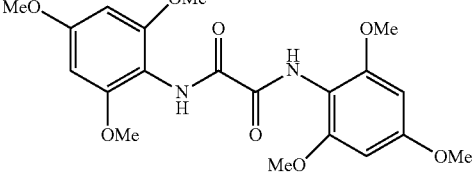<br>L-II-38<br>process II, yield 93% | $^1$H NMR (400 MHz, DMSO-$d_6$) δ 9.33 (s, 2H), 6.29 (s, 4H), 3.80 (s, 6H), 3.75 (s, 12H); $^{13}$C NMR (100 MHz, DMSO-$d_6$) δ 159.7, 158.9, 156.3, 106.3, 91.0, 55.7, 55.4; HRMS-ESI: m/z calcd for $C_{20}H_{25}N_2O_8$ (M + H)$^+$: 421.1605, found: 421.1607. |
| L-II-39<br>process ii, yield 50% | $^1$H NMR (400 MHz, CDCl$_3$) δ 9.25 (s, 1H), 7.92 (s, 1H), 7.85-7.82 (m, 2H), 7.78-7.76 (d, J = 8.4 Hz, 1H), 7.54-7.49 (m, 1H), 7.48-7.44 (m, 1H), 7.40-7.33 (m, 6H), 4.60-4.58 (d, J = 6 Hz, 2H), 2.42 (s, 3H); $^{13}$C NMR (100 MHz, d6-DMSO) δ 160.13, 159.69, 138.79, 132.65, 132.25, 130.44, 130.13, 128.64, 128.40 (2C), 127.86, 127.59 (2C), 127.14, 127.04, 126.40, 125.31, 122.91, 42.66, 18.23: HRMS-ESI: m/z calcd for $C_{20}H_{19}O_2N_2$ (M + H)$^+$: 319.1441, found: 319.1440. |
| L-II-43<br>process ii, yield 60% | $^1$H NMR (400 MHz, CDCl$_3$) δ 9.83 (s, 1H), 8.71 (d, J = 9.1 Hz, 1H), 8.29 (dd, J = 9.1, 2.7 Hz, 1H), 8.22 (d, J = 2.7 Hz, 1H), 7.74 (s, 1H), 7.65-7.46 (m, 3H), 7.46-7.38 (m, 2H), 7.38-7.27 (m, 5H), 4.49 (d, J = 6.1 Hz, 2H); $^{13}$C NMR (125 MHz, CDCl$_3$) δ 158.98, 157.62, 144.04, 139.11, 136.28, 134.93, 133.20, 129.77, 129.50, 128.98, 128.91, 128.09, 127.83, 125.68, 124.12, 119.69, 44.05: HRMS (DART): m/z calcd for $C_{21}H_{18}O_4N_3$ (M + H)$^+$: 376.1292, found: 376.1290. |
| L-II-44<br>process ii, yield 72% | $^1$H NMR (400 MHz, CDCl$_3$) δ 9.50 (s, 1H), 8.37 (dd, J = 8.9, 5.3 Hz, 1H), 8.00 (t, J = 6.1 Hz, 1H), 7.60-7.44 (m, 3H), 7.43-7.22 (m, 7H), 7.15-7.00 (m, 2H), 4.48 (d, J = 6.2 Hz, 2H): $^{13}$C NMR (100 MHz, CDCl$_3$) δ 159.76, 159.66 (d, J = 245.8 Hz), 157.26, 136.77, 136.36, 135.11 (d, J = 7.5 Hz), 129.67 (d, J = 2.9 Hz), 129.46, 129.03, 128.89, 127.97, 127.86, 122.23 (d, J = 8.2 Hz), 117.17 (d, J = 23.0 Hz), 115.04 (d, J = 22.0 Hz), 43.95; HRMS (ESI): m/z calcd for $C_{21}H_{17}O_2NaN_2F$ (M + Na)$^+$: 371.1166, found: 371.1168. |
| L-II-45<br>process ii, yield 80% | $^1$H NMR (400 MHz, CDCl$_3$) δ 9.68 (s, 1H), 8.62 (d, J = 8.6 Hz, 1H), 7.75 (s, 1H), 7.66 (dd, J = 8.7, 2.2 Hz, 1H), 7.61-7.54 (m, 3H), 7.53-7.45 (m, 1H), 7.43-7.38 (m, 2H), 7.38-7.27 (m, 4H), 4.48 (d, J = 6.2 Hz, 2H); $^{13}$C NMR (125 MHz, CDCl$_3$) δ 159.45, 157.63, 136.61, 136.58, 135.98, 135.97, 133.08, 129.71, 129.21, 129.20, 129.04, 128.17, 127.98, 127.48 (q, J =3.8 Hz), 127.08 (q, J = 32.8 Hz), 125.71 (q, J = 3.7 Hz), 124.05 (q, J = 272.6 Hz), 120.09, 44.14; HRMS (DART): m/z calcd for $C_{22}H_{18}O_2N_2F_3$ (M + H)$^+$: 399.1315, found: 399.1313. |
| L-II-46<br>process ii, yield 85% | $^1$H NMR (400 MHz, CDCl$_3$) δ 9.72 (s, 1H), 8.59-8.57 (d, J = 8.4 Hz, 1H), 8.09-8.07 (dd, J$_1$ = 1.8 Hz, J$_2$ = 8.6 Hz, 1H), 8.02-8.01 (d, J = 2 Hz, 1H), 7.78 (s, 1H), 7.58-7.54 (m, 2H), 7.50-7.46 (m, 1H), 7.43-7.41 (m, 2H), 7.36-7.27 (m, 5H), 4.49-4.48 (d, J = 6 Hz, 2H), 2.92 (s, 3H); $^{13}$C NMR (100 MHz, d6-DMSO) δ 165.56, 159.39, 157.84, 138.30, 137.89, 136.50, 133.42, 131.10, 129.44, 129.21 (2C), 128.88 (2C), 128.44, 128.29 (2C), 127.37 (2C), 126.99, 126.11, 121.22, 52.21, 42.72; HRMS-ESI: m/z calcd for $C_{23}H_{21}O_4N_2$ (M + H)$^+$: 389.1496, found: 389.1494. |
| L-II-47<br>process ii, yield 85% | $^1$H NMR (400 MHz, CDCl$_3$) δ 9.46 (s, 1H), 8.30-8.29 (d, J = 6.8 Hz, 1H), 7.81 (s, 1H), 7.53-7.50 (m, 2H), 7.45-7.42 (m, 1H), 7.40-7.38 (m, 1H), 7.35-7.32 (m, 2H), 7.30-7.28 (m, 3H), 7.22-7.20 (d, J = 6.8 Hz, 1H), 7.14 (d, J = 1.2 Hz, 1H), 4.48-4.47 (d, J = 4.8 Hz, 2H), 2.38 (s, 3H); $^{13}$C NMR (100 MHz, d6-DMSO) δ 159.83, 157.88, 138.48, 137.94, 135.09, 134.51, 131.10, 130.81, 128.80 (2C), 128.79 (2C), 128.64, 128.29 (2C), 127.70, 127.36 (2C), 126.96, 122.73,42.63, 20.52; HRMS-ESI: m/z calcd for $C_{22}H_{21}O_2N_2$ (M + H)$^+$: 345.1598, found: 345.1596. |

| ligand (new compound) | Characterization Data |
| --- | --- |
| L-II-48<br>process ii, yield 75% | $^1$H NMR (400 MHz, CDCl$_3$) δ 9.59 (s, 1H), 8.52 (d, J = 8.5 Hz, 1H), 7.81 (t, J = 6.2 Hz, 1H), 7.69-7.59 (m, 3H), 7.58-7.52 (m, 3H), 7.50-7.41 (m, 5H), 7.39-7.26 (m, 6H), 4.49 (d, J = 6.1 Hz, 2H); $^{13}$C NMR (125 MHz, CDCl$_3$) δ 159.72, 157.16, 140.09, 138.00, 137.21, 136.61, 133.25, 133.25, 132.68, 129.31, 129.17, 128.97, 128.83, 128.47, 127.91, 127.81, 127.41, 126.97, 126.92, 120.53, 43.91; HRMS (DART): m/z calcd for C$_{27}$H$_{23}$O$_2$N$_2$ (M + H)$^+$: 407.1754, found: 407.1750. |
| L-II-49<br>process ii, yield 88% | $^1$H NMR (400 MHz, CDCl$_3$) δ 9.35 (s, 1H), 8.31-8.29 (d, J = 7.6 Hz, 1H), 7.79 (s, 1H), 7.53-7.50 (m, 2H), 7.46-7.43 (m, 1H), 7.41-7.39 (m, 2H), 7.35-7.32 (m, 2H), 7.31-7.26 (m, 3H), 6.96-6.93 (dd, J$_1$ = 2.4 Hz, J$_2$ = 7.2 Hz, 1H), 6.87-6.86 (d, J = 2.4 Hz, 1H), 4.48-4.47 (d, J = 4.8 Hz, 2H), 3.83 (s, 3H); $^{13}$C NMR (100 MHz, d6-DMSO) δ 159.88, 158.12, 157.09, 138.51, 138.01, 136.78, 128.73 (2C), 128.65 (2C), 128.27 (2C), 127.74, 127.32 (2C), 126.93, 126.60, 125.27, 115.24, 113.53, 55.37. 42.54; HRMS-ESI: m/z calcd for C$_{22}$H$_{21}$O$_3$N$_2$ (M + H)$^+$: 361.1547. found: 361.1545. |
| L-II-50<br>process ii, yield 52% | $^1$H NMR (500 MHz, CDCl$_3$) δ 9.24 (s, 1H), 8.16 (d, J = 9.1 Hz, 1H), 7.83 (s, 1H), 7.54-7.46 (m, 2H), 7.46-7.37 (m, 3H), 7.36-7.31 (m, 2H), 7.31-7.26 (m, 3H), 6.70 (d, J = 9.2 Hz, 1H), 6.59 (d, J = 3.0 Hz, 1H), 4.47 (d, J = 6.2 Hz, 2H), 3.37 (q, J = 7.1 Hz, 4H), 1.17 (t, J = 7.1 Hz, 6H); $^{13}$C NMR (125 MHz, CDCl$_3$) δ 160.34, 156.65, 145.56, 138.58, 136.95, 134.89, 129.25, 129.17, 128.92, 128.19, 127.96, 122.46, 122.28, 113.35, 111.43, 44.60, 43.97, 12.74; LC-MS (ESI, m/z): 402.5 (M + H)$^+$. |
| L-II-51<br>process ii, yield 87% | $^1$H NMR (400 MHz, CDCl$_3$) δ 8.78 (s, 1H), 7.86 (s, 1H), 7.39-7.32 (m, 5H), 7.82-7.80 (d, J = 8.8 Hz, 2H), 4.55-4.54 (d, J = 6 Hz, 2H), 2.22 (s, 6H); $^{13}$C NMR (100 MHz, d6-DMSO) δ 160.40 (J = 241 Hz, 1C), 159.90, 159.04, 138.70, 137.74 (J = 9 Hz, 2C), 130.46 (J = 2 Hz, 1C), 128.34 (2C), 127.49 (2C), 126.98, 114.02 (J = 22 Hz, 2C), 42.54, 18.05 (2C); HRMS-ESI: m/z calcd for C$_{17}$H$_{18}$O$_2$N$_2$F (M + H)$^+$: 301.1347, found: 301.1347. |
| L-II-52<br>process ii, yield 93% | $^1$H NMR (400 MHz, CDCl$_3$) δ 9.02 (s, 1H), 7.98 (s, 2H), 7.81 (s, 1H), 7.40-7.25 (m, 5H), 4.55 (d, J = 6.1 Hz, 2H), 2.33 (s, 6H); $^{13}$C NMR (100 MHz, CDCl$_3$) δ 159.03, 157.68, 146.53, 138.34, 136.68, 136.29, 128.93, 128.10, 127.97, 123.28, 44.11, 18.86: LC-MS (ESI, m/z): 328.0 (M + H)$^+$. |
| L-II-53<br>process ii, yield 71% | $^1$H NMR (500 MHz, CDCl$_3$) δ 8.68 (s, 1H), 7.89 (s, 1H), 7.42-7.29 (m, 5H), 6.46 (s, 2H), 4.55 (d, J = 6.1 Hz, 2H), 2.93 (s, 6H), 2.20 (s, 6H); $^{13}$C NMR (125 MHz, CDCl$_3$) δ 160.00, 158.41, 149.99, 136.72, 135.57, 128.83, 128.01, 127.89, 121.59, 112.12, 43.93, 40.60, 18.91; LC-MS (ESI, m/z): 326.0 (M + H)$^+$. |

| ligand (new compound) | Characterization Data |
|---|---|
| 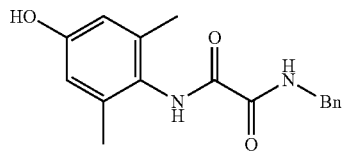 [SMILES: Cc1cc(O)cc(C)c1NC(=O)C(=O)NCc1ccccc1]<br>L-II-54<br>process ii, yield 80% | $^1$H NMR (400 MHz, CDCl$_3$) δ 8.70 (s, 1H), 7.83 (s, 1H), 7.41-7.27 (m, 6H), 6.49 (s, 2H), 4.55 (d, J = 6.1 Hz, 2H), 2.15 (s, 6H); $^{13}$C NMR (125 MHz, CDCl$_3$) δ 159.81, 158.66, 155.17, 136.79, 136.72, 129.05, 128.16, 128.15, 125.02, 115.21, 44.16, 18.63; LC-MS (ESI, m/z): 299.4 (M + H)$^+$. |
| 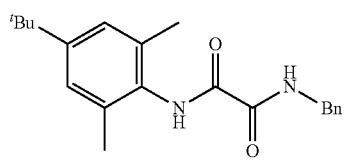 [SMILES: Cc1cc(C(C)(C)C)cc(C)c1NC(=O)C(=O)NCc1ccccc1]<br>L-II-56<br>process ii, yield 83% | $^1$H NMR (400 MHz, CDCl$_3$) δ 8.78 (s, 1H), 7.89 (s, 1H), 7.39-7.32 (m, 5H), 7.11 (s, 2H), 4.56-4.54 (d, J = 6 Hz, 2H), 2.23 (s, 6H), 1.30 (s, 9H); $^{13}$C NMR (100 MHz, d6-DMSO) δ 160.09, 158.88, 149.14, 138.76, 134.35 (2C), 131.60, 128.34 (2C), 127.53 (2C), 126.98, 124.63 (2C), 42.56, 34.01, 31.16 (3C), 18.32 (2C); HRMS-ESI: m/z calcd for C$_{21}$H$_{27}$O$_2$N$_2$ (M + H)$^+$: 339.2067, found: 339.2065. |
| 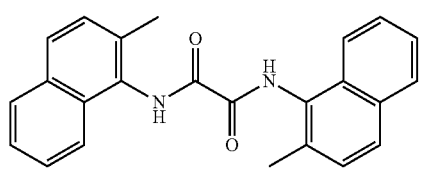 [SMILES: Cc1ccc2ccccc2c1NC(=O)C(=O)Nc1c(C)ccc2ccccc12]<br>L-II-57<br>process II, yield 75% | $^1$H NMR (400 MHz, CDCl$_3$) δ 9.32 (s, 2H), 7.94-7.92 (d, J = 8.4 Hz, 2H), 7.89-7.87 (d, J = 8.0 Hz, 2H), 7.83-7.81 (d, J = 8.4 Hz, 2H), 7.60-7.56 (m, 2H), 7.52-7.48 (m, 2H), 7.46-7.44 (d, J = 8.4 Hz, 2H), 2.53 (s, 6H); $^{13}$C NMR (100 MHz, CDCl$_3$) δ 158.79 (2C), 133.16 (2C), 132.94 (2C), 130.02 (2C), 128.96 (2C), 128.47 (2C), 128.45 (2C), 128.34 (2C), 127.20 (2C), 125.81 (2C), 122.12 (2C), 19.04 (20: HRMS-ESI: m/z calcd for C$_{24}$H$_{21}$O$_2$N$_2$ (M + H)$^+$: 369.1598, found: 369.1597. |
| 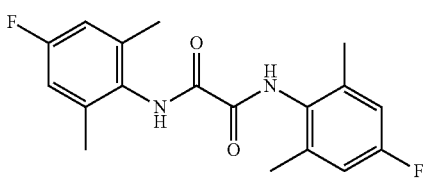 [SMILES: Cc1cc(F)cc(C)c1NC(=O)C(=O)Nc1c(C)cc(F)cc1C]<br>L-II-58<br>process II, yield 79% | $^1$H NMR (400 MHz, CDCl$_3$) δ 2.27 (s, 12H), 6.84 (d, J = 8.8 Hz, 4H), 8.77 (s, 2H); $^{13}$C NMR (125 MHz, CDCl$_3$) δ 161.62 (d, J = 246.8 Hz), 158.17, 137.42 (d, J = 8.8 Hz), 128.06 (d, J = 3.2 Hz), 114.98 (d, J = 22.1 Hz), 18.60 (d, J = 1.5 Hz); HRMS (DART) calcd. for C$_{18}$H$_{19}$O$_2$N$_2$F$_2$ (M + H)$^+$: 333.1409, Found: 333.1410. |
| 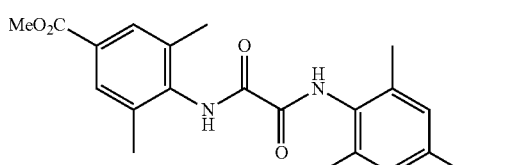<br>L-II-59<br>process II, yield 82% | $^1$H NMR (400 MHz, CDCl$_3$) δ 2.34 (s, 12H), 3.92 (s, 6H), 7.82 (s, 4H), 8.92 (s, 2H); $^{13}$C NMR (125 MHz, CDCl$_3$) δ 166.63, 157.56, 136.42, 135.10, 129.66, 129.36, 52.21, 18.57: HRMS (DART) calcd. for C$_{22}$H$_{25}$N$_2$O$_6$ (M + H)$^+$: 413.1707, Found: 413.1704. |
| 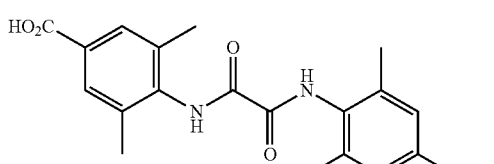<br>L-II-60<br>process ii, yield 82% | $^1$H NMR (400 MHz, d6-DMSO) δ 2.24 (s, 12H), 7.71 (s, 4H), 10.54 (s, 2H), 12.87 (br s, 2H); $^{13}$C NMR (100 MHz, d6-DMSO) δ 167.0, 158.52, 138.44, 135.56, 129.22, 128.74, 18.00; HRMS (DART) calcd. for C$_{20}$H$_{21}$N$_2$O$_6$ (M + H)$^+$: 385.1394, Found: 385.1393. |

| ligand (new compound) | Characterization Data |
|---|---|
| 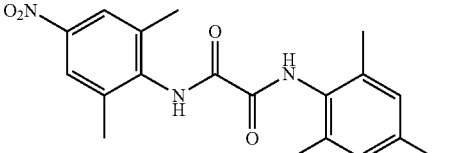<br>L-II-61<br>process II, yield 89% | $^1$H NMR (400 MHz, CDCl$_3$) δ 8.94 (s, 2H), 8.03 (s, 4H), 1.59 (s, 12H): LC-MS (ESI, m/z): 387.0 (M + H)$^+$. |
| 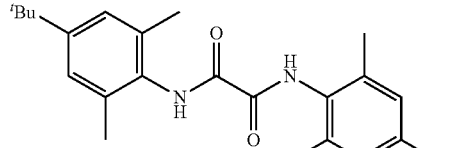<br>L-II-63<br>process II, yield 95% | $^1$H NMR (400 MHz, CDCl$_3$) δ 1.31 (s, 18H), 2.28 (s, 12H), 7.13 (s, 4H), 8.81 (s, 2H); $^{13}$C NMR (100 MHz, CDCl$_3$) δ 158.27, 150.72, 134.25, 129.72, 125.50, 34.42, 31.36, 18.74; HRMS (DART) calcd. for C$_{26}$H$_{37}$O$_2$N$_2$ (M + H)$^+$: 409.2850, Found: 409.2847. |
| 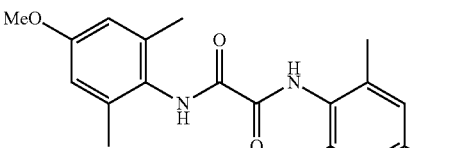<br>L-II-64<br>process II, yield 86% | $^1$H NMR (400 MHz, d6-DMSO) δ 2.13 (s, 12H), 3.74 (s, 6H), 6.69 (s, 4H), 10.09 (s, 2H); $^{13}$C NMR (100 MHz, d6-DMSO) δ 159.17, 157.68, 136.26, 127.03, 112.87, 55.05, 18.20: HRMS (DART) calcd. for C$_{20}$H$_{25}$N$_2$O$_4$ (M + H)$^+$: 357.1809, Found: 357.1807. |
| 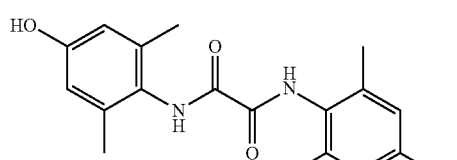<br>L-II-65<br>process II, yield 90% | $^1$H NMR (400 MHz, d6-DMSO) δ 2.06 (s, 12H), 6.50 (s, 4H), 9.25 (s, 2H), 9.96 (s, 2H); $^{13}$C NMR (100 MHz, d6-DMSO) δ 159.25, 155.83, 136.04, 125.49, 114.24, 18.09: HRMS (DART) calcd. for C$_{18}$H$_{21}$N$_2$O$_4$ (M + H)$^+$: 329.1496, Found: 329.1496. |
| 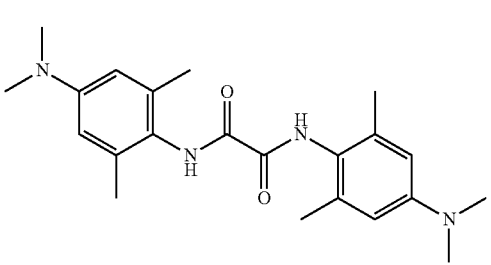<br>L-II-66<br>process II, yield 69% | $^1$H NMR (400 MHz, CDCl$_3$) δ 8.72 (s, 2H), 6.49 (s, 4H), 2.93 (s, 12H), 2.23 (s, 12H); $^{13}$C NMR (100 MHz, CDCl$_3$) δ 158.80, 149.77, 135.62, 121.99. 112.33, 40.74, 18.89; LC-MS (ESI, m/z): 383.0 (M + H)$^+$. |
| 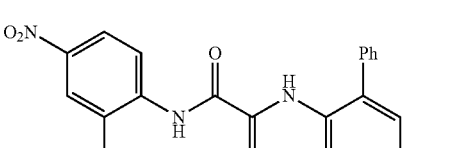<br>L-II-67<br>process II, yield 94% | $^1$H NMR (500 MHz, CDCl$_3$) δ 9.73 (s, 2H), 8.63 (d, J = 10 Hz, 2H), 8.30-8.20 (m, 4H), 7.65-7.35 (m, 10H); HRMS (DART) calcd. for C$_{26}$H$_{19}$N$_4$O$_6$ (M + H)$^+$: 483.1299, Found: 483.1295. |

| ligand (new compound) | Characterization Data |
|---|---|
| 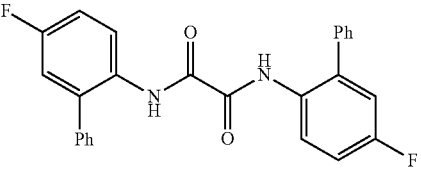 [SMILES: O=C(Nc1ccc(F)cc1-c1ccccc1)C(=O)Nc1ccc(F)cc1-c1ccccc1]<br>L-II-68<br>process II, yield 87% | $^1$H NMR (400 MHz, CDCl$_3$) δ 7.02-7.10 (m, 4H), 7.37-7.40 (m, 4H), 7.46-7.57 (m, 6H), 8.32-8.36 (m, 2H), 9.44 (s, 2H); $^{13}$C NMR (100 MHz, CDCl$_3$) δ 159.76 (d, J =246.3 Hz), 157.26, 136.29 (d, J = 1.5 Hz), 135.10 (d, J = 7.8 Hz), 129.55, 129.50 (d, J = 2.9 Hz), 129.08, 129.00, 122.27 (d, J = 8.3 Hz), 117.24 (d, J = 23.1 Hz), 115.11 (d, J = 22.0 Hz); LC-MS (ESI, m/z): 429.3 (M + H)$^+$. |
| 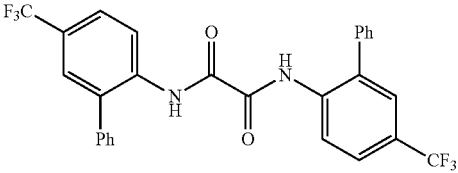 [SMILES: O=C(Nc1ccc(C(F)(F)F)cc1-c1ccccc1)C(=O)Nc1ccc(C(F)(F)F)cc1-c1ccccc1]<br>L-II-69<br>process II, yield 81% | $^1$H NMR (400 MHz, CDCl$_3$) δ 9.63 (s, 2H), 8.55 (d, J = 8.6 Hz, 2H), 7.66-7.50 (m, 10H), 7.44-7.37 (m, 4H); $^{13}$C NMR (125 MHz, CDCl$_3$) δ 157.32, 136.25, 135.82, 133.16, 129.77, 129.32, 129.19, 127.51, 126.98 (q, J = 32.6 Hz), 125.69, 123.97 (d, J = 271.4 Hz), 120.19; LC-MS (ESI, m/z): 529.4 (M + H)$^+$. |
| 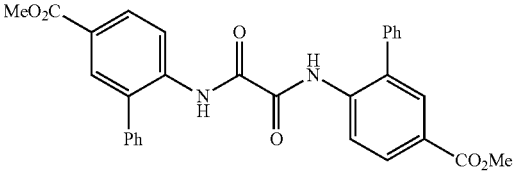 [SMILES: COC(=O)c1ccc(NC(=O)C(=O)Nc2ccc(C(=O)OC)cc2-c2ccccc2)c(-c2ccccc2)c1]<br>L-II-70<br>process II, yield 90% | $^1$H NMR (400 MHz, CDCl$_3$) δ 9.67 (s, 2H), 8.52-8.50 (d, J = 8.4 Hz, 2H), 8.06-8.03 (dd, J$_1$ = 2.0 Hz, J$_2$= 8.4 Hz, 2H), 8.01-8.00 (d, J = 2 Hz, 2H), 7.59-7.54 (m, 4H), 7.53-7.49 (m, 2H), 7.42-7.39 (m, 4H), 3.91 (s, 6H); $^{13}$C NMR (100 MHz, d6-DMSO) δ 166.48 (2C), 157.30 (2C), 137.21 (2C), 136.21 (2C), 132.66 (2C), 131.91 (2C), 130.17 (2C), 129.67 (4C), 129.27 (4C), 129.08 (2C), 126.84 (2C), 119.61 (2C), 52.37 (2C); HRMS-ESI: m/z calcd for C$_{30}$H$_{25}$O$_6$N$_2$ (M + H)$^+$: 509.1707, found: 509.1704. |
| 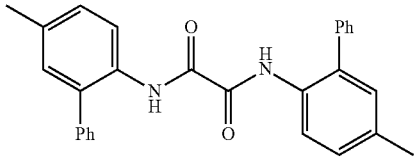<br>L-II-71<br>process II, yield 91% | $^1$H NMR (400 MHz, CDCl$_3$) δ 9.47 (s, 2H), 8.25-8.23 (d, J = 8.0 Hz, 2H), 7.53-7.50 (m, 4H), 7.46-7.42 (m, 2H), 7.39-7.37 (d, J = 7.6 Hz, 4H), 7.18-7.16 (d, J = 8.4 Hz, 2H), 7.12 (s, 2H), 2.36 (s, 6H); $^{13}$C NMR (100 MHz, d6-DMSO) δ 157.40 (2C), 137.51 (2C), 135.13 (2C), 132.93 (2C), 131.10 (2C), 130.91 (2C), 129.34 (4C), 129.26 (4C), 129.05 (2C), 128.40 (2C), 120.40 (2C), 21.10 (2C); HRMS-ESI: m/z calcd for C$_{28}$H$_{25}$O$_2$N$_2$ (M + H)$^+$: 421.1911, found: 421.1906. |
| 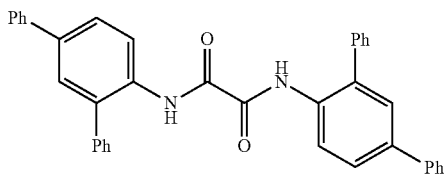 [SMILES: O=C(Nc1ccc(-c2ccccc2)cc1-c1ccccc1)C(=O)Nc1ccc(-c2ccccc2)cc1-c1ccccc1]<br>L-II-72<br>process II, yield 92% | $^1$H NMR (500 MHz, CDCl$_3$) δ 9.60 (s, 2H), 8.48 (d, J = 8.5 Hz, 2H), 7.65-7.53 (m, 12H), 7.52-7.40 (m, 10H), 7.38-7.32 (m, 2H); $^{13}$C NMR (125 MHz, CDCl$_3$) δ 157.30, 140.07, 138.13, 137.17, 133.25, 132.53, 129.36, 129.20, 128.99, 128.84, 128.53, 127.45, 126.96, 126.94, 120.60; LC-MS (ESI, m/z): 545.3 (M + H)$^+$. |
| 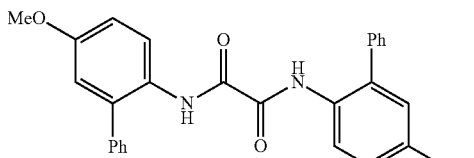<br>L-II-73<br>process II, yield 87% | $^1$H NMR (400 MHz, CDCl$_3$) δ 9.37 (s, 2H), 8.26-8.24 (d, J = 8.8 Hz, 2H), 7.56-7.50 (m, 4H), 7.46-7.43 (m, 2H), 7.40-7.38 (m, 4H), 6.92-6.89 (dd, J$_1$ = 2.8 Hz, J$_2$ = 8.8 Hz, 2H), 6.85 (d, J = 3.2 Hz, 2H), 3.82 (s, 6H); $^{13}$C NMR (100 MHz, d6-DMSO) δ 157.31 (2C), 156.90 (2C), 137.38 (2C), 134.69 (2C), 129.37 (4C), 129.18 (4C), 128.58 (2C), 126.73 (2C), 122.14 (2C), 115.82 (2C), 113.57 (2C), 55.68 (2C); HRMS-ESI: m/z calcd for C$_{28}$H$_{25}$O$_4$N$_2$ (M + H)$^+$: 453.1809, found: 453.1805. |

-continued

| ligand (new compound) | Characterization Data |
|---|---|
| 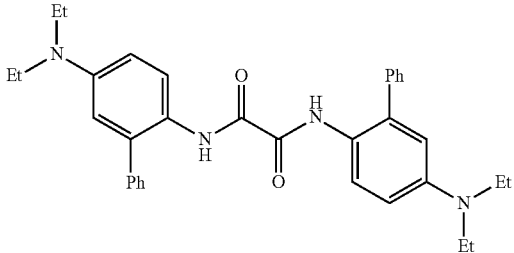 [SMILES: CCN(CC)c1ccc(NC(=O)C(=O)Nc2ccc(N(CC)CC)cc2-c2ccccc2)c(-c2ccccc2)c1]<br>L-II-74<br>process II, yield 69% | $^1$H NMR (500 MHz, CDCl$_3$) δ 9.27 (s, 2H), 8.11 (d, J = 9.0 Hz, 2H), 7.64-7.35 (m, 10H), 6.66 (dd, J = 9.0, 3.0 Hz, 2H), 6.57 (d, J = 3.0 Hz, 2H), 3.35 (q, J = 7.0 Hz, 8H), 1.16 (t, J = 7.0 Hz, 12H), $^{13}$C NMR (125 MHz, CDCl$_3$) δ 157.29, 145.49, 138.63, 134.75, 129.27, 129.16, 128.13, 122.49, 122.40, 113.44, 111.47, 44.59, 12.73. LC-MS (ESI, m/z): 535.3 (M + H)$^+$. |
| 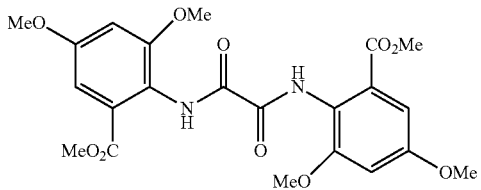 [SMILES: COC(=O)c1cc(OC)cc(OC)c1NC(=O)C(=O)Nc1c(OC)cc(OC)cc1C(=O)OC]<br>L-II-78<br>process II, yield 86% | $^1$H NMR (400 MHz, CDCl$_3$) δ 9.53 (s, 2H), 6.97 (d, J = 2.8 Hz, 2H), 6.67 (d, J = 2.4 Hz, 2H), 3.88 (s, 6H), 3.86 (s, 6H), 3.84 (s, 6H); $^{13}$C NMR (100 MHz, CDCl$_3$) δ 167.14 (2C), 158.44 (2C), 157.80 (2C), 154.22 (2C), 127.63 (2C), 117.61 (2C), 105.23 (2C), 103.06 (2C), 56.32 (2C), 55.87 (2C), 52.57 (2C); LC-MS (ESI, m/z): 477.5 (M + H)$^+$. |
| 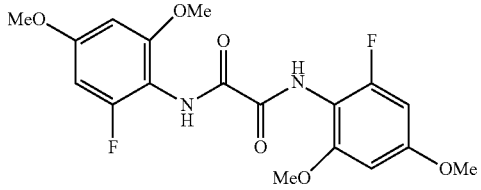 [SMILES: COc1cc(F)c(NC(=O)C(=O)Nc2c(F)cc(OC)cc2OC)c(OC)c1]<br>L-II-79<br>process II, yield 81% | $^1$H NMR (400 MHz, CDCl$_3$) δ 8.63 (s, 2H), 6.39-6.25 (m, 4H), 3.83 (s, 6H), 3.80 (s, 6H); $^{13}$C NMR (100 MHz, CDCl$_3$) δ 160.12 (J = 12.9 Hz, 2C), 158.48 (J = 247.4 Hz, 2C), 158.05 (2C), 155.71 (J = 7.6 Hz, 2C), 105.46 (J = 15.8 Hz, 2C), 94.97 (J = 2.6 Hz, 2C), 93.73 (J = 24.5 Hz, 2C), 56.21 (2C), 55.87 (2C); LC-MS (ESI, m/z): 397.4 (M + H)$^+$. |

The following ligands were prepared according to process II:

| Ligang Structure | Characterization Data of Structure |
|---|---|
| 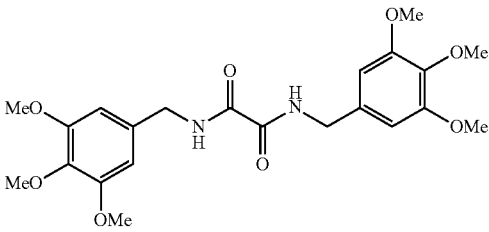<br>L-II-21,<br>yield 81% | $^1$H NMR (400 MHz, DMSO-d6) δ 9.27 (t, J = 6.4 Hz, 1H), 6.61 (s, 2H), 4.26 (d, J = 6.4 Hz, 2H), 3.73 (s, 6H), 3.62 (s, 3H),; $^{13}$C NMR (101 MHz, DMSO-d6) δ 160.07, 152.74, 136.48, 134.34, 104.93, 59.98, 55.78, 42.67. ESI-MS m/z 471.3 (M + Na)$^+$; HRMS Calcd. For C$_{22}$H$_{28}$N$_2$O$_8$ (M + Na)$^+$ requires 471.1738; found: 471.1745. |
| 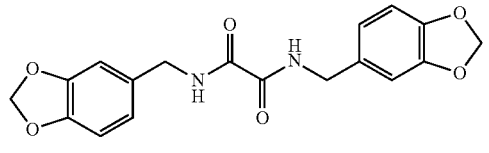 [SMILES: O=C(NCc1ccc2c(c1)OCO2)C(=O)NCc1ccc2c(c1)OCO2]<br>L-II-79,<br>yield 85% | $^1$H NMR (400 MHz, DMSO-d6) δ 9.25 (t, J = 6.4 Hz, 1H), 6.87-6.80 (m, 2H), 6.74 (dd, J = 8.0, 1.3 Hz, 1H), 5.97 (s, 2H), 4.22 (d, J = 6.5 Hz, 2H),; $^{13}$C NMR (101 MHz, DMSO-d6) δ 160.01, 147.18, 146.18, 132.60, 120.77, 108.16, 108.00, 100.84, 42.19. ESI-MS m/z 379.2 (M + Na)$^+$; HRMS Calcd. For C$_{18}$H$_{16}$N$_2$NaO$_6$ (M + Na)$^+$ requires 379.0906; found: 379.0901. |

| Ligang Structure | Characterization Data of Structure |
|---|---|
| 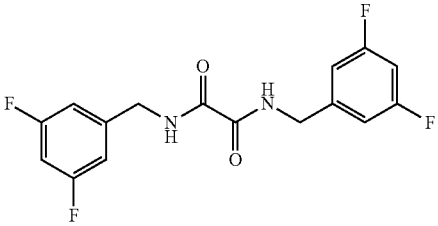 [SMILES: O=C(NCc1cc(F)cc(F)c1)C(=O)NCc1cc(F)cc(F)c1]<br>L-II-80,<br>yield 80% | $^1$H NMR (400 MHz, DMSO-d6) δ 9.43 (t, J = 6.4 Hz, 1H), 7.11 (tt, J = 9.4, 2.3 Hz, 1H), 7.05-6.94 (m, 2H), 4.35 (d, J = 6.4 Hz, 2H),; $^{13}$C NMR (101 MHz, DMSO-d6) δ (163.60, 163.47, 161.16, 161.02), 160.20, (143.49, 143.40, 143.31), (110.49, 110.43, 110.31, 110.24), (102.64, 102.38, 102.13), 41.78. ESI-MS m/z 339.2 (M − H)$^-$; HRMS Calcd. For $C_{16}H_{11}F_4N_2O_2$ (M−H)$^-$ requires 339.0762.; found: 339.0767. |
| 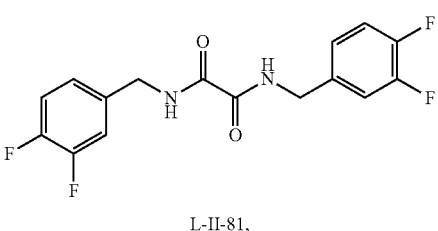<br>L-II-81,<br>yield 78% | $^1$H NMR (400 MHz, DMSO-d6) δ 9.40 (t, J = 6.1 Hz, 1H), 7.35 (dt, J = 20.3, 10.2 Hz, 2H), 7.12 (s, 1H), 4.31 (d, J = 6.3 Hz, 2H),; $^{13}$C NMR (101 MHz, DMSO-d6) δ 160.12, (150.47, 150.34, 149.64), (148.03, 147.90, 147.33, 147.21), (136.54, 136.48, 136.45), (124.21, 124.18, 124.15, 124.12), (117.38, 117.21), (116.57, 116.40), 41.52.; ESI-MS m/z 339.1 (M − H)$^-$; HRMS Calcd. For $C_{16}H_{11}F_4N_2O_2$ (M − H)$^-$ requires 339.0762.; found: 339.0752. |
| 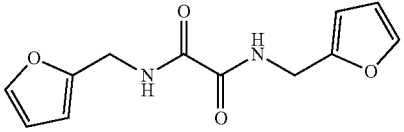 [SMILES: O=C(NCc1ccco1)C(=O)NCc1ccco1]<br>L-II-82<br>(yield 85%) | $^1$H NMR (400 MHz, DMSO-d6) δ 9.22 (t, J = 6.1 Hz, 1H), 7.58-7.53 (m, 1H), 6.38 (dd, J = 3.1, 1.9 Hz, 1H), 6.22 (d, J = 3.2 Hz, 1H), 4.31 (d, J = 6.2 Hz, 2H),; $^{13}$C NMR (101 MHz, DMSO-d6) δ 159.86, 151.48, 142.13, 110.50, 107.14, 35.76. ESI-MS m/z 271.1 (M + Na)$^+$; HRMS Calcd. For $C_{12}H_{12}N_2NaO_4$ (M + Na)$^+$ requires 271.0689.; found: 271.0693. |
| 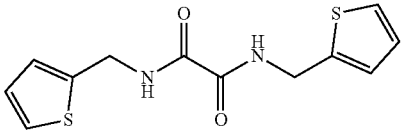 [SMILES: O=C(NCc1cccs1)C(=O)NCc1cccs1]<br>L-II-83,<br>yield 75% | $^1$H NMR (400 MHz, DMSO-d6) δ 9.42 (t, J = 6.3 Hz, 1H), 7.38 (dd, J = 5.0. 1.3 Hz, 1H), 6.95 (dt, J = 4.9, 2.8 Hz, 2H), 4.47 (d, J = 6.4 Hz, 2H),; $^{13}$C NMR (101 MHz, DMSO-d6) δ 159.75, 141.23, 126.66, 125.93, 125.21, 37.37. ESI-MS m/z 302.9 (M + Na)$^+$; HRMS Calcd. For $C_{12}H_{12}N_2NaO_2S_2$ (M + Na)$^+$ requires 303.0232.; found: 303.0233. |
| 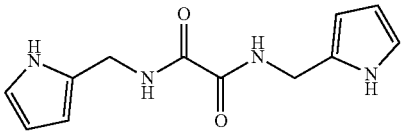 [SMILES: O=C(NCc1ccc[nH]1)C(=O)NCc1ccc[nH]1]<br>L-II-84,<br>yield 78% | $^1$H NMR (400 MHz, DMSO-d6) δ 10.54 (s, 1H), 8.91 (t, J = 6.1 Hz, 1H), 6.63 (dd, J = 4.2, 2.5 Hz, 1H), 5.89 (dd, J = 5.5, 2.7 Hz, 1H), 5.88-5.84 (m, 1H), 4.27 (d, J = 6.2 Hz, 2H),; $^{13}$C NMR (101 MHz, DMSO-d6) δ 159.59, 125.66, 117.23, 107.13, 105.93, 35.72. ESI-MS m/z 269.1 (M + Na)$^+$; HRMS Calcd. For $C_{12}H_{14}N_4NaO_2$ (M + Na)$^+$ requires 269.1009.; found: 269.1002. |
| 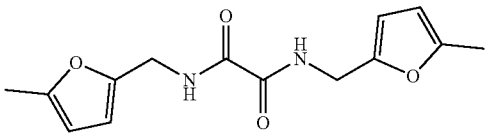<br>L-II-85,<br>yield 81% | $^1$H NMR (400 MHz, DMSO-d6) δ 9.12 (t, J = 6.1 Hz, 1H), 6.08 (d, J = 2.9 Hz, 1H), 5.96 (d, J = 2.6 Hz, 1H), 4.25 (d, J = 6.2 Hz, 2H), 2.21 (s, 3H),; $^{13}$C NMR (101 MHz, DMSO-d6) δ 159.78, 150.70, 149.64, 108.00, 106.38, 35.77, 13.25. ESI-MS m/z 299.1 (M + Na)$^+$; HRMS Calcd. For $C_{14}H_{15}N_2O_4$ (M + Na)$^+$ requires 275.1037.; found: 275.1032. |
| 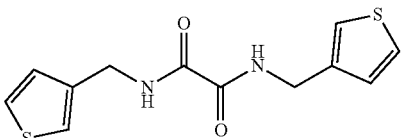<br>L-II-86,<br>yield 78% | $^1$H NMR (400 MHz, DMSO-d6) δ 9.26 (t, J = 6.3 Hz, 1H), 7.46 (dd, J = 4.9, 3.0 Hz, 1H), 7.28 (d, J = 1.8 Hz, 1H), 7.04 (dd, J = 4.9, 1.0 Hz, 1H), 4.31 (d, J = 6.4 Hz, 2H),; $^{13}$C NMR (101 MHz, DMSO-d6) δ 159.95, 139.41, 127.56, 126.28, 122.07, 37.90. ESI-MS m/z 302.9 (M − H)$^-$; HRMS Calcd. For $C_{12}H_{11}N_2O_2S_2$ (M − H)$^-$ requires 279.0267.; found: 279.0257. |

| Ligang Structure | Characterization Data of Structure |
|---|---|
| 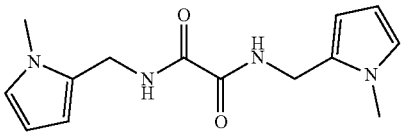 [SMILES: Cn1cccc1CNC(=O)C(=O)NCc1cccn1C]<br>L-II-87,<br>yield 72% | ¹H NMR (400 MHz, DMSO-d6) δ 9.00 (t, J = 5.8 Hz, 1H), 6.62 (s, 1H), 5.90 (s, 1H), 5.88-5.84 (m, 1H), 4.27 (d, J = 6.1 Hz, 1H), 3.55 (s, 1H), ESI-MS m/z [M + 1]⁺ 275.26 |
| 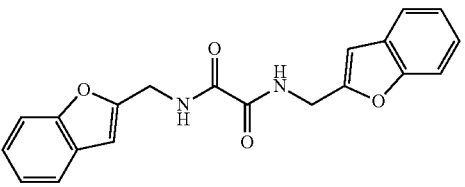 [SMILES: O=C(NCc1cc2ccccc2o1)C(=O)NCc1cc2ccccc2o1]<br>L-II-88,<br>yield 90% | ¹H NMR (400 MHz, DMSO-d6) δ 9.44 (t, J = 6.0 Hz, 1H), 7.58 (d, J = 7.3 Hz, 1H), 7.53 (d, J = 8.0 Hz, 1H), 7.30-7.18 (m, 2H), 6.72 (s, 1H), 4.52 (d, J = 6.0 Hz, 2H), ESI-MS m/z 371.1 (M + Na)⁺; HRMS Calcd. For $C_{20}H_{15}N_2O_4$ (M + Na)⁺ requires 347.1037.; found: 347.1041. |
| 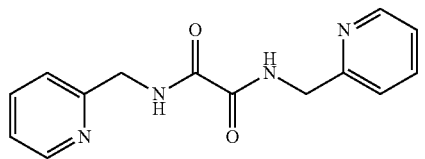 [SMILES: O=C(NCc1ccccn1)C(=O)NCc1ccccn1]<br>L-II-89,<br>yield 81% | ¹H NMR (400 MHz, DMSO-d6) δ 9.33 (t, J = 6.1 Hz, 1H), 8.54-8.48 (m, 1H), 7.77 (td, J = 7.7, 1.8 Hz, 1H), 7.28 (dd, J = 10.1, 4.9 Hz, 2H), 4.47 (d, J = 6.2 Hz, 2H),; ¹³C NMR (101 MHz, DMSO-d6) δ 160.14, 157.37, 148.87, 136.78, 122.26, 121.03, 44.22. ESI-MS m/z 293.1 (M + Na)⁺; HRMS Calcd. For $C_{14}H_{14}N_4NaO_2$ (M + Na)⁺ requires 293.1009.; found: 293.1012. |
| 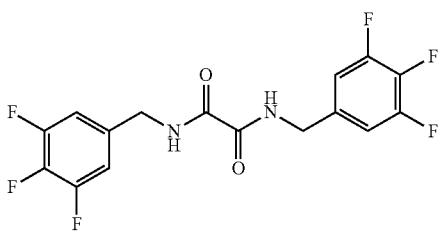 [SMILES: O=C(NCc1cc(F)c(F)c(F)c1)C(=O)NCc1cc(F)c(F)c(F)c1]<br>L-II-90,<br>yield 84% | ¹H NMR (400 MHz, DMSO-d6) δ 9.42 (s, 2H), 6.86-6.68 (m, 4H); ESI-MS m/z 377.2 (M + H)⁺. |
| 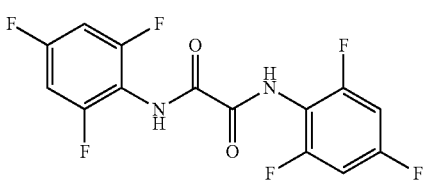 [SMILES: O=C(Nc1c(F)cc(F)cc1F)C(=O)Nc1c(F)cc(F)cc1F]<br>L-II-91 | ¹H NMR (400 MHz, DMSO-d6) δ 10.78 (s, 2H), 7.43-7.31 (m, 4H); ¹³C NMR (100 MHz, DMSO-d6) δ 161.15 (dt, J = 246, 15.3 Hz, 2C), 158.95 (2C), 158.49 (ddd, J = 249, 15.9, 7.3 Hz, 4C), 110.78 (td, J = 17.2, 5.1 Hz, 2C), 101.65 (td, J = 27.2, 2.9 Hz, 4C); ESI-MS: 349.0 (M + H)⁺ |
| 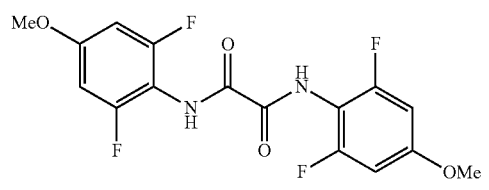 [SMILES: COc1cc(F)c(NC(=O)C(=O)Nc2c(F)cc(OC)cc2F)c(F)c1]<br>L-II-92,<br>yield 81% | ¹H NMR (400 MHz, DMSO-d6) δ 10.52 (s, 2H), 6.88 (d, J = 9.6 Hz, 4H), 3.81 (s, 6H); ¹³C NMR (100 MHz, DMSO-d6) δ 159.93 (t, J = 13.6 Hz, 2C), 159.30 (2C), 158.89 (dd, J = 246, 8.1 Hz, 4C), 106.33 (t, J = 17.8 Hz, 2C), 99.02 (d, J = 26.7 Hz, 4C), 56.73 (2C); ESI-MS: 395.2 (M + Na)⁺ |

| Ligang Structure | Characterization Data of Structure |
|---|---|
| 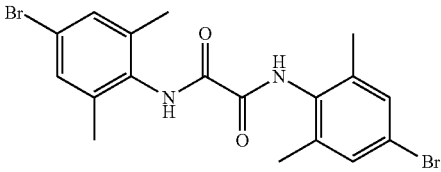 [SMILES: Cc1cc(Br)cc(C)c1NC(=O)C(=O)Nc1c(C)cc(Br)cc1C]<br>L-II-93,<br>yield 86% | $^1$H NMR (400 MHz, DMSO-d6) δ 10.36 (s, 2H), 7.36 (s, 4H), 2.16 (s, 12H); $^{13}$C NMR (100 MHz, DMSO-d6) δ 18.16, 120.14, 130.72, 134.23, 138.38, 159.15; ESI-MS: 453.0 (M + H)$^+$ |
| 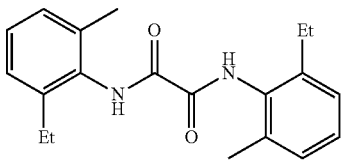 [SMILES: CCc1cccc(C)c1NC(=O)C(=O)Nc1c(C)cccc1CC]<br>L-II-94,<br>yield 83% | $^1$H NMR (400 MHz, DMSO-d6) δ 10.31 (s, 2H), 7.18 (dd, J = 8.1, 6.6 Hz, 2H), 7.12 (d, J = 7.4 Hz, 4H), 2.54 (q, J = 7.6 Hz, 4H), 2.17 (s, 6H), 1.11 (t, J = 7.6 Hz, 6H); $^{13}$C NMR (100 MHz, DMSO-d6) δ 14.84, 18.42, 24.92, 126.65, 127.75, 128.25, 134.24, 135.88, 141.45, 159.85; ESI-MS: 325.3 (M + H)$^+$ |
| 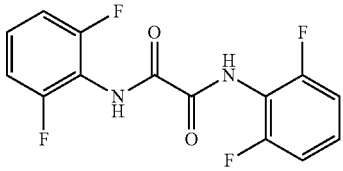 [SMILES: O=C(Nc1c(F)cccc1F)C(=O)Nc1c(F)cccc1F]<br>L-II-95,<br>yield 79% | $^1$H NMR (400 MHz, DMSO-d6) δ 10.78 (s, 2H), 7.50-7.41 (m, 2H), 7.29-7.20 (m, 4H); $^{13}$C NMR (100 MHz, DMSO-d6) δ 158.95 (2C), 158.36 (dd, J = 248, 4.8 Hz, 4C), 129.67 (t, J = 9.9 Hz, 2C), 113.81 (t, J = 16.8 Hz, 2C), 112.54 (dd, J = 18.2, 4.9 Hz, 4C); ESI-MS: 335.1 (M + Na)$^+$ |
| 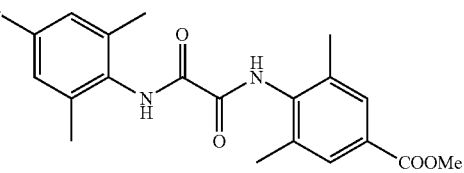<br>L-II-96,<br>yield 72% | $^1$H NMR (400 MHz, DMSO-d6) δ 10.53 (s, 1H), 10.39 (s, 1H), 7.73 (s, 2H), 7.37 (s, 2H), 3.85 (s, 3H), 2.24 (s, 6H), 2.17 (s, 6H); $^{13}$C NMR (100 MHz, DMSO-d6) δ 18.16, 18.47, 52.59, 120.16, 128.56, 129.03, 130.73, 134.21, 136.34, 138.38, 139.38, 159.05, 159.08, 166.47; ESI-MS: 433.1 (M + H)$^+$ |
| 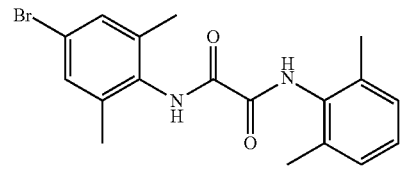 [SMILES: Cc1cccc(C)c1NC(=O)C(=O)Nc1c(C)cc(Br)cc1C]<br>L-II-97,<br>yield 82% | H NMR (400 MHz, DMSO-d6) δ 10.34 (s, 1H), 10.31 (s, 1H), 7.36 (s, 2H), 7.13-7.10 (m, 3H), 2.17 (s, 12H); $^{13}$C NMR (100 MHz, DMSO-d6) δ 18.17, 18.45, 120.10, 127.47, 128.24, 130.71, 134.32, 134.65, 135.57, 138.39, 159.10, 159.39; ESI-MS: 397.2 (M + Na)$^+$ |
| 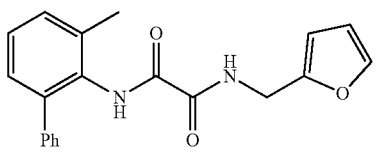<br>L-II-98,<br>yield 81% | $^1$H NMR (400 MHz, DMSO-d6) δ 10.69 (s, 1H), 9.37 (t, J = 6.1 Hz, 1H), 7.95-7.89 (m, 1H), 7.84 (d, J = 8.4 Hz, 1H), 7.74 (d, J = 8.0 Hz, 1H), 7.62 (d, J = 1.0 Hz, 1H), 7.55-7.43 (m, 3H), 6.43 (dd, J = 3.1, 1.9 Hz, 1H), 6.32 (d, J = 3.0 Hz, 1H), 4.43 (d, J = 6.2 Hz, 2H), 2.31 (s, 3H),; $^{13}$C NMR (101 MHz, DMSO-d6) δ 159.99, 159.46, 151.51, 142.21, 132.62, 132.21, 130.35, 130.07, 128.60, 127.83, 127.11, 126.37, 125.28, 122.85, 110.56, 107.34, 35.91, 18.17. |

| Ligang Structure | Characterization Data of Structure |
|---|---|
| 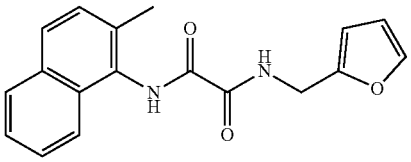 [SMILES: Cc1ccc2ccccc2c1NC(=O)C(=O)NCc1ccco1]<br>L-II-99,<br>yield 85% | $^1$H NMR (400 MHz, DMSO-d6) δ 10.69 (s, 1H), 9.37 (t, J = 6.1 Hz, 1H), 7.95-7.89 (m, 1H), 7.84 (d, J = 8.4 Hz, 1H), 7.74 (d, J = 8.0 Hz, 1H), 7.62 (d, J = 1.0 Hz, 1H), 7.55-7.43 (m, 3H), 6.43 (dd, J = 3.1, 1.9 Hz, 1H), 6.32 (d, J = 3.0 Hz, 1H), 4.43 (d, J = 6.2 Hz, 2H), 2.31 (s, 3H),; $^{13}$C NMR (101 MHz, DMSO-d6) δ 159.99. 159.46, 151.51, 142.21, 132.62, 132.21, 130.35, 130.07, 128.60, 127.83, 127.11, 126.37, 125.28, 122.85, 110.56, 107.34, 35.91, 18.17. |

Example 2 Synthesis of N-benzyl-4-methylaniline by Coupling Reaction of 1-chloro-4-methylbenzene with Benzylamine

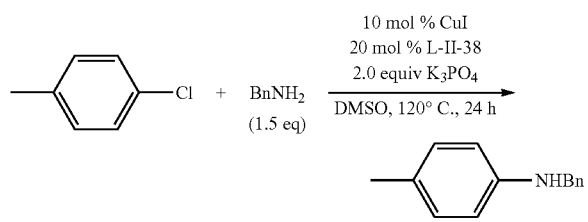

Copper (I) iodide (0.05 mmol), ligand (0.1 mmol) and potassium phosphate (1.0 mmol) were added into a 10 mL of Schlenk tube. The tube was then evacuated and backfilled with argon (this sequence was repeated three times), and then 1-chloro-4-methylbenzene (0.5 mmol), benzylamine (0.75 mmol) and 1 mL of DMSO were added. The reaction mixture was stirred well at 120° C. for 24 hours. After cooling, water and ethyl acetate were added and the mixture was separated. The aqueous phase was extracted twice with ethyl acetate. The combined organic phase was dried over anhydrous sodium sulfate. After concentration, the residue was purified by column chromatography (petroleum ether: ethyl acetate=50:1) to give the product N-benzyl-4-methyl-aniline (89 mg, yield 91%).

$^1$H NMR (400 MHz, CDCl$_3$) δ 7.34-7.21 (m, 5H), 6.96 (d, J=8.0 Hz, 2H), 6.54 (d, J=8.4 Hz, 2H), 4.28 (s, 2H), 3.88 (br s, 1H), 2.22 (s, 3H); $^{13}$C NMR (100 MHz, CDCl$_3$) δ 20.6, 48.8, 113.2, 126.9, 127.3, 127.7, 128.8, 130.0, 139.8, 146.1; HRMS (ESI) calcd. for C$_{14}$H$_{16}$N (M+H)$^+$: 198.1283, Found: 198.1287.

Example 3 Synthesis of N-benzyl-4-methylaniline by Coupling Reaction of 1-chloro-4-methylbenzene with Benzylamine The operation of this example is the same as that of Example 2 except that different oxalic amide ligands were used. The results are shown in the following table.

| Ligand | Yield/% | Ligand | Yield/% | Ligand | Yield/% |
|---|---|---|---|---|---|
| L-I-1 | 62 | L-II-9 | 75 | L-II-38 | 92 |
| L-I-2 | 64 | L-II-13 | 52 | L-II-31 | 86 |
| L-I-7 | 65 | L-II-14 | 17 | L-II-29 | 66 |
| L-I-23 | 62 | L-II-7 | 73 | L-II-27 | 45 |
| L-I-22 | 59 | L-II-15 | 56 | L-II-33 | 82 |
| L-I-24 | 44 | L-II-16 | 11 | L-II-36 | 73 |
| L-I-27 | 74 | L-II-24 | 61 | L-II-28 | 17 |
| L-I-9 | 55 | L-II-18 | 40 | L-II-34 | 57 |
| L-I-8 | 67 | L-II-1 | 56 | L-II-35 | 21 |
| L-I-25 | 75 | L-II-8 | 60 | L-II-30 | 65 |
| L-I-31 | 40 | L-II-5 | 64 | L-II-37 | 76 |
| L-I-32 | 34 | L-II-6 | 74 | L-II-4 | 81 |
| L-I-36 | 17 | L-II-41 | 62 | L-II-19 | 40 |
| L-II-20 | 70 | L-II-21 | 65 | L-II-22 | 25 |
| L-II-23 | 60 | L-I-4 | 37 | L-I-34 | 20 |
| L-I-39 | 64 | L-II-61 | <10 | L-II-59 | 46 |
| L-II-60 | 10 | L-II-58 | 81 | L-II-62 | 63 |
| L-II-63 | 76 | L-II-66 | 89 | L-II-64 | 92 |
| L-II-65 | 44 | L-II-67 | <10 | L-II-69 | 23 |
| L-II-70 | 48 | L-II-68 | 61 | L-II-72 | 77 |
| L-II-71 | 87 | L-II-73 | 88 | L-II-74 | 85 |

Example 4 Synthesis of N-benzyl-4-methylaniline by Coupling Reaction of 1-chloro-4-methylbenzene with Benzylamine

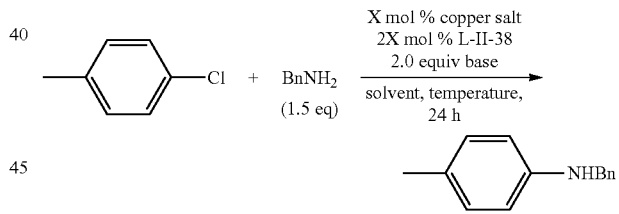

The operation of this example was the same as that of Example 2 except different copper salt as catalyst, base, solvent and temperature were used. The results are shown in the following table.

| No. | Copper salt | X | Base | Solvent | Temperature/° C. | Yield/% |
|---|---|---|---|---|---|---|
| 1 | CuI | 10 | K$_3$PO$_4$ | DMSO | 120 | 92 |
| 2 | CuBr | 10 | K$_3$PO$_4$ | DMSO | 120 | 81 |
| 3 | CuCl | 10 | K$_3$PO$_4$ | DMSO | 120 | 83 |
| 4 | CuTc | 10 | K$_3$PO$_4$ | DMSO | 120 | 43 |
| 5 | Cu(OAc)$_2$ | 10 | K$_3$PO$_4$ | DMSO | 120 | 56 |
| 6 | CuSO$_4$ | 10 | K$_3$PO$_4$ | DMSO | 120 | 52 |
| 7 | CuBr$_2$ | 10 | K$_3$PO$_4$ | DMSO | 120 | 49 |
| 8 | CuCl$_2$ | 10 | K$_3$PO$_4$ | DMSO | 120 | 60 |
| 9 | Cu$_2$O | 10 | K$_3$PO$_4$ | DMSO | 120 | 67 |
| 10 | CuI | 10 | K$_2$CO$_3$ | DMSO | 120 | 48 |
| 11 | CuI | 10 | Cs$_2$CO$_3$ | DMSO | 120 | 61 |
| 12 | CuI | 10 | Na$_2$CO$_3$ | DMSO | 120 | 38 |

-continued

| No. | Copper salt | X | Base | Solvent | Temperature/° C. | Yield/% |
|---|---|---|---|---|---|---|
| 13 | CuI | 10 | KHCO$_3$ | DMSO | 120 | 31 |
| 14 | CuI | 10 | NaHCO$_3$ | DMSO | 120 | 29 |
| 15 | CuI | 10 | K$_3$PO$_4$ | DMA | 120 | 79 |
| 16 | CuI | 10 | K$_3$PO$_4$ | DMF | 120 | 86 |
| 17 | CuI | 10 | K$_3$PO$_4$ | NMP | 120 | 62 |
| 18 | CuI | 10 | K$_3$PO$_4$ | MeCN | 120 | 49 |
| 19 | CuI | 10 | K$_3$PO$_4$ | 1,4-dioxane | 120 | 33 |
| 20 | CuI | 10 | K$_3$PO$_4$ | THF | 120 | 30 |
| 21 | CuI | 5 | K$_3$PO$_4$ | DMSO | 120 | 90 |
| 22 | CuI | 2.5 | K$_3$PO$_4$ | DMSO | 120 | 81 |
| 23 | CuI | 1 | K$_3$PO$_4$ | DMSO | 120 | 54 |
| 24 | CuI | 10 | K$_3$PO$_4$ | DMSO | 110 | 63 |
| 25 | CuI | 10 | K$_3$PO$_4$ | DMSO | 100 | 38 |
| 26[a] | CuI | 2.5 | K$_3$PO$_4$ | DMSO | 120 | 81 |

[a] the reaction was enlarged to a 5 mmol scale by using L-II-31 as a ligand, while benzylamine was reduced to 1.3 equivalents, CuI was reduced to 2.5 mol %, ligand was reduced to 5 mol %, and potassium phosphate was reduced to 1.0 equivalents. The amount of DMSO was 2 mL, and the reaction time was extended to 41 hours.

Figure 3:
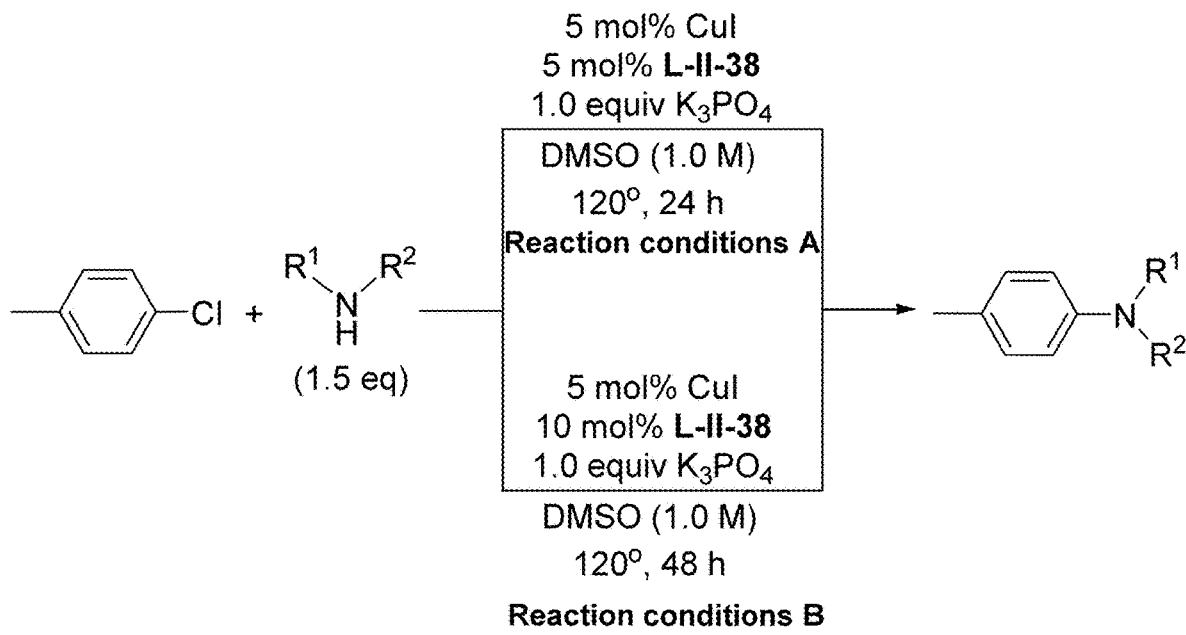

Example 5 Synthesis of the Corresponding Aniline Derivatives by the Coupling Reaction of 1-chloro-4-methylbenzene with Various Primary and Secondary Amines A schematic of this coupling reaction of 1-chloro-4-methylbenzene with various primary and secondary amines of Example 5 is shown in FIG. 3.

Copper iodide (0.05 mmol), ligand L-II-38 (0.05 or 0.1 mmol), potassium phosphate (1.0 mmol) were added into a 10 mL of Schlenk tube. The tube was then evacuated and backfilled with argon (this sequence was repeated three times), and then 1-chloro-4-methylbenzene (1.0 mmol), amine (1.5 mmol) and 1 mL of DMSO were added. The reaction mixture was stirred well at 120° C. for 24 or 48 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography to give the product N-p-methylphenyl amine.

Different amines were used in this example, including primary, secondary aliphatic amines and aromatic amines. The reaction conditions included A and B. Conditions A were for the more reactive amines and conditions B were for the less reactive amines. The results are shown in the table below.

| Product, Reaction conditions and Yield | Characterization data of product |
|---|---|
| 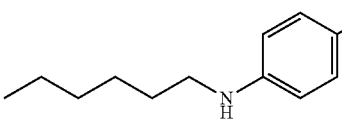 reaction condition A, 90% | $^1$H NMR (500 MHz, CDCl$_3$) δ 7.07 (d, J = 8.1 Hz, 2H), 6.61 (d, J = 8.4 Hz, 2H), 3.42 (br s, 1H), 3.16 (t, J = 7.2 Hz, 2H), 2.33 (s, 3H), 1.68 (p, J = 7.2 Hz, 2H), 1.53-1.34 (m, 6H), 1.00 (t, J = 6.8 Hz, 3H); $^{13}$C NMR (125 MHz, CDCl$_3$) δ 146.25, 129.60, 126.11, 112.81, 44.31, 31.62, 29.54, 26.82, 22.58, 20.28, 13.98; LC-MS (ESI, m/z): 192.1 (M + H)$^+$. |
| 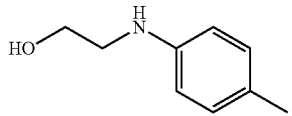 reaction condition A, 82% | $^1$H NMR (400 MHz, CDCl$_3$) δ 7.00 (d, J = 7.9 Hz, 1H), 6.60 (d, J = 8.4 Hz, 2H), 3.83 (t, J = 5 Hz, 2H), 3.29 (t, J = 5 Hz, 2H), 2.25 (s, 3H); $^{13}$C NMR (100 MHz, CDCl$_3$) δ 145.67, 129.68, 127.15, 113.46, 61.02, 46.42, 20.30; LC-MS (ESI, m/z): 152.1 (M + H)$^+$. |
| 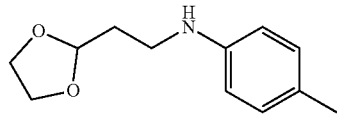 reaction condition A, 84% | $^1$H NMR (400 MHz, CDCl$_3$) δ 6.99 (d, J = 8.0 Hz, 2H), 6.56 (d, J = 8.0 Hz, 2H), 4.99 (t, J = 4.5 Hz, 1H), 4.06-3.95 (m, 2H), 3.92-3.80 (m, 2H), 3.25 (t, J = 6.5 Hz, 2H), 2.23 (s, 3H), 2.01 (td, J = 6.5, 4.5 Hz, 2H); $^{13}$C NMR (100 MHz, CDCl$_3$) δ 146.00, 129.55, 126.27, 112.90, 103.59, 64.77, 39.45, 32.92, 20.26; HRMS (DART) calcd. for C$_{12}$H$_{18}$NO$_2$ (M + H)$^+$: 208.1332, Found: 208.1333. |
| 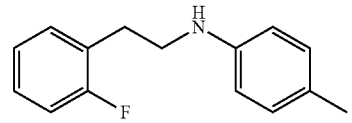 reaction condition A, 83% | $^1$H NMR (400 MHz, CDCl$_3$) δ 7.27-7.17 (m, 2H), 7.13-7.00 (m, 2H), 7.00 (d, J = 8.1 Hz, 2H), 6.57 (d, J = 8.4 Hz, 2H), 3.60 (br s, 1H), 3.39 (t, J = 7.1 Hz, 2H), 2.95 (td, J = 7.1, 1.1 Hz, 2H), 2.25 (s, 3H); $^{13}$C NMR (100 MHz, CDCl$_3$) δ 161.18 (d, J = 244.8 Hz), 145.50, 130.94 (d, J = 5.0 Hz), 129.66, 127.98 (d, J = 8.1 Hz), 126.41, 126.24 (d, J = 16.0 Hz), 123.96 (d, J = 3.6 Hz), 115.21 (d, J = 22.2 Hz), 112.96, 44.04, 28.99 (d, J = 1.8 Hz), 20.26; HRMS (DART) calcd. for C$_{15}$H$_{17}$NF (M + H)$^+$: 230.1340, Found: 230.1340. |

| Product, Reaction conditions and Yield | Characterization data of product |
|---|---|
| 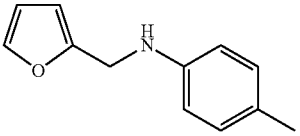<br>reaction condition A,<br>86% | $^1$H NMR (400 MHz, CDCl$_3$) δ 7.36 (dd, J = 1.9. 0.9 Hz, 1H), 7.00 (d, J = 7.8 Hz, 2H), 6.61 (d, J = 8.4 Hz, 2H), 6.32 (dd, J = 3.2, 1.8 Hz, 1H), 6.23 (dd, J = 3.2, 0.9 Hz, 1H), 4.30 (s, 2H), 3.89 (br s, 1H), 2.25 (s, 3H); $^{13}$C NMR (100 MHz, CDCl$_3$) δ 152.89, 145.26, 141.70, 129.60, 127.08, 113.24, 110.21, 106.77, 41.63, 20.31; LC-MS (ESI, m/z): 188.1 (M + H)$^+$. |
| 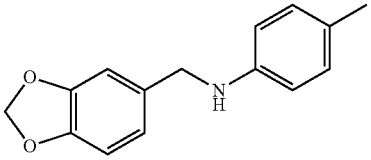<br>reaction condition A,<br>88% | $^1$H NMR (400 MHz, CDCl$_3$) δ 6.99 (d, J = 8.3 Hz, 2H), 6.90-6.74 (m, 3H), 6.56 (d, J = 8.3 Hz, 2H), 5.95 (s, 2H), 4.22 (s, 2H), 3.86 (br s, 1H), 2.25 (s, 3H); $^{13}$C NMR (100 MHz, CDCl$_3$) δ 147.78, 146.57, 145.74, 133.52, 129.66, 126.68, 120.46, 112.94, 108.18, 107.96, 100.88, 48.34, 20.32; HRMS (DART) calcd. for C$_{15}$H$_{16}$NO$_2$ (M + H)$^+$: 242.1176, Found: 242.1175. |
| 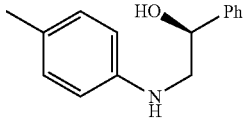<br>reaction condition A,<br>46% | $^1$H NMR (400 MHz, CDCl$_3$) δ 7.45-7.36 (m, 4H), 7.36-7.29 (m, 1H), 7.01 (d, J = 8.0 Hz, 2H), 6.62 (d, J = 8.4 Hz, 2H), 4.92 (dd, J = 8.7, 3.8 Hz, 1H), 3.42 (dd, J = 13.1, 3.9 Hz, 1H), 3.28 (dd, J = 13.1, 8.7 Hz, 1H), 2.25 (s, 3H); $^{13}$C NMR (125 MHz, CDCl$_3$) δ 145.48, 142.07, 129.76, 128.52, 127.85, 127.37, 125.83, 113.68, 72.31, 52.19, 20.35; HRMS (ESI) calcd. for C$_{15}$H$_{18}$NO (M + H)$^+$: 228.1383, Found: 228.1384. |
| 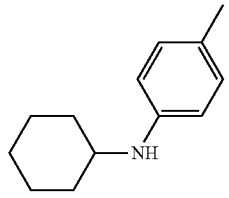<br>reaction condition A,<br>72%<br>reaction condition B,<br>83% | $^1$H NMR (400 MHz, CDCl$_3$) δ 1.05-1.48 (m, 8H), 2.02-2.06 (m, 2H), 2.17 (s, 3H), 3.18-3.25 (m, 1H), 3.36 (s, 1H), 6.52 (d, J = 8.2 Hz, 2H), 6.96 (d, J = 8.1 Hz, 2H); $^{13}$C NMR (100 MHz, CDCl$_3$) δ 145.22, 129.85, 126.20, 113.59, 52.16, 33.67, 26.11, 25.18, 20.49; LC-MS (ESI, m/z): 190.1 (M + H)$^+$. |
| 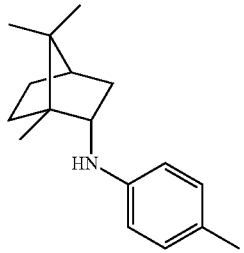<br>reaction condition B,<br>68% | $^1$H NMR (400 MHz, CDCl$_3$) δ 6.96 (d, J = 7.9 Hz, 2H), 6.52 (d, J = 8.4 Hz, 2H), 3.55 (ddd, J = 10.0, 4.2, 2.0 Hz, 2H), 2.47-2.31 (m, 1H), 2.23 (s, 3H), 1.86-1.67 (m, 3H), 1.46-1.31 (m, 1H), 1.28-1.16 (m, 1H), 0.97 (s, 3H), 0.93-0.86 (m, 7H); $^{13}$C NMR (100 MHz, CDCl$_3$) δ 146.75, 129.74, 125.99, 113.28, 58.70, 49.46, 48.17, 45.15, 38.91, 28.36, 27.87, 20.45, 19.97, 18.86, 14.43; HRMS (DART) calcd. for C$_{17}$H$_{26}$N (M + H)$^+$: 244.2060, Found: 244.2059. |
| 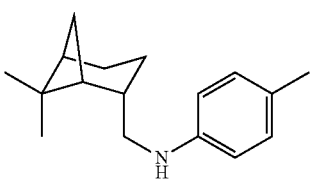<br>reaction condition B,<br>91% | $^1$H NMR (400 MHz, CDCl$_3$) δ 6.98 (d, J = 7.8 Hz, 2H), 6.52 (d, J = 8.4 Hz, 2H), 3.51 (br, 1H), 3.22-3.00 (m, 2H), 2.53-2.26 (m, 2H), 2.23 (s, 3H), 2.14-1.80 (m, 5H), 1.69-1.44 (m, 1H), 1.20 (s, 3H), 1.04 (s, 3H), 0.92 (d, J = 9.6 Hz, 1H); $^{13}$C NMR (100 MHz, CDCl$_3$) δ 146.39, 129.78, 126.20, 112.95, 50.45, 44.28, 41.57, 41.20, 38.82, 33.54, 28.17, 26.28, 23.45, 20.50, 20.48; HRMS (DART) calcd. for C$_{17}$H$_{26}$N (M + H)$^+$: 244.2060, Found: 244.2060. |

| Product, Reaction conditions and Yield | Characterization data of product |
|---|---|
| 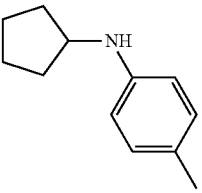<br>reaction condition B,<br>85% | $^1$H NMR (400 MHz, CDCl$_3$) δ 6.98 (d, J = 7.7 Hz, 2H), 6.54 (d, J = 7.7 Hz, 2H), 3.77 (ddd, J = 12.3, 6.8, 5.5 Hz, 1H), 3.49 (br, 1H), 2.24 (s, 3H), 2.01 (m, 2H), 1.78-1.67 (m, 2H), 1.66-1.54 (m, 2H), 1.51-1.39 (m, 2H); $^{13}$C NMR (100 MHz, CDCl$_3$) δ 145.89, 129.76, 126.19, 113.49, 55.04, 33.68, 24.19, 20.48; LC-MS (ESI, m/z): 176.1 (M + H)$^+$. |
| 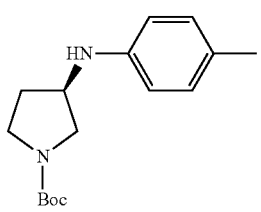<br>reaction condition B,<br>76% | $^1$H NMR (400 MHz, CDCl$_3$) δ 7.00 (d, J = 7.5 Hz, 2H), 6.54 (d, J = 8.4 Hz, 2H), 4.01 (s, 1H), 3.78-3.34 (m, 4H), 3.21 (m, 1H), 2.24 (s, 3H), 2.17 (m, 1H), 1.88 (s, 1H), 1.46 (s, 9H); $^{13}$C NMR (100 MHz, CDCl$_3$) δ 154.73, 144.68, 129.93, 127.17, 113.50, 79.49, 53.36, 52.65, 52.24, 51.98, 44.24, 43.91, 31.95, 31.32, 28.61, 20.46; HRMS (DART) calcd. for C$_{16}$H$_{25}$N$_2$O$_2$ (M + H)$^+$: 277.1911, Found: 277.1910. (Note: Rotary isomers exists, leading to the higher peak in the is wider peak in the upperfield of $^1$H NMR spectrum, and the double peak of single carbon atom in the upperfield of 13C NMR spectrum) |
| 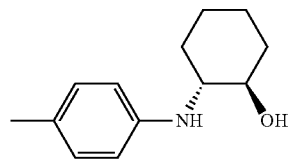<br>reaction condition B,<br>65% | $^1$H NMR (400 MHz, CDCl$_3$) δ 6.90 (d, J = 7.8 Hz, 2H), 6.54 (d, J = 8.4 Hz, 2H), 3.23 (ddd, 1H), 2.99 (ddd, 1H), 2.75 (br, 1H), 2.14 (s, 3H), 2.06-1.95 (m, 2H), 1.71-1.65 (m, 1H), 1.64-1.55 (m, 1H), 1.35-1.17 (m, 3H), 1.00-0.85 (m, 1H), 0.82-0.68 (m, 1H). $^{13}$C NMR (125 MHz, CDCl$_3$) δ 145.52, 129.93, 127.90, 114.91, 77.41, 77.16, 76.91, 74.61, 60.83, 33.23, 31.69, 25.20, 24.42, 20.50; HRMS (DART) calcd. for C$_{13}$H$_{20}$NO (M + H)$^+$: 206.1539, Found: 206.1539. |
| 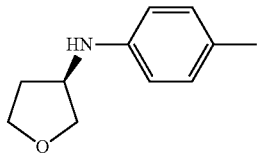<br>reaction condition B,<br>74% | $^1$H NMR (400 MHz, CDCl$_3$) δ 7.00 (d, J = 7.8 Hz, 2H), 6.53 (d, J = 8.4 Hz, 2H), 4.13-4.03 (m, 1H), 4.00-3.90 (m, 2H), 3.88-3.80 (m, 1H), 3.74-3.66 (m, 1H), 2.30-2.19 (m, 4H), 1.94-1.79 (m, 1H); $^{13}$C NMR (100 MHz, CDCl$_3$) δ 144.83, 129.79, 126.89, 113.53, 73.69, 67.05, 54.06, 33.17, 20.36; HRMS (ESI) calcd. for C$_{11}$H$_{16}$NO (M + H)$^+$: 178.1226, Found: 178.1229. |
| 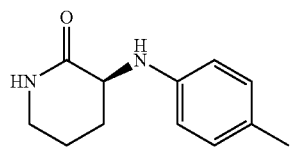<br>reaction condition B,<br>25% | $^1$H NMR (400 MHz, CDCl$_3$) δ 7.00 (d, J = 8.2 Hz, 2H), 6.60 (d, J = 8.4 Hz, 2H), 3.81 (dd, J = 11.0, 5.5 Hz, 1H), 3.38 (t, J = 5.3 Hz, 2H), 2.54-2.43 (m, 1H), 2.24 (s, 3H), 2.03-1.92 (m, 2H), 1.71-1.59 (m, 2H), 1.25 (s, 1H); $^{13}$C NMR (125 MHz, CDCl$_3$) δ 173.10, 145.14, 129.76, 127.29, 113.87, 54.46, 41.79, 27.94, 20.89, 20.45; HRMS (DART) calcd. for C$_{12}$H$_{17}$N$_2$O (M + H)$^+$: 205.1335, Found: 205.1336. |
| 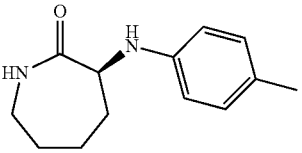<br>reaction condition B,<br>24% | $^1$H NMR (400 MHz, CDCl$_3$) δ 6.89 (d, J = 7.7 Hz, 2H), 6.38 (d, J = 8.4 Hz, 2H), 5.96 (s, 1H), 4.95 (s, 1H), 3.91 (d, J = 10.2 Hz, 1H), 3.26-3.12 (m, 2H), 2.13 (s, 3H), 2.05-1.92 (m, 2H), 1.84-1.66 (m, 2H), 1.46-1.33 (m, 2H); $^{13}$C NMR (125 MHz, CDCl$_3$) δ 177.22, 144.06, 129.85, 126.22, 113.03, 55.61, 42.21, 30.91, 29.06, 28.01, 20.40; HRMS (DART) calcd. for C$_{13}$H$_{19}$N$_2$O (M + H)$^+$: 219.1492, Found: 219.1491. |
| 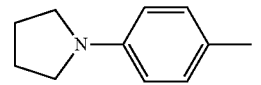<br>reaction condition B,<br>50% | $^1$H NMR (400 MHz, CDCl$_3$) δ 7.06 (d, J = 8.2 Hz, 2H), 6.52 (d, J = 8.2 Hz, 2H), 3.25 (dd, J = 6.4, 6.4 Hz, 4H), 2.24 (s, 3H), 1.98 (dd, J = 6.4, 6.4 Hz, 4H); $^{13}$C NMR (100 MHz, CDCl$_3$) δ 146.1, 129.6, 124.4, 111.8, 47.8, 25.4, 20.2; LC-MS (ESI, m/z): 162.1 (M + H)$^+$. |

| Product, Reaction conditions and Yield | Characterization data of product |
|---|---|
| 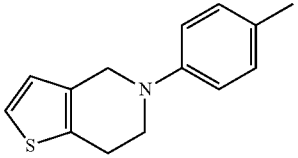<br>reaction condition B,<br>17% | $^1$H NMR (400 MHz, CDCl3) δ 7.12 (d, J = 5.2 Hz, 1H), 7.10 (d, J = 8.4 Hz, 2H), 6.93 (d, J = 8.8 Hz, 2H), 6.83 (d, J = 5.2 Hz, 1H), 4.26 (s, 2H), 3.57 (t, J = 5.6 Hz, 2H), 2.98 (t, J = 5.6 Hz, 2H), 2.28 (s, 3H); $^{13}$C NMR (100 MHz, CDCl3) δ 148.60, 133.56, 133.36, 129.67, 128.87, 125.09, 122.77, 116.53, 49.44, 48.05, 25.31, 20.38; HRMS (ESI) calcd. for $C_{14}H_{16}NS$ (M + H)$^+$: 230.0998, Found: 230.0999. |
| 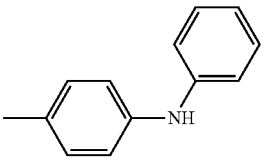<br>reaction condition B,<br>32% | $^1$H NMR (400 MHz, CDCl$_3$) δ 7.24-7.20 (m, 2H), 7.07 (d, J = 8.2 Hz, 2H), 7.01-6.98 (m, 4H), 6.87 (t, J = 7.3 Hz, 1H), 5.58 (br s, 1H), 2.30 (s, 3H); $^{13}$C NMR (100 MHz, CDCl$_3$) δ 143.9, 140.2, 130.9, 129.8, 129.3, 120.3, 118.9, 116.8, 20.7; LC-MS (ESI, m/z): 184.3 (M + H)$^+$. |

Example 6 Synthesis of N-benzylaniline Derivatives by Coupling Reaction of Aryl Chloride with Benzylamine

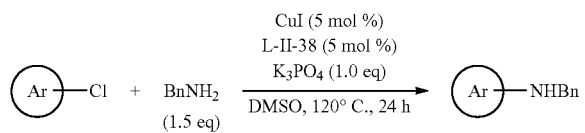

Copper iodide (0.05 mmol), ligand L-II-38 (0.05 mmol) and potassium phosphate (1.0 mmol) were added into a 10 mL of Schlenk tube. The tube was then evacuated and backfilled with argon (this sequence was repeated three times), and then aryl chloride (1.0 mmol), benzylamine (1.5 mmol) and 1 mL of DMSO were added. The reaction mixture was stirred well at 120° C. for 24 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography to give the product N-benzylaniline derivatives.

This example used different aryl chlorides. The results are given in the following table.

| Product and Yield | Characterization data of product |
|---|---|
| 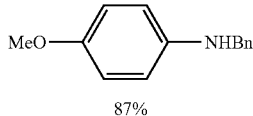<br>87% | $^1$H NMR (400 MHz, CDCl$_3$) δ 7.42-7.31 (m, 4H), 7.30-7.26 (m, 1H), 6.78 (d, J = 8.9 Hz, 2H), 6.61 (d, J = 8.9 Hz, 2H), 4.29 (s, 2H), 3.75 (s, 3H); 13C NMR (101 MHz, CDCl$_3$) δ 152.2, 142.5, 139.7, 128.6, 127.6, 127.2, 114.9, 114.1, 55.8, 49.2; HRMS (ESI) calcd. for $C_{14}H_{16}NO$ (M + H)$^+$: 214.1232, Found: 214.1237. |
| 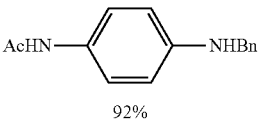<br>92% | $^1$H NMR (400 MHz, CDCl$_3$) δ 7.39-7.30 (m, 5H), 7.30-7.26 (m, 1H), 7.25-7.21 (m, 2H), 7.04-6.88 (m, 1H), 6.63-6.55 (m, 2H), 4.31 (s, 2H), 4.02 (s, 1H), 2.13 (s, 3H); $^{13}$C NMR (125 MHz, CDCl$_3$) δ 168.26, 145.51, 139.45, 128.76, 128.39, 127.58, 127.37, 122.52, 113.17, 48.66, 24.40; HRMS (ESI) calcd. for $C_{15}H_{17}N_2O$ (M + H)$^+$: 241.1341. Found: 241.1337. |
| 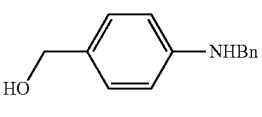<br>85% | $^1$H NMR (400 MHz, CDCl$_3$) δ 7.41-7.31 (m, 4H), 7.31-7.27 (m, 1H), 7.18 (d, J = 8.4 Hz, 2H), 6.63 (d, J = 8.4 Hz, 2H), 4.55 (s, 2H), 4.34 (s, 2H), 4.10 (s, 1H): $^{13}$C NMR (125 MHz, CDCl$_3$) δ 147.99, 139.38, 130.06, 129.00, 128.79, 127.57, 127.40, 112.97, 65.57, 48.43; HRMS (ESI) calcd. for $C_{14}H_{16}NO$ (M + H)$^+$: 214.1232, Found: 214.1225. |
| 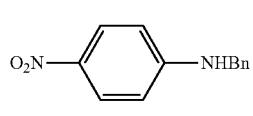<br>77% | $^1$H NMR (400 MHz, CDCl$_3$) δ 7.41-7.31 (m, 4H), 7.31-7.27 (m, 1H), 7.18 (d, J = 8.4 Hz, 2H), 6.63 (d, J = 8.4 Hz, 2H), 4.55 (s, 2H), 4.34 (s, 2H), 4.10 (s, 1H); $^{13}$C NMR (125 MHz, CDCl$_3$) δ 147.99, 139.38, 130.06, 129.00, 128.79, 127.57, 127.40, 112.97, 65.57, 48.43; HRMS (ESI) calcd. for $C_{13}H_{13}N_2O_2$ (M + H)$^+$: 229.0977, Found: 229.0970. |

| Product and Yield | Characterization data of product |
|---|---|
| 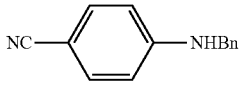<br>91% | $^1$H NMR (400 MHz, CDCl$_3$) δ 7.45-7.39 (m, 2H), 7.39-7.28 (m, 5H), 6.59 (d, J = 8.8 Hz, 2H), 4.61 (s, 1H), 4.38 (d, J = 5.5 Hz, 2H); $^{13}$C NMR (125 MHz, CDCl$_3$) δ 151.21, 137.92, 133.86, 129.00, 127.84, 127.45, 120.48, 112.54, 99.07, 47.65; HRMS (ESI) calcd. for C$_{14}$H$_{13}$N$_2$ (M + H)$^+$: 209.1079, Found: 209.1072. |
| <br>73% | $^1$H NMR (400 MHz, CDCl$_3$) δ 7.45-7.35 (m, 6H), 7.35-7.27 (m, 1H), 6.64 (d, J = 7.8 Hz, 2H), 4.38 (s, 3H); $^{13}$C NMR (125 MHz, CDCl$_3$) δ 150.59, 138.58, 128.93, 127.66, 127.50, 126.76 (q, J = 3.8 Hz), 125.09 (q, J = 270.3 Hz), 119.20 (q, J = 32.6 Hz), 112.12, 47.95; HRMS (ESI) calcd. for C$_{14}$H$_{13}$F$_3$N (M + H)$^+$: 252.1000, Found: 252.1007. |
| <br>82% | $^1$H NMR (400 MHz, CDCl$_3$) δ 7.82 (d, J = 8.7 Hz, 2H), 7.39-7.33 (m, 4H), 7.32-7.27 (m, 1H), 6.60 (d, J = 8.7 Hz, 2H), 4.58 (s, 1H), 4.41 (s, 2H), 2.49 (s, 3H): $^{13}$C NMR (100 MHz, CDCl$_3$) δ 196.2, 152.0, 138.3, 130.8, 129.0, 127.6, 127.4, 127.2, 111.6, 47.7, 26.0; HRMS (ESI) calcd. for C$_{15}$H$_{16}$NO (M + H)$^+$: 226.1232, Found: 226.1227. |
| 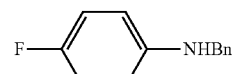<br>92% | $^1$H NMR (400 MHz, CDCl$_3$) δ 7.40-7.33 (m, 4H), 7.32-7.27 (m, 1H), 6.95-6.83 (m, 2H), 6.62-6.52 (m, 2H), 4.30 (s, 2H), 3.94 (s, 1H); $^{13}$C NMR (125 MHz, CDCl$_3$) δ 156.02 (d, J = 235.0 Hz), 144.61, 139.37, 128.80, 127.62, 127.44, 115.80 (d, J = 22.4 Hz), 113.77 (d, J = 7.5 Hz), 49.08; HRMS (ESI) calcd. for C$_{13}$H$_{13}$FN (M + H)$^+$: 202.1032, Found: 202.1037. |
| 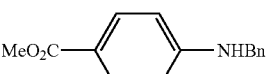<br>60% | $^1$H NMR (400 MHz, CDCl$_3$) δ 7.86 (d, J = 8.8 Hz, 2H), 7.40-7.32 (m, 4H), 7.32-7.27 (m, 1H), 6.59 (d, J = 8.8 Hz, 2H), 4.49 (s, 1H), 4.39 (s, 2H), 3.85 (s, 3H); $^{13}$C NMR (125 MHz, CDCl$_3$) δ 167.2, 151.8, 131.7, 131.6, 128.5, 127.5, 118.8, 111.7, 51.5, 47.7; HRMS (ESI) calcd. for C$_{15}$H$_{16}$NO$_2$ (M + H)$^+$: 242.1181, Found: 242.1183. |
| 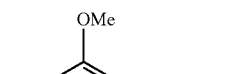<br>97% | $^1$H NMR (400 MHz, CDCl$_3$) δ 7.42-7.32 (m, 4H), 7.32-7.26 (m, 1H), 7.13-7.06 (m, 1H), 6.33-6.25 (m, 2H), 6.23-6.19 (m, 1H), 4.33 (s, 2H), 4.06 (s, 1H), 3.76 (s, 3H); $^{13}$C NMR (125 MHz, CDCl$_3$) δ 160.94, 149.67, 139.44, 130.12, 128.76, 127.64, 127.37, 106.10, 102.80, 98.99, 55.19, 48.45; HRMS (ESI) calcd. for C$_{14}$H$_{16}$NO (M + H)$^+$: 214.1232, Found: 214.1230. |
| 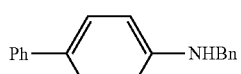<br>96% | $^1$H NMR (400 MHz, CDCl$_3$) δ 7.59-7.50 (m, 2H), 7.50-7.42 (m, 2H), 7.44-7.34 (m, 6H), 7.38-7.22 (m, 3H), 6.72 (d, J = 8.5 Hz, 2H), 4.39 (s, 2H), 4.30-3.71 (m, 1H); $^{13}$C NMR (125 MHz, CDCl$_3$) δ 147.61, 141.34, 139.38, 130.68, 128.81, 128.77, 128.09, 127.64, 127.44, 126.43, 126.21, 113.29, 48.50; HRMS (ESI) calcd. for C$_{19}$H$_{18}$N (M + H)$^+$: 260.1439, Found: 260.1433. |
| 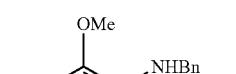<br>82% | $^1$H NMR (400 MHz, CDCl$_3$) δ 7.45-7.32 (m, 4H), 7.32-7.26 (m, 1H), 6.90-6.78 (m, 2H), 6.74-6.66 (m, 1H), 6.62 (dd, J = 7.8, 1.6 Hz, 1H), 4.65 (s, 1H), 4.37 (s, 2H), 3.87 (s, 3H); $^{13}$C NMR (125 MHz, CDCl$_3$) δ 146.88, 139.69, 138.23, 128.68, 127.62, 127.22, 121.38, 116.73, 110.17, 109.49, 55.51, 48.15; HRMS (ESI) calcd. for C$_{14}$H$_{16}$NO (M + H)$^+$: 214.1232, Found: 214.1228. |
| 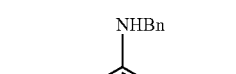<br>97% | $^1$H NMR (400 MHz, CDCl$_3$) δ 7.41-7.31 (m, 4H), 7.31-7.26 (m, 1H), 5.90 (t, J = 2.1 Hz, 1H), 5.84 (d, J = 2.1 Hz, 2H), 4.31 (s, 2H), 4.06 (s, 1H), 3.74 (s, 6H); $^{13}$C NMR (125 MHz, CDCl$_3$) δ 161.83, 150.20, 139.36, 128.76, 127.66, 127.39, 91.84, 90.02, 55.27, 48.47; HRMS (ESI) calcd. for C$_{15}$H$_{18}$NO$_2$ (M + H)$^+$: 244.1338, Found: 244.1330. |

-continued

| Product and Yield | Characterization data of product |
|---|---|
| 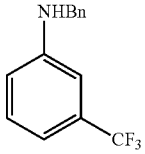<br>70% | ¹H NMR (400 MHz, CDCl₃) δ 7.32-7.26 (m, 4H), 7.25-7.18 (m, 1H), 7.17-7.13 (m, 1H), 6.87 (d, J = 7.7 Hz, 1H), 6.77 (s, 1H), 6.67 (dd, J = 8.2, 2.4 Hz, 1H), 4.27 (s, 2H), 4.15 (s, 1H); ¹³C NMR (100 MHz, CDCl₃) δ 148.2, 138.5, 131.6 (q, J = 31 Hz), 129.6, 128.7, 127.5, 126.3, 122.3, 115.70 (q, J = 1.1 Hz), 113.94 (q, J = 3.9 Hz), 109.08 (q, J = 3.9 Hz), 48.09; HRMS (ESI) calcd. for C₁₄H₁₃F₃N (M + H)⁺: 252.1000, Found: 252.1007. |
| 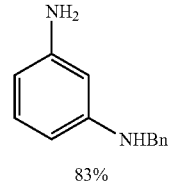<br>83% | ¹H NMR (400 MHz, CDCl₃) δ 7.42-7.31 (m, 4H), 7.31-7.26 (m, 1H), 6.97 (t, J = 7.9 Hz, 1H), 6.17-6.05 (m, 2H), 5.98 (t, J = 2.2 Hz, 1H), 4.30 (s, 2H), 3.67 (s, 3H); ¹³C NMR (125 MHz, CDCl₃) δ 149.37, 147.52, 139.58, 130.11, 128.60, 127.48, 127.17, 105.07, 104.05, 99.46, 48.28; HRMS (ESI) calcd. for C₁₃H₁₅N₂ (M + H)⁺: 199.1235, Found: 199.1240. |
| 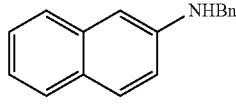<br>97% | ¹H NMR (400 MHz, CDCl₃) δ 7.69 (d, J = 8.1 Hz, 1H), 7.65 (d, J = 8.8 Hz, 1H), 7.61 (d, J = 8.1 Hz, 1H), 7.46-7.41 (m, 2H), 7.41-7.34 (m, 3H), 7.34-7.28 (m, 1H), 7.24-7.18 (m, 1H), 6.93 (dd, J = 8.8, 2.3 Hz, 1H), 6.86 (d, J = 2.3 Hz, 1H), 4.45 (s, 2H), 4.20 (s, 1H); ¹³C NMR (125 MHz, CDCl₃) δ 145.55, 139.02, 135.13, 128.97, 128.69, 127.67, 127.64, 127.36, 126.33, 126.02, 122.13, 117.90, 104.93, 48.49; HRMS (ESI) calcd. for C₁₇H₁₆N (M + H)⁺: 234.1283, Found: 234.1278. |
| 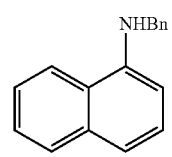<br>79% | ¹H NMR (400 MHz, CDCl₃) δ 7.76-7.64 (m, 2H), 7.38-7.30 (m, 4H), 7.30-7.24 (m, 2H), 7.24-7.13 (m, 3H), 6.52 (d, J = 7.4 Hz, 1H), 4.58 (s, 1H), 4.38 (s, 2H); ¹³C NMR (125 MHz, CDCl₃) δ 143.32, 139.21, 134.41, 128.84, 128.82, 127.85, 127.51, 126.73, 125.86, 124.86, 123.49, 120.01, 117.75, 104.86, 48.71; HRMS (ESI) calcd. for C₁₇H₁₆N (M + H)⁺: 234.1283, Found: 234.1280. |
| 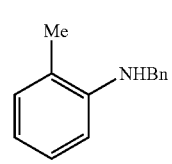<br>50% | ¹H NMR (400 MHz, CDCl₃) δ 7.43-7.34 (m, 4H), 7.33-7.27 (m, 1H), 7.15-7.06 (m, 2H), 6.73-6.66 (m, 1H), 6.63 (dd, J = 8.0, 1.2 Hz, 1H), 4.39 (s, 2H), 3.88 (s, 1H), 2.18 (s, 3H); ¹³C NMR (125 MHz, CDCl₃) δ 146.19, 139.62, 130.20, 128.79, 127.67, 127.38, 127.29, 122.05, 117.30, 110.09, 48.44, 17.70; HRMS (ESI) calcd. for C₁₄H₁₆N (M + H)⁺: 198.1283, Found: 198.1285. |
| 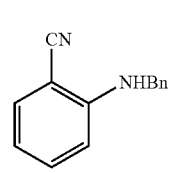<br>64% | ¹H NMR (400 MHz, CDCl₃) δ 7.44-7.40 (m, 1H), 7.40-7.27 (m, 6H), 6.70 (t, J = 7.5 Hz, 1H), 6.64 (d, J = 8.5 Hz, 1H), 5.05 (t, J = 5.7 Hz, 1H), 4.44 (d, J = 5.5 Hz, 2H); ¹³C NMR (125 MHz, CDCl₃) δ 150.05, 137.70, 134.26, 132.75, 128.86, 127.64, 127.16, 117.86, 116.86, 111.03, 95.94, 47.48; HRMS (ESI) calcd. for C₁₄H₁₃N₂ (M + H)⁺: 209.1079, Found: 209.1070. |
| 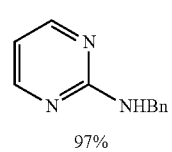<br>97% | ¹H NMR (400 MHz, CDCl₃) δ 8.37-8.03 (m, 2H), 7.40-7.30 (m, 4H), 7.30-7.26 (m, 1H), 6.60-6.42 (m, 1H), 5.98 (s, 1H), 4.64 (d, J = 5.8 Hz, 2H); ¹³C NMR (125 MHz, CDCl₃) δ 162.42, 158.09, 139.20, 128.67, 127.69, 127.30, 110.70, 45.57; HRMS (ESI) calcd. for C₁₁H₁₂N₃ (M + H)⁺: 186.1031, Found: 186.1025. |
| 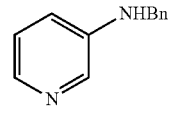<br>96% | ¹H NMR (400 MHz, CDCl₃) δ 8.07 (d, J = 2.9 Hz, 1H), 8.02-7.90 (m, 1H), 7.35 (d, J = 4.4 Hz, 4H), 7.32-7.26 (m, 1H), 7.11-7.01 (m, 1H), 6.91-6.81 (m, 1H), 4.34 (d, J = 4.8 Hz, 2H), 4.19 (s, 1H); ¹³C NMR (125 MHz, CDCl₃) δ 144.22, 138.82, 138.62, 136.18, 128.79, 127.50, 127.44, 123.81, 118.55, 47.86; HRMS (ESI) calcd. for C₁₂H₁₃N₂ (M + H)⁺: 185.1079, Found: 185.1083. |

-continued

| Product and Yield | Characterization data of product |
|---|---|
| 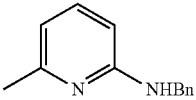 66% | $^1$H NMR (400 MHz, CDCl$_3$) δ 7.39-7.30 (m, 4H), 7.30-7.24 (m, 2H), 6.47 (d, J = 7.3 Hz, 1H), 6.17 (d, J = 8.3 Hz, 1H), 4.93 (s, 1H), 4.46 (d, J = 5.8 Hz, 2H), 2.39 (s, 3H); $^{13}$C NMR (125 MHz, CDCl$_3$) δ 158.36, 157.02, 139.23, 137.93, 128.58, 127.33, 127.17, 112.53, 102.86, 46.57, 24.35; HRMS (ESI) calcd. for C$_{13}$H$_{15}$N$_2$ (M + H)$^+$: 199.1235, Found: 199.1228. |
| 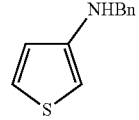 49% | $^1$H NMR (400 MHz, CDCl$_3$) δ 7.43-7.32 (m, 4H), 7.32-7.27 (m, 1H), 7.20-7.13 (m, 1H), 6.72-6.58 (m, 1H), 6.04-5.94 (m, 1H), 4.28 (s, 2H), 3.98 (s, 1H); $^{13}$C NMR (125 MHz, CDCl$_3$) δ 148.58, 139.42, 128.73, 127.85, 127.44, 125.32, 120.01, 96.22, 50.79; HRMS (ESI) calcd. for C$_{11}$H$_{12}$NS (M + H)$^+$: 190.0690, Found: 190.0695. |
| 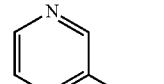 73% | $^1$H NMR (400 MHz, CDCl$_3$) δ 8.00 (dd, J = 2.8, 1.5 Hz, 1H), 7.89 (d, J = 1.5 Hz, 1H), 7.82 (d, J = 2.8 Hz, 1H), 7.38-7.33 (m, 4H), 7.33-7.27 (m, 1H), 4.96 (s, 1H), 4.56 (d, J = 5.7 Hz, 2H); $^{13}$C NMR (125 MHz, CDCl$_3$) δ 154.54, 142.12, 138.55, 133.29, 132.22, 128.90, 127.70, 127.69, 45.71; HRMS (ESI) calcd. for C$_{11}$H$_{12}$N$_3$ (M + H)$^+$: 186.1031, Found: 186.1037. |
| 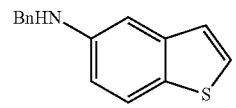 93% | $^1$H NMR (400 MHz, CDCl$_3$) δ 7.64 (d, J = 8.6 Hz, 1H), 7.47-7.40 (m, 2H), 7.40-7.34 (m, 3H), 7.34-7.27 (m, 1H), 7.16 (dt, J = 5.5, 1.0 Hz, 1H), 7.05-6.98 (m, 1H), 6.77 (dd, J = 8.6, 2.3 Hz, 1H), 4.40 (s, 2H), 4.09 (s, 1H); $^{13}$C NMR (125 MHz, CDCl$_3$) δ 145.79, 141.09, 139.50, 129.59, 128.78, 127.65, 127.37, 126.99, 123.50, 122.96, 114.04, 105.09, 48.88; HRMS (ESI) calcd. for C$_{15}$H$_{14}$NS (M + H)$^+$: 240.0847, Found: 240.0842. |
|  80% | $^1$H NMR (400 MHz, CDCl$_3$) δ 8.72 (s, 1H), 7.93 (d, J = 8.3 Hz, 1H), 7.92 (s, 1H), 7.81 (d, J = 8.3 Hz, 1H), 7.69-7.62 (m, 1H), 7.62-7.56 (m, 1H), 7.50-7.43 (m, 2H), 7.42-7.35 (m, 2H), 7.36-7.30 (m, 1H), 4.53 (s, 3H); $^{13}$C NMR (125 MHz, CDCl$_3$) δ 142.56, 138.61, 137.64, 129.15, 128.97, 128.59, 128.20, 127.96, 127.80, 127.08, 126.01, 123.92, 119.30, 48.58; HRMS (ESI) calcd. for C$_{16}$H$_{15}$N$_2$ (M + H)$^+$: 235.1235, Found: 235.1229. |
| 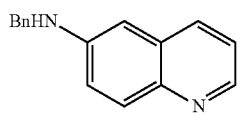 91% | $^1$H NMR (400 MHz, CDCl$_3$) δ 8.61 (dd, J = 4.2, 1.6 Hz, 1H), 7.89 (d, J = 8.9 Hz, 2H), 7.45-7.34 (m, 4H), 7.34-7.28 (m, 1H), 7.25 (dd, J = 8.3, 4.3 Hz, 1H), 7.14 (dd, J = 9.1, 2.6 Hz, 1H), 6.72 (d, J = 2.6 Hz, 1H), 4.44 (d, J = 3.7 Hz, 2H), 4.38 (s, 1H); $^{13}$C NMR (125 MHz, CDCl$_3$) δ 146.42, 146.08, 143.44, 138.81, 134.02, 130.46, 130.21, 128.90, 127.67, 127.61, 121.51, 121.41, 103.44, 48.44; HRMS (ESI) calcd. for C$_{16}$H$_{15}$N$_2$ (M + H)$^+$: 235.1235, Found: 235.1237. |
| 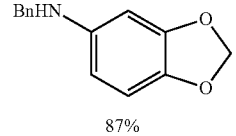 87% | $^1$H NMR (400 MHz, CDCl$_3$) δ 7.40-7.31 (m, 4H), 7.31-7.26 (m, 1H), 6.66 (d, J = 8.3 Hz, 1H), 6.27 (d, J = 2.3 Hz, 1H), 6.08 (dd, J = 8.3, 2.4 Hz, 1H), 5.85 (s, 2H), 4.27 (s, 2H), 3.84 (s, 1H); $^{13}$C NMR (125 MHz, CDCl$_3$) δ 148.33, 143.94, 139.69, 139.40, 128.62, 127.52, 127.24, 108.63, 104.41, 100.57, 96.00, 49.26; HRMS (ESI) calcd. for C$_{14}$H$_{14}$NO$_2$ (M + H)$^+$: 228.1025, Found: 228.1030. |
| 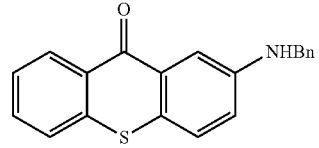 78% | $^1$H NMR (400 MHz, CDCl$_3$) δ 8.61 (dt, J = 8.2, 1.1 Hz, 1H), 7.86 (d, J = 2.7 Hz, 1H), 7.61-7.54 (m, 2H), 7.47-7.42 (m, 1H), 7.42-7.33 (m, 5H), 7.32-7.27 (m, 1H), 7.00 (dd, J = 8.7, 2.7 Hz, 1H), 4.45 (s, 2H), 4.32 (s, 1H); $^{13}$C NMR (125 MHz, CDCl$_3$) δ 180.00, 146.95, 138.75, 137.94, 131.79, 130.30, 129.94, 129.10, 128.86, 127.73, 127.59, 127.02, 126.07, 125.78, 125.39, 120.13, 110.41, 48.33; HRMS (ESI) calcd for C$_{20}$H$_{16}$NOS (M + H)$^+$ 318.0953, found 318.0952. |
| 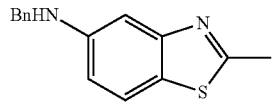 33% | $^1$H NMR (400 MHz, CDCl$_3$) δ 7.54 (d, J = 8.6 Hz, 1H), 7.43-7.38 (m, 2H), 7.38-7.31 (m, 2H), 7.30-7.26 (m, 1H), 7.16 (d, J = 2.4 Hz, 1H), 6.73 (dd, J = 8.6, 2.3 Hz, 1H), 2.77 (s, 3H); HRMS (ESI) calcd for C$_{15}$H$_{15}$N$_2$S (M + H)$^+$ 255.0956, found 255.0952. |

| Product and Yield | Characterization data of product |
| --- | --- |
| 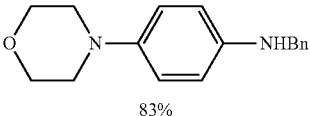 83% | ¹H NMR (400 MHz, CDCl₃) δ 7.40-7.31 (m, 4H), 7.30-7.26 (m, 1H), 6.84 (d, J = 8.8 Hz, 2H), 6.63 (d, J = 8.8 Hz, 2H), 4.30 (s, 2H), 3.88-3.83 (m, 4H), 3.06-2.98 (m, 4H); ¹³C NMR (126 MHz, CDCl₃) δ 143.71, 142.91, 139.78, 128.67, 127.63, 127.25, 118.47, 114.00, 67.20, 51.34, 49.10; HRMS (ESI) calcd for $C_{17}H_{21}N_2O$ (M + H)⁺ 269.1654, found 269.1650. |
| 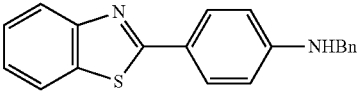 82% | ¹H NMR (400 MHz, CDCl₃) δ 7.98 (d, J = 8.0 Hz, 1H), 7.94-7.89 (m, 2H), 7.84 (d, J = 8.0 Hz, 1H), 7.46-7.41 (m, 1H), 7.40-7.35 (m, 4H), 7.34-7.28 (m, 2H), 6.73-6.66 (m, 2H), 4.45 (s, 1H), 4.42 (s, 2H); ¹³C NMR (125 MHz, CDCl₃) δ 168.77, 154.44, 150.52, 138.67, 134.68, 129.25, 128.90, 127.63, 127.56, 126.14, 124.44, 123.06, 122.50, 121.50, 112.71, 47.96; HRMS (ESI) calcd for $C_{20}H_{17}N_2S$ (M + H)⁺ 317.1112, found 317.1108. |

Example 7 Synthesis of Substituted Aromatic Amines (Different Arylchlorides and Different Amines)

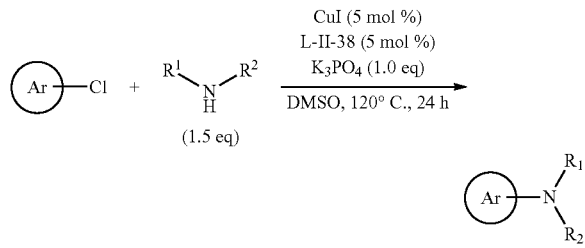

Copper iodide (0.05 mmol), ligand L-II-38 (0.05 mmol) and potassium phosphate (1.0 mmol) were added into a 10 mL of Schlenk tube. The tube was then evacuated and backfilled with argon (this sequence was repeated three times), and then aryl chloride (1.0 mmol), amine (1.5 mmol) and 1 mL of DMSO were added. The reaction mixture was stirred well at 120° C. for 24 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography to give the product substituted aromatic amines.

Different aryl chlorides and different amines were used in this example. The results are given in the following table.

| Product and Yield | Characterization data of product |
| --- | --- |
| 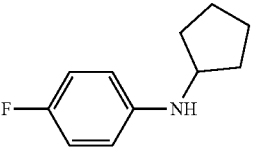 80% | ¹H NMR (400 MHz, CDCl₃) δ 6.92-6.83 (m, 2H), 6.56-6.50 (m, 2H), 3.73 (p, J = 6.1 Hz, 1H), 3.49 (s, 1H), 2.08-1.94 (m, 2H), 1.79-1.57 (m, 4H), 1.51-1.39 (m, 2H); ¹³C NMR (125 MHz, CDCl₃) δ 155.73 (d, J = 234.2 Hz), 144.55 (d, J = 1.8 Hz), 115.68 (d, J = 22.3 Hz), 114.08 (d, J = 7.2 Hz), 55.41, 33.67, 24.21 HRMS (ESI) calcd for $C_{11}H_{15}FN$ (M + H)⁺ 180.1189, found 180.1183 |
| 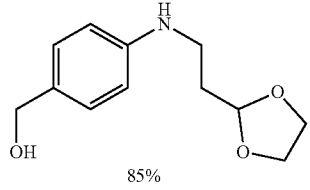 [SMILES: OCc1ccc(NCCC2OCCO2)cc1] 85% | ¹H NMR (400 MHz, CDCl₃) δ 7.16 (d, J = 8.5 Hz, 2H), 6.59 (d, J = 8.5 Hz, 2H), 4.97 (t, J = 4.5 Hz, 1H), 4.52 (s, 2H), 4.02-3.93 (m, 2H), 3.91-3.81 (m, 2H), 3.26 (t, J = 6.5 Hz, 2H), 2.00 (td, J = 6.5, 4.5 Hz, 2H); ¹³C NMR (125 MHz, CDCl₃) δ 148.17, 129.80, 128.90, 112.91, 103.76, 65.45, 65.02, 65.02, 39.36, 33.01; HRMS (ESI) calcd for $C_{12}H_{18}NO_3$ (M + H)⁺ 224.1287, found 224.1285. |
| 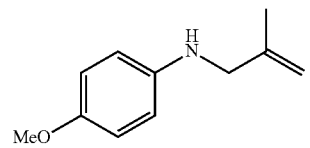 79% | ¹H NMR (400 MHz, CDCl₃) δ 6.82-6.74 (m, 2H), 6.62-6.55 (m, 2H), 4.97 (td, J = 1.7, 0.9 Hz, 1H), 4.89 (m, 1H), 3.75 (s, 3H), 3.65 (s, 2H), 1.79 (dd, J = 1.5, 0.9 Hz, 3H); ¹³C NMR (125 MHz, CDCl₃) δ 152.15, 143.25, 142.65, 114.97, 114.19, 110.97, 55.93, 51.00, 20.64; HRMS (ESI) calcd for $C_{11}H_{16}NO$ (M + H)⁺ 178.1232, found 178.1228. |
| 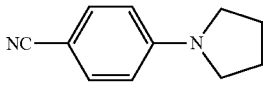 81% | ¹H NMR (400 MHz, CDCl₃) δ 7.44 (d, J = 8.9 Hz, 2H), 6.49 (d, J = 8.9 Hz, 2H), 3.36-3.27 (m, 4H), 2.10-1.97 (m, 4H); ¹³C NMR (125 MHz, CDCl₃) δ 150.14, 133.57, 121.13, 111.57, 96.70, 47.61, 25.54; HRMS (ESI) calcd for $C_{11}H_{13}N_2$ (M + H)⁺ 173.1079, found 173.1077. |

-continued

| Product and Yield | Characterization data of product |
|---|---|
| 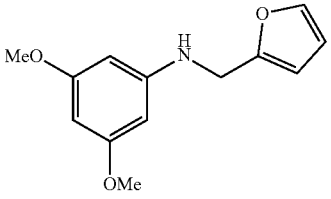 92% | $^1$H NMR (400 MHz, CDCl$_3$) δ 7.37 (dd, J = 1.9, 0.9 Hz, 1H), 6.32 (dd, J = 3.2, 1.9 Hz, 1H), 6.27-6.22 (m, 1H), 5.92 (t, J = 2.1 Hz, 1H), 5.87 (d, J = 2.1 Hz, 2H), 4.29 (s, 2H), 4.06 (s, 1H), 3.75 (s, 6H); $^{13}$C NMR (125 MHz, CDCl$_3$) δ 161.80, 152.66, 149.69, 142.05, 110.48, 107.17, 92.15, 90.45, 55.28, 41.53; HRMS (ESI) calcd for C$_{13}$H$_{16}$NO$_3$ (M + H)$^+$ 234.1130, found 234.1127. |
| 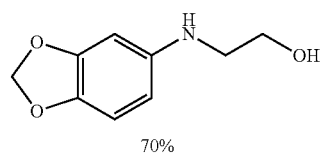 [SMILES: OCCNc1ccc2c(c1)OCO2] 70% | $^1$H NMR (400 MHz, CDCl$_3$) δ 6.66 (d, J = 8.3 Hz, 1H), 6.29 (d, J = 2.3 Hz, 1H), 6.10 (dd, J = 8.3, 2.3 Hz, 1H), 5.86 (s, 2H), 3.81 (t, J = 5.2 Hz, 2H), 3.23 (t, J = 5.2 Hz, 2H); $^{13}$C NMR (125 MHz, CDCl$_3$) δ 148.36, 143.79, 140.03, 108.60, 104.98, 100.63, 96.51, 61.25, 47.15; HRMS (ESI) calcd for C$_9$H$_{12}$NO$_3$ (M + H)$^+$ 182.0817, found 182.0814. |
| 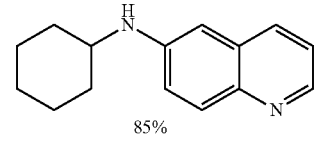 [SMILES: c1cnc2ccc(NC3CCCCC3)cc2c1] 85% | $^1$H NMR (400 MHz, CDCl$_3$) δ 8.58 (dd, J = 4.2, 1.7 Hz, 1H), 7.91-7.87 (m, 1H), 7.85 (d, J = 9.0 Hz, 1H), 7.23 (dd, J = 8.3, 4.2 Hz, 1H), 7.05 (dd, J = 9.0, 2.6 Hz, 1H), 6.68 (d, J = 2.6 Hz, 1H), 3.44-3.31 (m, 1H), 2.20-2.05 (m, 2H), 1.85-1.74 (m, 2H), 1.73-1.63 (m, 1H), 1.50-1.35 (m, 2H), 1.32-1.16 (m, 4H); $^{13}$C NMR (125 MHz, CDCl$_3$) δ 145.98, 145.36, 143.05, 133.74, 130.40, 130.37, 121.74, 121.44, 103.25, 51.86, 33.30, 26.03, 25.11; HRMS (ESI) calcd for C$_{15}$H$_{19}$N$_2$ (M + H)$^+$ 227.1548, found 227.1546. |
| 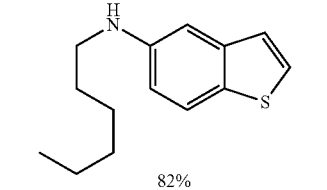 [SMILES: CCCCCCNc1ccc2sccc2c1] 82% | $^1$H NMR (400 MHz, CDCl$_3$) δ 7.62 (d, J = 8.6 Hz, 1H), 7.36 (d, J = 5.4 Hz, 1H), 7.17 (dd, J = 5.4, 0.8 Hz, 1H), 6.98 (d, J = 2.3 Hz, 1H), 6.73 (dd, J = 8.7, 2.3 Hz, 1H), 3.63 (s, 1H), 3.16 (t, J = 7.1 Hz, 2H), 1.72-1.61 (m, 2H), 1.49-1.39 (m, 2H), 1.38-1.30 (m, 4H), 0.97-0.86 (m, 3H); $^{13}$C NMR (125 MHz, CDCl$_3$) δ 146.18, 141.18, 129.25, 126.88, 123.47, 122.89, 114.15, 104.93, 44.72, 31.82, 29.64, 27.06, 22.79, 14.20; HRMS (ESI) calcd for C$_{14}$H$_{20}$NS (M + H)$^+$ 234.1316, found 234.1315. |

Example 8 Synthesis of (4-aminophenyl)methanol

Chlorobenzyl alcohol (0.5 mmol), ammonia source (0.75 mmol), copper salt catalyst (0.05 mmol), ligand (0.05 mmol) and base (0.5 mmol) were added into a 10 mL of Schlenk tube. The tube was then evacuated and backfilled with argon (this sequence was repeated three times), and then 0.5 mL of solvent was added. The reaction mixture was stirred well at 110° C. for 12 hours. After cooling, the mixture was filtered through silica gel and celite. The filtrate was concentrated and purified by column chromatography to give the product (4-aminophenyl) methanol (light yellow solid).

$^1$H NMR (400 MHz, CDCl$_3$) δ 7.11 (d, J=8.3 Hz, 2H), 6.62 (d, J=8.3 Hz, 2H), 4.49 (s, 2H), 3.22 (br s, 2H); $^{13}$C NMR (100 MHz, CDCl$_3$) δ 145.9, 131.0, 128.7, 115.1, 65.1; LC-MS (ESI, m/z): 124.1 (M+H)$^+$.

In this example, different ammonia sources, copper salt catalysts, ligands, bases and solvents were used. The results are given in the following table.

| No. | ammonia source | copper salt | ligand | base | solvent | Yield/% |
|---|---|---|---|---|---|---|
| 1 | NH$_3$•H$_2$O | CuI | L-II-4 | K$_3$PO$_4$ | DMSO | 33 |
| 2 | NH$_3$•H$_2$O | CuI | L-II-37 | K$_3$PO$_4$ | DMSO | 62 |
| 3 | NH$_3$•H$_2$O | CuI | L-II-41 | K$_3$PO$_4$ | DMSO | 31 |
| 4 | NH$_3$•H$_2$O | CuI | L-II-2 | K$_3$PO$_4$ | DMSO | 25 |
| 5 | NH$_3$•H$_2$O | CuI | L-II-42 | K$_3$PO$_4$ | DMSO | 30 |
| 6 | NH$_3$•H$_2$O | CuI | L-II-8 | K$_3$PO$_4$ | DMSO | <10 |
| 7 | NH$_3$•H$_2$O | CuI | L-II-38 | K$_3$PO$_4$ | DMSO | 90 |
| 8 | NH$_3$•H$_2$O | CuI | L-II-31 | K$_3$PO$_4$ | DMSO | 68 |
| 9 | NH$_3$•H$_2$O | CuI | L-II-34 | K$_3$PO$_4$ | DMSO | 82 |
| 10 | NH$_3$•H$_2$O | CuI | L-II-27 | K$_3$PO$_4$ | DMSO | 14 |
| 11 | NH$_3$•H$_2$O | CuI | L-II-29 | K$_3$PO$_4$ | DMSO | 42 |
| 12 | NH$_3$•H$_2$O | CuI | L-II-30 | K$_3$PO$_4$ | DMSO | 78 |
| 13 | NH$_3$•H$_2$O | CuI | L-II-28 | K$_3$PO$_4$ | DMSO | 23 |
| 14 | NH$_3$•H$_2$O | CuI | L-II-36 | K$_3$PO$_4$ | DMSO | 49 |
| 15 | NH$_4$Cl + KOH | CuI | L-II-1 | K$_3$PO$_4$ | DMSO | 32 |
| 16 | NH$_4$Cl + KOH | CuI | L-II-3 | K$_3$PO$_4$ | DMSO | 44 |
| 17 | NH$_4$Cl + KOH | CuI | L-II-4 | K$_3$PO$_4$ | DMSO | 63 |
| 18 | NH$_4$Cl + KOH | CuI | L-II-5 | K$_3$PO$_4$ | DMSO | 40 |
| 19 | NH$_4$Cl + KOH | CuI | L-II-6 | K$_3$PO$_4$ | DMSO | 35 |
| 20 | NH$_4$Cl + KOH | CuI | L-II-7 | K$_3$PO$_4$ | DMSO | 33 |
| 21 | NH$_4$Cl + KOH | CuI | L-II-9 | K$_3$PO$_4$ | DMSO | 33 |
| 22 | NH$_3$•H$_2$O | CuI | L-II-34 | K$_3$PO$_4$ | DMF | 56 |
| 23 | NH$_3$•H$_2$O | CuI | L-II-34 | K$_3$PO$_4$ | DMA | 58 |
| 24 | NH$_3$•H$_2$O | CuI | L-II-34 | K$_3$PO$_4$ | NMP | 42 |
| 25 | NH$_3$•H$_2$O | CuI | L-II-34 | K$_3$PO$_4$ | MeCN | 16 |
| 26 | NH$_3$•H$_2$O | CuI | L-II-34 | K$_3$PO$_4$ | 1,4-dioxane | <10 |
| 27 | NH$_3$•H$_2$O | CuI | L-II-34 | K$_3$PO$_4$ | THF | <10 |

-continued

| No. | ammonia source | copper salt | ligand | base | solvent | Yield/% |
|---|---|---|---|---|---|---|
| 28 | NH₄Cl + KOH | CuI | L-II-34 | K₃PO₄ | DMSO | 67 |
| 29 | (NH₄)₂CO₃ + KOH | CuI | L-II-34 | K₃PO₄ | DMSO | 39 |
| 30 | (NH₄)₂SO₄ + KOH | CuI | L-II-34 | K₃PO₄ | DMSO | 59 |
| 31 | (NH₄)₂HPO₄ + KOH | CuI | L-II-34 | K₃PO₄ | DMSO | 70 |
| 32 | NH₃ (gas, 5 atm) | CuI | L-II-34 | K₃PO₄ | DMSO | 77 |
| 33 | NaN₃ | CuI | L-II-38 | K₃PO₄ | DMSO | 43 |
| 34 | NH₃·H₂O | CuI | L-II-34 | K₂CO₃ | DMSO | 51 |
| 35 | NH₃·H₂O | CuI | L-II-34 | Na₂CO₃ | DMSO | 17 |
| 36 | NH₃·H₂O | CuI | L-II-34 | Cs₂CO₃ | DMSO | 90 |
| 37 | NH₃·H₂O | CuBr | L-II-34 | K₃PO₄ | DMSO | 71 |
| 38 | NH₃·H₂O | CuCl | L-II-34 | K₃PO₄ | DMSO | 73 |
| 39 | NH₃·H₂O | Cu₂O | L-II-34 | K₃PO₄ | DMSO | 51 |
| 40 | NH₃·H₂O | Cu(OAc)₂ | L-II-34 | K₃PO₄ | DMSO | 43 |
| 41 | NH₃·H₂O | CuTc | L-II-34 | K₃PO₄ | DMSO | 24 |
| 42[a] | NH₃·H₂O | CuI | L-II-38 | K₃PO₄ | DMSO | 68 |
| 43[a] | NH₃·H₂O | CuI | L-II-64 | K₃PO₄ | DMSO | 69 |
| 44[a] | NH₃·H₂O | CuI | L-II-58 | K₃PO₄ | DMSO | 44 |
| 45[a] | NH₃·H₂O | CuI | L-II-37 | K₃PO₄ | DMSO | 77 |
| 46[a] | NH₃·H₂O | CuI | L-II-71 | K₃PO₄ | DMSO | 87 |
| 47[a] | NH₃·H₂O | CuI | L-II-73 | K₃PO₄ | DMSO | 84 |

[a] 2.0 eq ammonium hydroxide (1.0 mmol) was used as ammonia source, and the reaction temperature was 105° C.

Example 9 Synthesis of Aromatic Amines

Copper iodide (0.05 mmol), ligand L-II-71 (0.05 or 0.1 mmol), potassium phosphate (1.1 mmol) were added into a 10 mL of Schlenk tube. The tube was then evacuated and backfilled with argon (this sequence was repeated three times), and then aryl chloride (1.0 mmol), 1 mL of DMSO and ammonium hydroxide (2.0 mmol) were added. The reaction mixture was well stirred at 110° C. or 120° C. for 24 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography to give the product aromatic amines.

Figure 4:
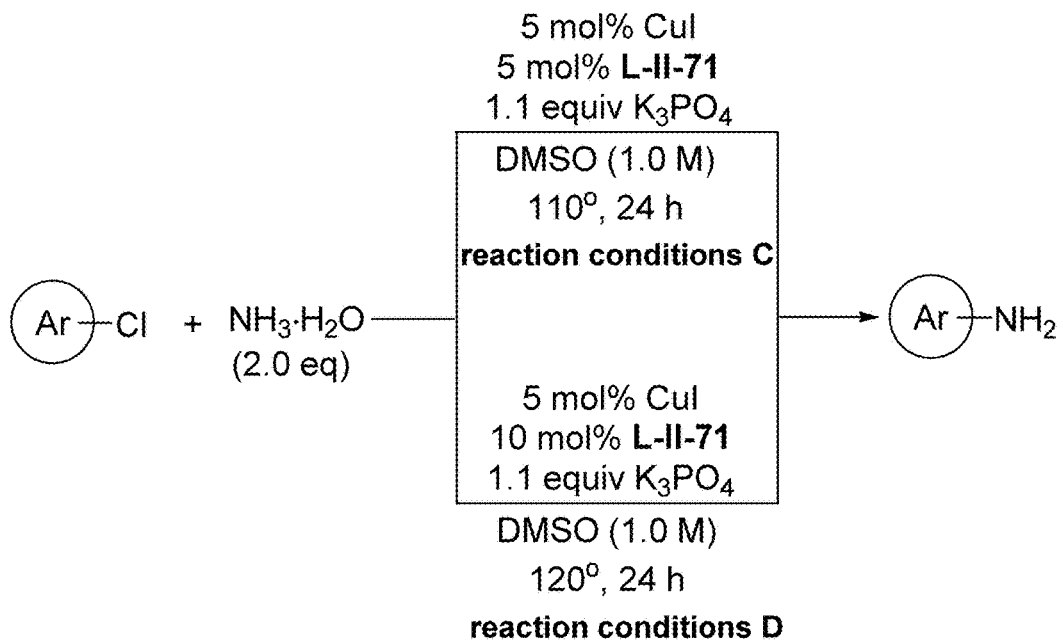

In this example, different aryl chlorides were used, and the reaction conditions were C and D. Condition C were for the more reactive aryl chlorides and condition D were for the relatively less reactive aryl chlorides. The results are shown in the table below. A schematic of this reaction of the synthesis of aromatic amines using copper iodide, potassium phosphate, aryl chloride, and ammonium hydroxide is shown in FIG. 4.

| Product, Reaction Conditions and Yield | Characterization data of product |
|---|---|
| 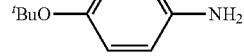<br>reaction condition C, 73% | ¹H NMR (400 MHz, CDCl₃) δ 6.84-6.75 (m, 2H), 6.63-6.55 (m, 2H), 3.51 (s, 2H), 1.28 (s, 9H); ¹³C NMR (100 MHz, CDCl₃) δ 147.05, 142.38, 125.34, 115.39, 77.71, 28.68.; LC-MS (ESI, m/z): 166.2 (M + H)⁺. |
| 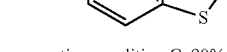<br>reaction condition C, 90% | ¹H NMR (400 MHz, CDCl₃) δ 7.50 (dd, J = 8.5, 0.6 Hz, 1H), 6.92 (t, J = 1.3 Hz, 1H), 6.89 (dd, J = 2.3, 0.6 Hz, 1H), 6.69 (dd, J = 8.5, 2.3 Hz, 1H), 3.60 (br, 1H), 2.26 (d, J = 1.3 Hz, 3H).; ¹³C NMR (100 MHz, CDCl₃) δ 143.35, 140.78, 131.17, 130.53, 123.10, 122.19, 114.54, 106.62, 13.80; HRMS (ESI) calcd. for C₉H₁₀NS (M + H)⁺: 164.0528. Found: 164.0532. |
| 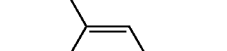<br>reaction condition D, 88% | ¹H NMR (400 MHz, CDCl₃) δ 5.93 (t, J = 2.1 Hz, 1H), 5.87 (d, J = 2.1 Hz, 2H), 3.74 (s, 6H); ¹³C NMR (100 MHz, CDCl₃) δ 161.59, 148.53, 93.63, 90.77, 55.02; LC-MS (ESI, m/z): 154.1 (M + H)⁺. |
| 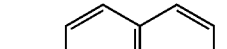<br>reaction condition C, 98% | ¹H NMR (400 MHz, CDCl₃) δ 7.87 (d, J = 8.3 Hz, 1H), 7.56 (d, J = 8.6 Hz, 1H), 7.15 (d, J = 2.3 Hz, 1H), 7.02 (d, J = 8.2 Hz, 1H), 6.91 (dd, J = 8.6, 2.3 Hz, 1H), 4.04 (br s, 2H), 2.67 (s, 3H); ¹³C NMR (100 MHz, CDCl₃) δ 158.95, 149.34, 148.01, 135.91, 128.53, 120.22, 118.34, 117.62, 108.34, 25.04; HRMS (ESI) calcd. for C₁₀H₁₁N₂ (M + H)⁺: 159.0917, Found: 159.0919. |
| 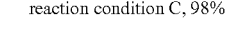<br>reaction condition D, 78% | ¹H NMR (500 MHz, CDCl₃) δ 7.95 (d, J = 8.4 Hz, 1H), 7.29-7.21 (m, 2H), 7.11 (dd, J = 8.1, 1.3 Hz, 1H), 6.90 (dd, J = 7.5, 1.2 Hz, 1H), 4.95 (s, 2H), 2.71 (s, 3H); ¹³C NMR (100 MHz, CDCl₃) δ 156.10, 143.44, 137.85, 136.04, 126.89, 126.31, 122.11, 115.84, 110.10, 25.22; LC-MS (ESI, m/z): 159.1 (M + H)⁺. |

| Product, Reaction Conditions and Yield | Characterization data of product |
|---|---|
| 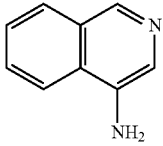<br>reaction condition D, 80% | $^1$H NMR (500 MHz, CDCl$_3$) δ 8.74 (s, 1H), 8.03 (s, 1H), 7.95-7.87 (m, 1H), 7.84-7.75 (m, 1H), 7.71-7.62 (m, 1H), 7.62-7.53 (m, 1H), 4.11 (s, 2H); $^{13}$C NMR (100 MHz, CDCl$_3$) δ 142.97, 137.12, 128.96, 128.63, 127.99, 127.73, 127.03, 126.05, 120.12; LC-MS (ESI, m/z): 145.1 (M + H)$^+$. |
| 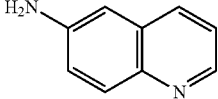<br>reaction condition C, 96% | $^1$H NMR (400 MHz, CDCl$_3$) δ 8.65 (dd, J = 4.2, 1.6 Hz, 1H), 7.94-7.86 (m, 2H), 7.27 (dd, J = 8.2, 4.3 Hz, 1H), 7.16 (dd, J = 8.9, 2.6 Hz, 1H), 6.90 (d, J = 2.7 Hz, 1H), 3.96 (s, 2H).; $^{13}$C NMR (100 MHz, CDCl$_3$) δ 146.50, 144.85, 143.14, 133.75, 130.19, 129.74, 121.60, 121.29, 107.20; LC-MS (ESI, m/z): 145.1 (M + H)$^+$. |
| 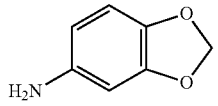<br>reaction condition C, 74% | $^1$H NMR (400 MHz, CDCl$_3$) δ 6.62 (d, J = 8.1 Hz, 1H), 6.29 (d, J = 2.3 Hz, 1H), 6.13 (dd, J = 8.1, 2.3 Hz, 1H), 5.86 (s, 2H), 3.45 (s, 2H); $^{13}$C NMR (100 MHz, CDCl$_3$) δ 148.18, 141.46, 140.30, 108.58, 106.89, 100.65, 98.08; LC-MS (ESI, m/z): 138.1 (M + H)$^+$. |
| 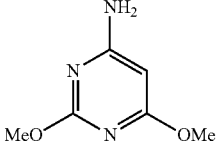<br>reaction condition D, 69% | $^1$H NMR (400 MHz, CDCl$_3$) δ 5.45 (s, 1H), 4.68 (br s, 2H), 3.90 (s, 3H), 3.89 (s, 3H); $^{13}$C NMR (125 MHz, CDCl$_3$) δ 171.94, 165.80, 165.18, 80.40, 54.08, 53.40; LC-MS (ESI, m/z): 156.1 (M + H)$^+$. |
| 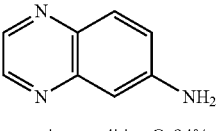<br>reaction condition C, 94% | $^1$H NMR (500 MHz, CDCl$_3$) δ 8.66 (d, J = 2.0 Hz, 1H), 8.55 (d, J = 1.9 Hz, 1H), 7.88 (d, J = 8.9 Hz, 1H), 7.19 (dd, J = 9.0, 2.6 Hz, 1H), 7.14 (d, J = 2.5 Hz, 1H), 4.23 (s, 2H); $^{13}$C NMR (100 MHz, CDCl$_3$) δ 148.27, 145.09, 144.97, 141.02, 138.09, 130.47, 122.23, 107.93; LC-MS (ESI, m/z): 146.1 (M + H)$^+$. |
| 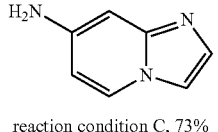<br>reaction condition C, 73% | $^1$H NMR (500 MHz, d6-DMSO) δ 8.17-8.10 (m, 1H), 7.50 (br s, 1H), 7.19 (d, J = 1.4 Hz, 1H), 6.42-6.36 (m, 2H), 5.65 (br s, 2H); $^{13}$C NMR (125 MHz, d6-DMSO) δ 147.05, 146.47, 131.18, 126.71, 110.36, 106.49, 92.25; LC-MS (ESI, m/z): 134.1 (M + H)$^+$. |
| 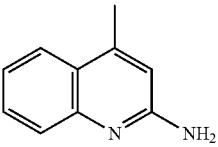<br>reaction condition C, 87% | $^1$H NMR (400 MHz, CDCl$_3$) δ 7.79 (dd, J = 8.3, 1.4 Hz, 1H), 7.67 (dd, J = 8.3, 1.2 Hz, 1H), 7.56 (d, J = 1.5 Hz, 0H), 7.35-7.23 (m, 1H), 6.59 (s, 1H), 4.94 (br s, 2H), 2.58 (d, J = 1.0 Hz, 3H); $^{13}$C NMR (125 MHz, CDCl$_3$) δ 155.88, 148.30, 142.39, 130.38, 123.91, 123.22, 122.70, 122.58, 112.40, 18.80; LC-MS (ESI, m/z): 159.1 (M + H)$^+$. |
| 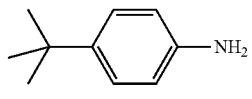<br>reaction condition C, 80% | $^1$H NMR (400 MHz, CDCl$_3$) δ 7.16 (d, J = 8.0 Hz, 2 H), 6.60 (d, J = 8.0 Hz, 2 H), 3.49 (br s, 2 H), 1.27 (s, 9 H); $^{13}$C NMR (100 MHz, CDCl$_3$) δ 143.9, 141.3, 126.1, 115.0, 33.9, 31.6; LC-MS (ESI, m/z): 150.2 (M + H)$^+$. |

| Product, Reaction Conditions and Yield | Characterization data of product |
|---|---|
| 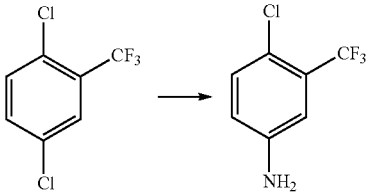<br>reaction condition C, 84% | $^1$H NMR (400 MHz, CDCl$_3$) δ 7.25 (d, J = 7.1 Hz, 1H), 6.96 (d, J = 2.8 Hz, 1H), 6.73 (dd, J = 8.6, 2.7 Hz, 1H), 3.84 (br s, 2H); $^{13}$C NMR (125 MHz, CDCl$_3$) δ 145.26, 132.18, 128.81 (q, J = 31.0 Hz), 122.98 (q, J = 273.1 Hz), 120.34 (q, J = 1.9 Hz), 118.80, 113.76 (q, J = 5.6 Hz); LC-MS (ESI, m/z): 195.9 (M + H)$^+$. |
| 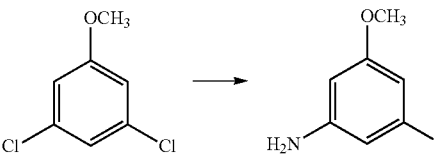<br>reaction condition C, 76% | $^1$H NMR (500 MHz, CDCl$_3$) δ 6.32 (t, J = 2.0 Hz, 1H), 6.28 (t, J = 1.9 Hz, 1H), 6.09 (t, J = 2.1 Hz, 1H), 3.73 (s, 3H), 3.63 (s, 2H); $^{13}$C NMR (125 MHz, CDCl$_3$) δ 161.28, 148.47, 135.41, 108.05, 104.53, 99.41, 55.39; LC-MS (ESI, m/z): 158.1 (M + H)$^+$. |
| 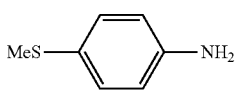<br>reaction condition C, 85% | $^1$H NMR (400 MHz, CDCl$_3$) δ 7.18 (d, J = 8.5 Hz, 2H), 6.63 (d, J = 8.5 Hz, 2H), 3.53 (s, 2H), 2.41 (s, 3H); $^{13}$C NMR (125 MHz, CDCl$_3$) δ 145.17, 131.02, 125.65, 115.74, 18.77; LC-MS (ESI, m/z): 140.1 (M + H)$^+$. |
| 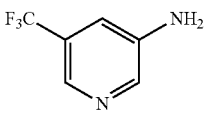<br>reaction condition C, 74% | $^1$H NMR (500 MHz, CDCl$_3$) δ 8.35-8.14 (m, 2H), 7.14 (t, J = 2.4 Hz, 1H), 3.91 (br s, 2H); $^{13}$C NMR (125 MHz, CDCl$_3$) δ 143.06, 139.95, 135.29 (q, J = 4.4 Hz), 127.62, 127.03 (q, J = 32.6 Hz), 124.91, 122.20, 119.49, 117.48 (g, J = 3.7 Hz); LC-MS (ESI, m/z): 163.0 (M + H)$^+$. |
| 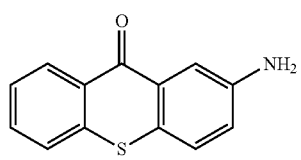<br>reaction condition C, 70% | $^1$H NMR (400 MHz, DMSO-d6-d6-d$_6$) δ 8.44 (dd, J = 8.2, 1.1 Hz, 1H), 7.80-7.74 (m, 1H), 7.74-7.67 (m, 1H), 7.66 (d, J = 2.6 Hz, 1H), 7.55-7.46 (m, 2H), 7.09 (dd, J = 8.6, 2.6 Hz, 1H), 5.67 (s, 2H); $^{13}$C NMR (126 MHz, DMSO-d$_6$) δ 178.69, 148.06, 137.17, 132.11, 129.38, 129.02, 127.92, 127.05, 126.33, 125.87, 122.07, 121.20, 110.90; LC-MS (ESI, m/z): 228.1 (M + H)$^+$. |
| 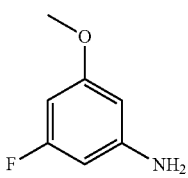<br>reaction condition C, 79% | $^1$H NMR (400 MHz, CDCl$_3$) δ 6.07-5.98 (m, 3H), 3.75 (s, 2H), 3.74 (s, 3H); $^{13}$C NMR (125 MHz, CDCl$_3$) δ 164.69 (d, J = 241.8 Hz), 161.83 (d, J = 13.5 Hz), 148.70 (d, J = 13.4 Hz), 96.68 (d, J = 2.4 Hz), 95.05 (d, J = 25.2 Hz), 91.96 (d, J = 25.7 Hz), 55.46; LC-MS (ESI, m/z): 141.1 (M + H)$^+$. |
| 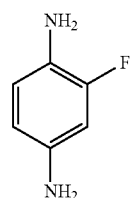<br>reaction condition C, 75% | $^1$H NMR (400 MHz, CDCl$_3$) δ 6.63 (dd, J = 9.8, 8.3 Hz, 1H), 6.42 (dd, J = 12.3, 2.5 Hz, 1H), 6.33 (ddd, J = 8.3, 2.5, 1.0 Hz, 1H), 3.35 (s, 4H); $^{13}$C NMR (125 MHz, CDCl$_3$) δ 152.59 (d, J = 238.0 Hz), 139.39 (d, J = 9.4 Hz), 126.04 (d, J = 13.5 Hz), 118.56 (d, J = 4.8 Hz), 111.56 (d, J = 3.2 Hz), 103.63 (d, J = 22.3 Hz); LC-MS (ESI, m/z): 127.1 (M + H)$^+$. |
| 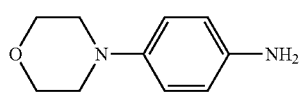<br>reaction condition D, 83% | $^1$H NMR (400 MHz, CDCl$_3$) δ 6.83-6.76 (m, 2H), 6.70-6.63 (m, 2H), 3.89-3.81 (m, 4H), 3.43 (s, 2H), 3.08-2.95 (m, 4H); $^{13}$C NMR (125 MHz, CDCl$_3$) δ 144.57, 140.44, 118.33, 116.36, 67.22, 51.25; LC-MS (ESI, m/z): 179.3 (M + H)$^+$. |

| Product, Reaction Conditions and Yield | Characterization data of product |
|---|---|
| 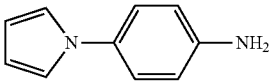<br>reaction condition C, 57% | $^1$H NMR (400 MHz, CDCl$_3$) δ 7.15-7.06 (m, 2H), 6.94-6.86 (m, 2H), 6.69-6.60 (m, 2H), 6.27-6.18 (m, 2H), 3.60 (s, 2H); $^{13}$C NMR (125 MHz, CDCl$_3$) δ 144.65, 133.04, 122.49, 119.81, 115.78, 109.56; LC-MS (ESI, m/z): 159.1 (M + H)$^+$. |
| 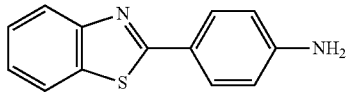<br>reaction condition C, 95% | $^1$H NMR (400 MHz, CDCl$_3$) δ 7.99 (d, J = 8.1 Hz, 1H), 7.93-7.87 (m, 2H), 7.85 (d, J = 7.9 Hz, 1H), 7.48-7.41 (m, 1H), 7.36-7.29 (m, 1H), 6.77-6.71 (m, 2H), 4.00 (s, 2H); $^{13}$C NMR (125 MHz, CDCl$_3$) δ 168.65, 154.39, 149.36, 134.73, 129.29, 126.20, 124.59, 124.11, 122.63, 121.55, 114.92; LC-MS (ESI, m/z): 227.2 (M + H)$^+$. |
| 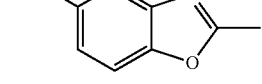<br>reaction condition C, 69% | $^1$H NMR (400 MHz, CDCl$_3$) δ 7.21 (d, J = 8.8 Hz, 1 H), 6.92 (d, J = 2.0 Hz, 1 H), 6.61 (dd, J = 8.4 Hz, J = 2.0 Hz, 1 H), 3.77 (s, 2 H), 2.55 (s, 3 H); $^{13}$C NMR (125 MHz, CDCl$_3$) δ 164.3, 144.8, 143.6, 142.4, 112.8, 110.2, 104.7, 14.5; LC-MS (ESI, m/z): 149.1 (M + H)$^+$. |
| 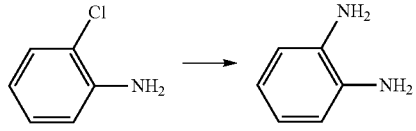<br>reaction condition D, 49% | $^1$H NMR (400 MHz, CDCl$_3$) δ 6.76-6.68 (m, 4H), 3.33 (br s, 4H); $^{13}$C NMR (100 MHz, CDCl$_3$) δ 134.8, 120.3, 116.7; LC-MS (ESI, m/z): 109.2 (M + H)$^+$. |
| 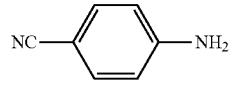<br>88%, (NH$_4$)$_2$HPO$_4$(0.75 eq) used as ammonia source, K$_3$PO$_4$(2.5 eq) used as base, DMF used as solvent, reaction for 14 hours | $^1$H NMR (400 MHz, CDCl$_3$) δ 4.40 (br s, 2H), 6.60 (d, J = 8.8 Hz, 2H), 7.33 (d, J = 8.8 Hz, 2H); $^{13}$C NMR (100 MHz, CDCl$_3$) δ 99.7, 114.3, 120.2, 133.6, 150.5; LC-MS (ESI, m/z): 119.1 (M + H)$^+$. |

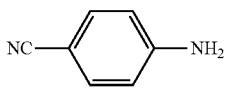

86%, 20 mmol scale, CuI (2.5 mol %) and L-II-38 (5 mol %) were used, NH$_3$ (gas, 5 atm) was used as ammonia source, K$_3$PO$_4$ (1.1 eq) was used as base, DMSO (8 mL) was used as solvent, the reaction was carried out in an autoclave at 120° C. for 25 hours.

Example 10 Synthesis of 1-methyl-4-phenoxybenzene

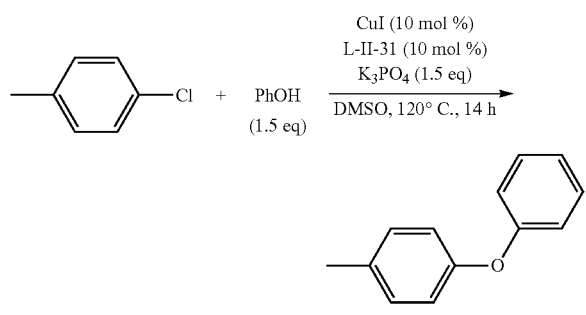

Phenol (1.5 mmol), copper iodide (0.1 mmol), ligand L-II-31 (0.1 mmol) and potassium phosphate (1.5 mmol) were added into a 10 mL of Schlenk tube. The tube was then evacuated and backfilled with argon (this sequence was repeated three times), and then 1-chloro-4-methylbenzene (1.0 mmol) and 1 mL of DMSO were added. The reaction mixture was well stirred at 120° C. for 14 hours. After cooling, the contents of the of Schlenk tube were washed with ethyl acetate, and filtrated through silica gel and kieselguhr. The filtrate was concentrated and purified by column chromatography to give the product 1-methyl-4-phenoxybenzene (0.1105 g, yield 60%).

$^1$H NMR (400 MHz, CDCl$_3$) δ 7.40-7.31 (m, 2H), 7.21-7.15 (m, 2H), 7.14-7.08 (m, 1H), 7.06-7.01 (m, 2H), 7.00-6.93 (m, 2H), 2.38 (s, 3H); $^{13}$C NMR (100 MHz, CDCl$_3$) δ 158.02, 154.91, 133.06, 130.45, 129.83, 122.98, 119.32, 118.53, 20.89

Example 11 Synthesis of 1-methyl-4-phenoxybenzene

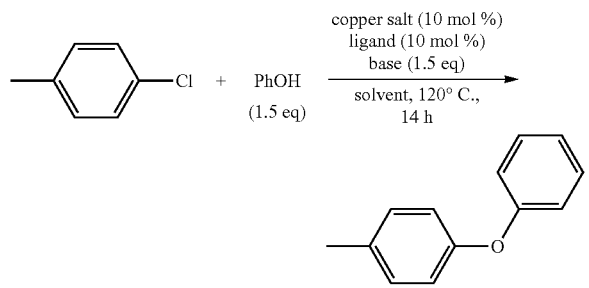

The operation of this example was the same as that of Example 10 except that different ligands, copper salt catalysts, bases, solvents and temperature were used. The results are shown in the following table.

| Ligand | Copper salt | Base | Solvent | Temperature/°C. | Yield/% |
|---|---|---|---|---|---|
| L-II-31 | CuI | $K_3PO_4$ | DMSO | 120 | 60 |
| L-II-31 | CuBr | $K_3PO_4$ | DMSO | 120 | 57 |
| L-II-31 | CuCl | $K_3PO_4$ | DMSO | 120 | 55 |
| L-II-31 | CuTc | $K_3PO_4$ | DMSO | 120 | 50 |
| L-II-31 | Cu(OAc)$_2$ | $K_3PO_4$ | DMSO | 120 | 43 |
| L-II-31 | CuSO4 | $K_3PO_4$ | DMSO | 120 | 49 |
| L-II-31 | CuBr$_2$ | $K_3PO_4$ | DMSO | 120 | 52 |
| L-II-31 | CuCl$_2$ | $K_3PO_4$ | DMSO | 120 | 56 |
| L-II-31 | Cu$_2$O | $K_3PO_4$ | DMSO | 120 | 53 |
| L-II-31 | CuI | $K_2CO_3$ | DMSO | 120 | 15 |
| L-II-31 | CuI | $Cs_2CO_3$ | DMSO | 120 | 49 |
| L-II-31 | CuI | $K_3PO_4$ | NMP | 120 | 44 |
| L-II-31 | CuI | $K_3PO_4$ | DMF | 120 | 33 |
| L-II-31 | CuI | $K_3PO_4$ | MeCN | 120 | 41 |
| L-II-31 | CuI | $K_3PO_4$ | 1,4-dioxane | 120 | 37 |
| L-II-31 | CuI | $K_3PO_4$ | $^t$BuOH | 120 | 18 |
| L-II-38 | CuI | $K_3PO_4$ | DMSO | 120 | 20 |
| L-II-33 | CuI | $K_3PO_4$ | DMSO | 120 | 20 |
| L-II-36 | CuI | $K_3PO_4$ | DMSO | 120 | 45 |
| L-II-29 | CuI | $K_3PO_4$ | DMSO | 120 | 44 |
| L-II-32 | CuI | $K_3PO_4$ | DMSO | 120 | 57 |
| L-II-35 | CuI | $K_3PO_4$ | DMSO | 120 | 46 |
| L-II-26 | CuI | $K_3PO_4$ | DMSO | 120 | 30 |
| L-II-40 | CuI | $K_3PO_4$ | DMSO | 120 | 54 |
| L-II-27 | CuI | $K_3PO_4$ | DMSO | 120 | 58 |
| L-II-37 | CuI | $K_3PO_4$ | DMSO | 120 | 66 |
| L-II-5 | CuI | $K_3PO_4$ | DMSO | 120 | 50 |
| L-II-7 | CuI | $K_3PO_4$ | DMSO | 120 | 51 |
| L-II-43 | CuI | $K_3PO_4$ | DMSO | 120 | 39 |
| L-II-9 | CuI | $K_3PO_4$ | DMSO | 120 | 41 |
| L-II-18 | CuI | $K_3PO_4$ | DMSO | 120 | 23 |
| L-II-20 | CuI | $K_3PO_4$ | DMSO | 120 | 26 |
| L-II-21 | CuI | $K_3PO_4$ | DMSO | 120 | 43 |
| L-II-30 | CuI | $K_3PO_4$ | DMSO | 120 | 74 |
| L-II-34 | CuI | $K_3PO_4$ | DMSO | 120 | 73 |
| L-II-4 | CuI | $K_3PO_4$ | DMSO | 120 | 70 |
| L-II-34 | CuI | $K_3PO_4$ | DMSO | 110 | 57 |
| L-II-34 | CuI | $K_3PO_4$ | DMSO | 110 | 40 |
| L-II-47 | CuI | $K_3PO_4$ | DMSO | 120 | 90 |

Example 12 Synthesize of Diaryl Ether Via Reaction of 1-chloro-4-methylbenzene with Phenol Phenol (1.2 mmol), copper iodide (0.05 mmol), ligand L-II-34 (0.1 mmol) and potassium phosphate (2.0 mmol) were added into a 10 mL of Schlenk tube. The tube was then evacuated and backfilled with argon (this sequence was repeated three times), and then 1-chloro-4-methylbenzene (1.0 mmol) and 1 mL of DMSO were added. The reaction mixture was stirred well at 120° C. for 24 hours. After cooling, the contents of the of Schlenk tube were washed with ethyl acetate, and filtrated through silica gel and kieselguhr. The filtrate was concentrated and purified by column chromatography to give the product diaryl ether. The results obtained are shown in the following table.

| Phenol | product and yield | Characterization data of product |
|---|---|---|
| Ph-OH | (85%) | $^1$H NMR (400 MHz, CDCl$_3$) δ 7.40-7.31 (m, 2H), 7.21-7.15 (m, 2H), 7.14-7.08 (m, 1H), 7.06-7.01 (m, 2H), 7.00-6.93 (m, 2H), 2.38 (s, 3H); $^{13}$C NMR (100 MHz, CDCl$_3$) δ 158.02, 154.91, 133.06, 130.45, 129.83, 122.98, 119.32, 118.53, 20.89; GC-MS (EI, m/z): 184.1 (M$^+$). |
| MeS-C$_6$H$_4$-OH | (97%) | $^1$H NMR (400 MHz, CDCl$_3$) δ 7.28-7.24 (m, 2H), 7.14 (d, J = 8.8 Hz, 2H), 6.96-6.88 (m, 4H), 2.47 (s, 3H), 2.34 (s, 3H); $^{13}$C NMR (100 MHz, CDCl$_3$) δ 154.0, 153.4, 132.5, 131.5, 129.3, 128.5, 117.7, 116.9, 21.5, 15.3; GC-MS (EI, m/z): 230.3 (M$^+$). |
| 2-naphthol | (80%) | $^1$H NMR (400 MHz, CDCl$_3$) δ 7.81-7.84 (2H, m), 7.68 (1H, d, J = 8.0 Hz, 7.38-7.47 (2H, m), 7.26 (2H, t, J = 3.6 Hz), 7.18 (2H, d, J = 8.0 Hz), 6.99 (2H, d, J = 8.4 Hz), 2.38 (3H, s); $^{13}$C NMR (100 MHz, CDCl$_3$) δ 155.7, 154.7, 134.4, 133.1, 130.3, 130.0, 129.8, 127.7, 127.1, 126.5, 124.5, 119.8, 119.3, 113.3, 20.8; GC-MS (EI, m/z): 234.2 (M$^+$). |

-continued

| Phenol | product and yield | Characterization data of product |
|---|---|---|
| 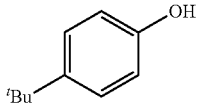 | 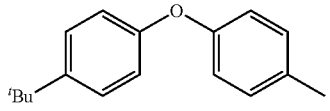<br>70% | $^{1}$H NMR (400 MHz, CDCl$_{3}$) δ 7.28-7.35 (m, 2H), 7.08-7.14 (m, 2H), 6.88-6.93 (m, 4H), 2.31 (s, 3H), 1.32 (s, 9H); $^{13}$C NMR (100 MHz, CDCl$_{3}$) δ 155.35, 155.08, 145.69, 132.62, 130.22, 126.51, 118.95, 118.65, 117.95, 115.96, 34.32, 31.58, 20.77; GC-MS (EI, m/z): 234.2 (M$^{+}$). |
| 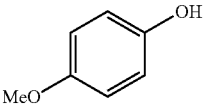 | 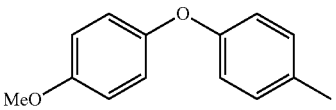<br>85% | $^{1}$H NMR (400 MHz, CDCl$_{3}$) δ 7.14 (2H, d, J = 8.3 Hz), 7.00 (2H, d, J = 9.1 Hz), 6.91 (4H, m), 3.83 (3H, s), 2.36 (3H, s); $^{13}$C NMR (100 MHz, CDCl$_{3}$) δ 156.0, 155.6, 150.7, 132.0, 130.0, 120.2, 117.7, 114.7, 55.6, 20.5; GC-MS (EI, m/z): 214.2 (M$^{+}$). |
| 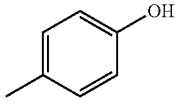 | 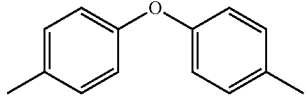<br>83% | $^{1}$H NMR (400 MHz, CDCl$_{3}$) δ 2.30 (s, 6 H), 6.88 (d, J = 8.4 Hz, 4H), 7.1 (d, J = 8.4 Hz, 4H); $^{13}$C NMR (100 MHz, CDCl$_{3}$) δ 20.8, 118.7, 130.3, 132.5, 155.5; GC-MS (EI, m/z): 198.2 (M$^{+}$). |
| 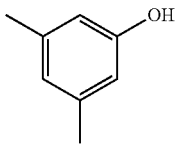 | 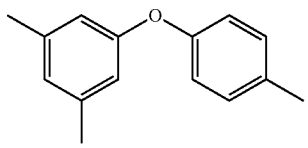<br>80% | $^{1}$H NMR (400 MHz, CDCl$_{3}$) δ 2.18 (s, 6H), 2.24 (s, 3H), 6.52 (s, 2H), 6.62 (s, 1H), 6.81 (d, J = 7.6 Hz, 2H), 7.03 (d, J = 7.6 Hz, 2H); $^{13}$C NMR (100 MHz, CDCl$_{3}$) δ 20.8, 21.4, 116.2, 119.2, 124.7, 130.3, 132.7, 139.5, 155, 157.9; GC-MS (EI, m/z): 212.2 (M$^{+}$). |
| 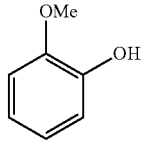 | 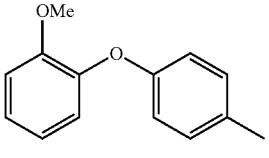<br>93% | $^{1}$H NMR (400 MHz, CDCl$_{3}$) δ 2.34 (s, 3H), 3.88 (s, 3H), 6.90 (m, 4H), 6.94 (m, 1H), 7.13 (m, 3H); $^{13}$C NMR (100 MHz, CDCl$_{3}$) δ 155.7, 151.4, 145.9, 132.3, 130.3, 124.5, 121.2, 117.7, 112.9, 56.2, 20.9; GC-MS (EI, m/z): 214.1 (M$^{+}$). |
| 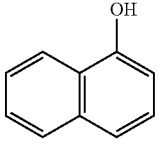 [SMILES: Oc1cccc2ccccc12] | 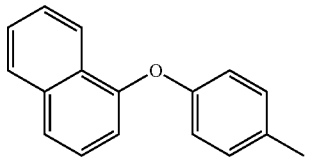<br>46% | $^{1}$H NMR (400 MHz, CDCl$_{3}$) δ 2.34 (s, 3 H), 6.88 (d, J = 7.6 Hz, 2H), 6.94-6.97 (m, 2H), 7.15 (d, J = 8.6 Hz, 2H), 7.35 (t, J = 8.0 Hz, 1 H), 7.45-7.54 (m, 2H), 7.58 (d, J = 8.2 Hz, 1H), 7.84-7.87 (m, 1H), 8.22-8.25 (m, 1H); $^{13}$C NMR (100 MHz, CDCl$_{3}$) δ 20.7, 112.6, 118.8, 122.1, 122.9, 125.8, 125.8, 126.5, 126.7, 127.7, 130.3, 132.8, 134.9, 153.6, 155.3; GC-MS (EI, m/z): 234.3 (M$^{+}$). |
| 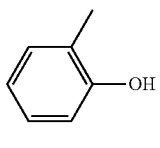 | 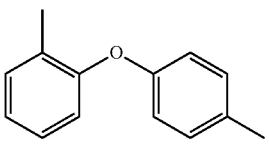<br>42% | $^{1}$H NMR (400 MHz, CDCl$_{3}$) δ 2.24 (s, 3 H), 2.29 (s, 3H), 6.80 (d, J = 8.4 Hz, 2H); 6.85 (d, J = 8.0 Hz, 1H), 7.01 (t, J = 7.2 Hz, 1H), 7.05-7.15 (m, 3H), 7.21 (d, J = 7.6 Hz, 1H); $^{13}$C NMR (100 MHz, CDCl$_{3}$) δ 16.3, 20.7, 117.6, 199.3, 123.7, 127.2, 129.8, 130.2, 131.5, 132, 155.1, 155.7; GC-MS (EI, m/z): 198.2 (M$^{+}$). |
| 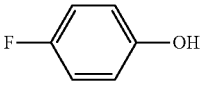 | 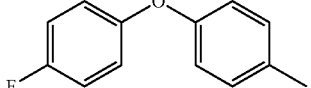<br>54% | $^{1}$H NMR (400 MHz, CDCl$_{3}$) δ 7.14 (d, 2H, J = 8.1 Hz), 7.07-6.92 (m, 4H), 6.89 (d, 2H, J = 8.2 Hz), 2.35 (s, 3H); $^{13}$C NMR (100 MHz, CDCl$_{3}$) δ 158.6 (d, J = 241.0 Hz), 155.3, 153.5, 132.9, 130.3, 120.0 (d, J = 8.2 Hz), 118.6, 116.2 (d, J = 23.3 Hz), 20.7; GC-MS (EI, m/z): 202.2 (M$^{+}$). |

| Phenol | product and yield | Characterization data of product |
|---|---|---|
| 4-hydroxyacetophenone | 57% | $^1$H NMR (400 MHz, CDCl$_3$) δ 2.37 (s, 3H), 2.57 (s, 3H), 6.95-6.98 (m, 4H), 7.18-7.21 (d, J = 8.26 Hz, 2H), 7.91-7.94 (d, J = 8.72, 2H); $^{13}$C NMR (100 MHz, CDCl$_3$) δ 20.8, 26.4, 116.8, 120.2, 130.5, 131.6, 134.3, 153.0, 162.4, 196.7; GC-MS (EI, m/z): 226.2 (M$^+$). |
| 3-cyanophenol | 32% | $^1$H NMR (400 MHz, CDCl$_3$) δ 2.37 (3H, s), 6.91-6.95 (2H, m), 7.16-7.22 (4H, m), 7.31-7.41 (2H, m); $^{13}$C NMR (100 MHz, CDCl$_3$) δ 157.7, 154.0, 131.5, 129.1, 128.7, 125.3, 123.2, 121.1, 118.7, 117.2, 112.3, 21.1; GC-MS (EI, m/z): 209.1 (M$^+$). |
| 3-hydroxypyridine | 55% | $^1$H NMR (400 MHz, CDCl$_3$) δ 8.39 (s, 1H), 8.33 (d, J = 2.3 Hz, 1H), 7.26-7.22 (m, 2H), 7.17 (d, J = 8.3 Hz, 2H), 6.98-6.90 (m, 2H), 2.35 (s, 3H); $^{13}$C NMR (100 MHz, CDCl$_3$) δ 155.7, 152.2, 141.1, 139.5, 134.3, 130.1, 124.1, 121.0, 119.5, 20.9; LC-MS (ESI, m/z): 186.2 (M + H)$^+$. |

Example 13 Synthesis of Diaryl Ether and Aryl Alkyl Ether Via Coupling Reaction of Aryl Chloride and R$_1$OH

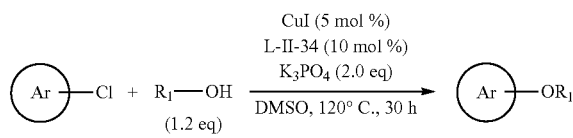

Aryl halide substrate (1.0 mmol), phenol (1.2 mmol), copper iodide (0.05 mmol), ligand L-II-34 (0.1 mmol), and potassium phosphate (2.0 mmol) were added into a 10 mL of Schlenk tube. The tube was then evacuated and backfilled with argon (this sequence was repeated three times), and then 1 mL of DMSO was added. The reaction mixture was well stirred at 120° C. for 30 hours. After cooling, the contents of the of Schlenk tube were washed with ethyl acetate, and filtrated through silica gel and kieselguhr. The filtrate was concentrated and purified by column chromatography to give the product diaryl ether. The results obtained are shown in the following table.

| aryl halide and phenol | product and yield | Characterization data of the product |
|---|---|---|
| 4-chlorobenzonitrile + 4-methoxyphenol | 87% | $^1$H NMR (400 MHz, CDCl$_3$) δ 3.83 (s, 3H), 6.94 (m, 4H), 7.01 (m, 2H), 7.58 (m, 2H); $^{13}$C NMR (100 MHz, CDCl$_3$) δ 55.9, 105.4, 115.5, 117.3, 119.2, 122.1, 134.3, 148.1, 157.3, 162.8; GC-MS (EI, m/z): 225.1 (M$^+$). |
| 4'-chloroacetophenone + 4-methoxyphenol | 67% | $^1$H NMR (400 MHz, CDCl$_3$) δ 7.90 (2H, d, J = 8.8 Hz), 7.00 (2H, d, J = 9.0 Hz), 6.92-6.88 (4H, m), 3.80 (3H, s), 2.55 (3H, s); $^{13}$C NMR (100 MHz, CDCl$_3$) δ 196.6, 162.9, 156.6, 148.4, 131.3, 130.5, 121.6, 116.3, 115.0, 55.6, 26.3; GC-MS (EI, m/z): 242.1 (M$^+$). |

| aryl halide and phenol | product and yield | Characterization data of the product |
|---|---|---|
| 2-chloronaphthalene; 4-methoxyphenol | naphthalen-2-yl (4-methoxyphenyl) ether, 85% | $^1$H NMR (400 MHz, CDCl$_3$) δ 7.80 (2H, d, J = 9.0 Hz), 7.66 (1H, d, J = 8.0 Hz), 7.42 (2H, m), 7.26 (1H, m), 7.18 (1H, m), 7.06 (2H, d, J = 8.9 Hz), 6.92 (2H, d, J = 9.0 Hz); $^{13}$C NMR (100 MHz, CDCl$_3$) δ 156.4, 156.0, 140.0, 134.3, 129.7, 127.6, 126.9, 126.4, 124.3, 121.0, 119.3, 114.9, 112.2, 55.6; GC-MS (EI, m/z): 250.1 (M$^+$). |
| 4-(4-chlorophenyl)morpholine; 4-methoxyphenol | 4-(4-(4-methoxyphenoxy)phenyl)morpholine, 87% | $^1$H NMR (400 MHz, CDCl$_3$) δ 6.91-6.81 (8H, m), 3.85 (4H, m), 3.77 (3H, s), 3.08 (4H, m); $^{13}$C NMR (100 MHz, CDCl$_3$) δ 155.3, 151.6, 151.3, 147.1, 119.6, 119.1, 117.3, 114.6, 66.9, 55.6, 50.2; LC-MS (ESI, m/z): 286.1 (M + H)$^+$. |
| N-(4-chlorophenyl)acetamide; p-cresol | N-(4-(p-tolyloxy)phenyl)acetamide, 80% | $^1$H NMR (400 MHz, CDCl$_3$) δ 7.69 (1H, s), 7.43-7.45 (2H, d, J = 8.8), 7.13-7.14 (2H, d, J = 8.2), 6.94-6.95 (2H, d, J = 8.8), 6.89-6.91 (2H, d, J = 8.4), 2.34 (3H, s), 2.17 (3H, s); $^{13}$C NMR (100 MHz, CDCl$_3$) δ 168.8, 155.2, 154.4, 135.9, 133.3, 133.0, 130.5, 129.0, 122.1, 119.2, 118.9, 24.6, 20.9; LC-MS (ESI, m/z): 242.1 (M + H)$^+$. |
| 1-chloro-4-(trifluoromethyl)benzene; m-cresol | 1-(2-methylphenoxy)-4-(trifluoromethyl)benzene, 81% | $^1$H NMR (400 MHz, CDCl$_3$) δ 7.56 (d, J = 8.6 Hz, 2H), 7.29-7.25 (m, 1H), 7.04-6.99 (m, 1H), 7.03 (d, J = 8.7 Hz, 2H), 6.87-6.84 (m, 2H), 2.36 (s, 3H); $^{13}$C NMR (100 MHz, CDCl$_3$) δ 160.7, 155.7, 140.4, 129.8, 127.0, 125.3, 124.6, 122.9, 120.6, 117.9, 117.0, 21.4; GC-MS (EI, m/z): 252.1 (M$^+$). |
| 1-chloro-3,5-dimethoxybenzene; phenol | 1,3-dimethoxy-5-phenoxybenzene, 93% | $^1$H NMR (400 MHz, CDCl$_3$) δ 7.38-7.31 (m, 2H), 7.15-7.09 (m, 1H), 7.07-7.02 (m, 2H), 6.23 (t, J = 2.2 Hz, 1H), 6.18 (d, J = 2.2 Hz, 2H), 3.75 (s, 6H); $^{13}$C NMR (100 MHz, CDCl$_3$) δ 161.72, 159.37, 156.82, 129.85, 123.63, 119.37, 97.38, 95.58, 55.54; GC-MS (EI, m/z): 230.1 (M$^+$). |
| 1-chloro-4-methoxybenzene; 3,5-dimethylphenol | 1-(3,5-dimethylphenoxy)-4-methoxybenzene, 87% | $^1$H NMR (400 MHz, CDCl$_3$) δ 7.01-6.95 (m, 2H), 6.92-6.86 (m, 2H), 6.70 (s, 1H), 6.58 (s, 2H), 3.82 (s, 3H), 2.28 (s, 6H); $^{13}$C NMR (126 MHz, CDCl$_3$) δ 158.61, 155.87, 150.42, 139.57, 124.33, 120.93, 115.44, 114.91, 55.77, 21.46; GC-MS (EI, m/z): 228.1 (M$^+$). |
| 3-chloroaniline; phenol | 3-phenoxyaniline, 86% | $^1$H NMR (400 MHz, CDCl$_3$) δ 7.37-7.30 (m, 2H), 7.10 (t, J = 8.0 Hz, 2H), 7.06-7.01 (m, 2H), 6.46-6.38 (m, 2H), 6.34 (t, J = 2.2 Hz, 1H), 3.45 (s, 2H); $^{13}$C NMR (126 MHz, CDCl$_3$) δ158.54, 157.24, 148.06, 130.45, 129.75, 123.26, 119.20, 110.20, 109.01, 105.64, 114.91, 55.77, 21.46; LC-MS (ESI, m/z): 186.1 (M + H)$^+$. |

-continued

| aryl halide and phenol | product and yield | Characterization data of the product |
|---|---|---|
| 4-fluoro-1-chlorobenzene; 3,5-dimethylphenol | 4-fluorophenyl 3,5-dimethylphenyl ether, 85% | $^1$H NMR (400 MHz, CDCl$_3$) δ 2.27 (3H, s), 6.58 (2H, s), 6.73 (1H, s), 6.9-7.1 (4H, m); $^{13}$C NMR (100 MHz, CDCl$_3$) δ 21.7, 116.4, 116.6 (d, J = 23 Hz), 120.9 (d, J = 8.6 Hz), 120.9, 125.3, 140.0, 153.5 (d, J = 2.6 Hz), 158.0, 159.1 (d, J = 241 Hz); GC-MS (EI, m/z): 216.1 (M$^+$). |
| 4-(hydroxymethyl)-1-chlorobenzene; 4-methylphenol | (4-(4-methylphenoxy)phenyl)methanol, 62% | $^1$H NMR (400 MHz, CDCl$_3$) δ 7.31 (d, J = 8.6 Hz, 2H), 7.14 (d, J = 8.6 Hz, 2H), 7.00-6.94 (m, 2H), 6.94-6.88 (m, 2H), 4.65 (s, 2H), 2.34 (s, 3H); $^{13}$C NMR (126 MHz, CDCl$_3$) δ 155.9, 154.0, 134.3, 131.5, 128.7, 128.0, 121.9, 117.1, 21.3; HRMS-ESI: m/z calcd for C$_{14}$H$_{15}$O$_2$ (M + H)$^+$: 215.1072, found: 215.1069. |
| 5-chloro-1,3-benzodioxole; phenol | 5-phenoxy-1,3-benzodioxole, 84% | $^1$H NMR (400 MHz, CDCl$_3$) δ 7.33-7.29 (m, 2H), 7.06 (t, J = 7.3 Hz, 1H), 6.96 (d, J = 8.0 Hz, 2H), 6.76 (d, J = 8.4 Hz, 1H), 6.58 (d, J = 2.3 Hz, 1H), 6.50 (dd, J = 2.3 Hz, J = 8.4 Hz, 1H), 5.97 (s, 2H); $^{13}$C NMR (100 MHz, CDCl$_3$) δ 158.63, 151.81, 148.80, 144.19, 130.09, 123.15, 118.25, 112.39, 108.71, 102.62, 101.94; GC-MS (EI, m/z): 214.1 (M$^+$). |
| 3-chloropyridine; 4-methylphenol | 3-(4-methylphenoxy)pyridine, 70% | $^1$H NMR (400 MHz, CDCl$_3$) δ 8.60-8.13 (m, 2H), 7.25-7.21 (m, 2H), 7.16 (d, J = 8.2 Hz, 2H), 6.92 (d, J = 8.5 Hz, 2H), 2.34 (s, 3H); $^{13}$C NMR (126 MHz, CDCl$_3$) δ 153.91, 143.98, 141.08, 133.93, 130.60, 130.47, 124.88, 124.12, 119.25, 20.83; HRMS-ESI: m/z calcd for C$_{12}$H$_{12}$NO (M + H)$^+$: 186.0919, found: 186.0916. |
| 6-chloroquinoline; 4-methylphenol | 6-(4-methylphenoxy)quinoline, 98% | $^1$H NMR (500 MHz, CDCl$_3$) δ 8.81 (s, 1H), 8.08 (d, J = 9.2 Hz, 1H), 7.98 (dd, J = 8.3, 1.5 Hz, 1H), 7.48 (dd, J = 9.2, 2.7 Hz, 1H), 7.34 (dd, J = 8.3, 4.2 Hz, 1H), 7.20 (d, J = 8.2 Hz, 2H), 7.16 (d, J = 2.7 Hz, 1H), 7.00 (d, J = 8.5 Hz, 2H), 2.37 (s, 3H); $^{13}$C NMR (126 MHz, CDCl$_3$) δ 156.23, 153.99, 148.80, 144.96, 135.10, 133.78, 131.23, 130.47, 129.12, 122.99, 121.45, 119.75, 112.00, 20.78; LC-MS (ESI, m/z): 235.1 (M + H)$^+$. |
| 5-chlorobenzo[b]thiophene; 4-methylphenol | 5-(4-methylphenoxy)benzo[b]thiophene, 86% | $^1$H NMR (400 MHz, CDCl$_3$) δ 7.81 (d, J = 8.7 Hz, 1H), 7.47 (d, J = 5.5 Hz, 1H), 7.39 (d, J = 2.4 Hz, 1H), 7.24 (dd, J = 5.5, 0.8 Hz, 1H), 7.16 (d, J = 8.5 Hz, 2H), 7.11 (dd, J = 8.7, 2.4 Hz, 1H), 6.95 (d, J = 8.5 Hz, 2H), 2.36 (s, 3H); $^{13}$C NMR (126 MHz, CDCl$_3$) δ 155.51, 155.31, 140.88, 134.53, 132.83, 130.37, 128.03, 123.77, 123.51, 118.88, 117.26, 112.56, 20.84; HRMS-EI: m/z calcd for C$_{15}$H$_{12}$OS (M$^+$): 240.0603, found: 240.0609. |
| 2-chloropyrazine; 4-methylphenol | 2-(4-methylphenoxy)pyrazine, 83% | $^1$H NMR (400 MHz, CDCl$_3$) δ 8.43 (1H, d, J = 1.1), 8.25 (1H, d, J = 2.7), 8.11 (1H, dd, J = 2.7, 1.1), 7.24 (2H, d, J = 8.5), 7.07 (2H, d, J = 8.5), 2.39 (3H, s); $^{13}$C NMR (100 MHz, CDCl$_3$) δ 160.5, 150.7, 141.1, 138.3, 135.8, 135.1, 130.3, 121.1, 20.9; HRMS-ESI: m/z calcd for C$_{11}$H$_{11}$N$_2$O (M + H)$^+$: 187.0871, found: 187.0875. |

Example 14 Synthesis of 4,4'-dimethyldiphenylsulfide

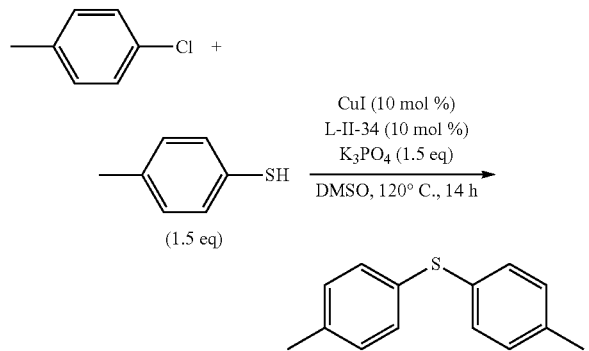

4-methylthiophenol (1.5 mmol), copper iodide (0.1 mmol), ligand L-II-34 (0.1 mmol) and potassium phosphate (1.5 mmol) were added into a 10 mL of Schlenk tube. The tube was then evacuated and backfilled with argon (this sequence was repeated three times), and then 1-chloro-4-methylbenzene (1.0 mmol) and 1 mL of DMSO were added. The reaction mixture was well stirred at 120° C. for 14 hours. After cooling, the contents of the of Schlenk tube were washed with ethyl acetate, and filtrated through silica gel and kieselguhr. The filtrate was concentrated and purified by column chromatography to give the product 4,4'-dimethyldiphenylsulfide (36.4 mg, yield 17%).

$^1$H NMR (400 MHz, CDCl$_3$) δ 2.32 (s, 6H), 7.10 (d, J=7.8 Hz, 2H), 7.22-7.25 (m, 4H); $^{13}$C NMR (100 MHz, CDCl$_3$) δ 21.2, 130.0, 131.2, 132.8, 137.0.

Example 15 Synthesis of Aromatic Amines by Reaction of Aryl Bromides/Iodides and Amines

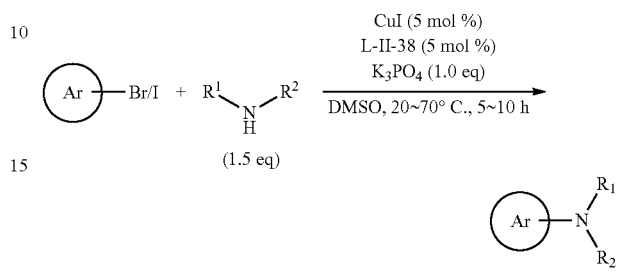

Aryl bromide/iodide substrates (1.0 mmol), amine (1.2 mmol), copper iodide (0.05 mmol), ligand L-II-38 (0.05 mmol) and potassium phosphate (1.0 mmol) were added into a 10 mL of Schlenk tube. The tube was then evacuated and backfilled with argon (this sequence was repeated three times), and then 1 mL of DMSO was added. The reaction mixture was well stirred at 20-70° C. for 5-10 hours. After cooling, the contents of the of Schlenk tube were washed with ethyl acetate, and filtrated through silica gel and kieselguhr. The filtrate was concentrated and purified by column chromatography to give the product aromatic amines. The results obtained are shown in the following table.

| Substrate, Product and Yield | Temperature and Time | Characterization data of product |
|---|---|---|
| Ph-Br + BnNH$_2$ → Ph-NHBn, 51% | 70° C., 6 h | 1H NMR (400 MHz, CDCl$_3$) δ 7.42-7.31 (m, 4H), 7.27 (t, J = 6.8 Hz, 1H), 7.17 (t, J = 7.8 Hz, 2H), 6.71 (t, J = 7.3 Hz, 1H), 6.63 (d, J = 8.1 Hz, 2H), 4.32 (s, 2H), 4.02 (br s, 1H); $^{13}$C NMR (100 MHz, CDCl$_3$) δ 148.26, 139.54, 129.38, 128.75, 127.62, 127.34, 117.66, 112.94, 48.41; HRMS-ESI: m/z calcd for C$_{13}$H$_{14}$N (M + H)$^+$: 184.1121, found: 184.1124. |
| Ph-I + BnNH$_2$ → Ph-NHBn, 95% | 70° C., 6 h | |
| Ph-I + BnNH$_2$ → Ph-NHBn, 35% | 24° C., 6 h | |
| Ph-I + H$_2$N-CH(iPr)-CO$_2$H → Ph-NH-CH(iPr)-CO$_2$H, 84% | 70° C., 10 h | $^1$H NMR (400 MHz, CDCl$_3$) δ 7.17 (t, J = 7.8 Hz, 2H), 6.73 (t, J = 7.4 Hz, 1H), 6.65 (d, J = 8.0 Hz, 2H), 3.85 (d, J = 5.4 Hz, 1H), 2.13-2.14 (m, 1H), 1.06 (q, J = 3.6 Hz, 6H); $^{13}$C NMR (100 MHz, CDCl$_3$) δ 176.3, 147.3, 129.3, 118.2, 113.6, 62.3, 19.2, 18.3; HRMS-ESI: m/z calcd for C$_{11}$H$_{16}$NO$_2$ (M + H)$^+$: 194.1182, found: 194.1173. |

| Substrate, Product and Yield | Temperature and Time | Characterization data of product |
|---|---|---|
| 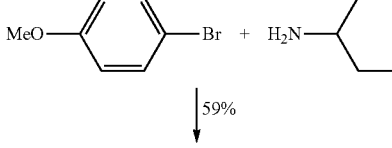 59% | 70° C., 5 h | $^1$H NMR (500 MHz, CDCl$_3$) δ 6.78 (d, J = 8.8 Hz, 2H), 6.59 (d, J = 8.8 Hz, 2H), 3.76 (s, 3H), 3.20-3.15 (m, 2H), 2.06 (d, J = 10.2 Hz, 2H), 1.79-1.75 (m, 2H), 1.67-1.65 (m, 1H), 1.40-1.32 (m, 2H), 1.26-1.21 (m, 1H), 1.17-1.09 (m, 2H): $^{13}$C NMR (125 MHz, CDCl$_3$) δ 152.1, 141.8, 115.1, 115.0, 56.0, 53.0, 33.8, 26.2, 25.3; HRMS-ESI: m/z calcd for C$_{13}$H$_{20}$NO (M + H)$^+$: 206.1539, found: 206.1543. |
| 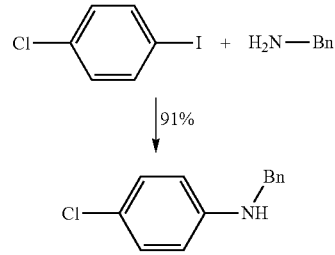 [SMILES: Clc1ccc(I)cc1 ; NCc1ccccc1 ; Clc1ccc(NCc2ccccc2)cc1] 91% | 50° C., 10 h | $^1$H NMR (400 MHz, CDCl$_3$) δ 7.50-7.40 (m, 4H), 7.39-7.31 (m, 1H), 7.23-7.13 (m, 2H), 6.65-6.54 (m, 2H), 4.34 (s, 2H), 3.97 (br s, 1H); $^{13}$C NMR (100 MHz, CDCl$_3$) δ 146.67, 138.97, 129.09, 128.74, 127.45, 127.40, 122.06, 113.99, 48.32; HRMS-ESI: m/z calcd for C$_{13}$H$_{13}$ClN (M + H)$^+$: 218.0731, found: 218.0735. |

Example 16 Synthesis of Diaryl Ethers Via Reaction of Aryl Bromides with phenols

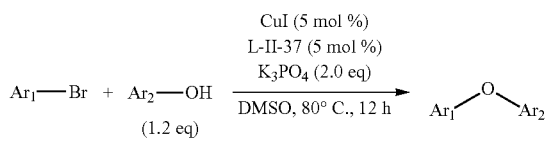

Aryl halide substrate (1.0 mmol), phenol (1.2 mmol), copper iodide (0.05 mmol), ligand L-II-37 (0.05 mmol), potassium phosphate (2.0 mmol) were added into a 10 mL of Schlenk tube. The tube was then evacuated and backfilled with argon (this sequence was repeated three times), and then 1 mL of DMSO was added. The reaction mixture was well stirred at 80° C. for 12 hours. After cooling, the contents of the of Schlenk tube were washed with ethyl acetate, and filtrated through silica gel and kieselguhr. The filtrate was concentrated and purified by column chromatography to give the product diaryl ether. The results obtained are shown in the following table.

| aryl bromide and phenol | product and yield | Characterization data of product |
|---|---|---|
| 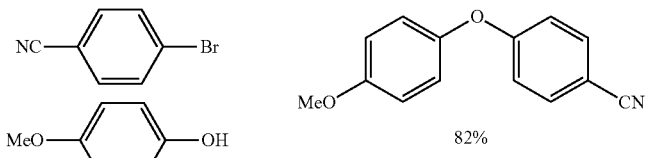 | 82% | $^1$H NMR (400 MHz, CDCl$_3$) δ 3.83 (s, 3H), 6.94 (m, 4H), 7.01 (m, 2H), 7.58 (m, 2H); $^{13}$C NMR (100 MHz, CDCl$_3$) δ 55.9, 105.4, 115.5, 117.3, 119.2, 122.1, 134.3, 148.1, 157.3, 162.8; GC-MS (EI, m/z): 225.1 (M$^+$). |
| 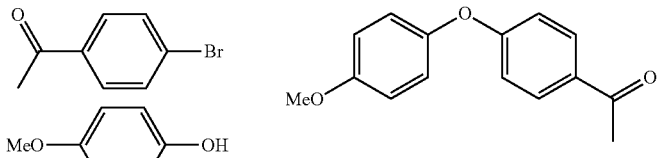 | 83% | $^1$H NMR (400 MHz, CDCl$_3$) δ 7.90 (2H, d, J = 8.8 Hz), 7.00 (2H, d, J = 9.0 Hz), 6.92-6.88 (4H, m), 3.80 (3H, s), 2.55 (3H, s); $^{13}$C NMR (100 MHz, CDCl$_3$) δ 196.6, 162.9, 156.6, 148.4, 131.3, 130.5, 121.6, 116.3, 115.0, 55.6, 26.3; GC-MS (EI, m/z): 242.1 (M$^+$). |

| aryl bromide and phenol | product and yield | Characterization data of product |
|---|---|---|
| 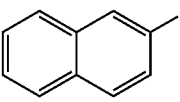 | 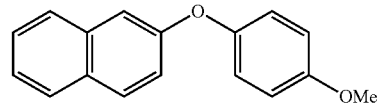 81% | $^1$H NMR (400 MHz, CDCl$_3$) δ 7.80 (2H, d, J = 9.0 Hz), 7.66 (1H, d, J = 8.0 Hz), 7.42 (2H, m), 7.26 (1H, m), 7.18 (1H, m), 7.06 (2H, d, J = 8.9 Hz), 6.92 (2H, d, J = 9.0 Hz); $^{13}$C NMR (100 MHz, CDCl$_3$) δ 156.4, 156.0, 140.0, 134.3, 129.7, 127.6, 126.9, 126.4, 124.3, 121.0, 119.3, 114.9, 112.2, 55.6; GC-MS (EI, m/z): 250.1 (M$^+$). |
| 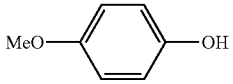 | 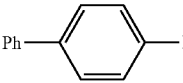 92% | $^1$H NMR (400 MHz, CDCl$_3$) δ 2.35 (s, 3H), 6.88 (m, 2H), 6.93 (d, J = 7.5 Hz, 1H), 7.06 (m, 2H), 7.23 (m, 1H), 7.35 (m, 1H), 7.43 (m, 2H), 7.58 (m, 4H); $^{13}$C NMR (100 MHz, CDCl$_3$) δ 157.1, 156.0, 134.0, 138.1, 133.9, 129.2, 128.7, 128.3, 127.9, 127.6, 122.3, 118.0, 116.3, 115.7, 21.3; GC-MS (EI, m/z): 260.1 (M$^+$). |
| 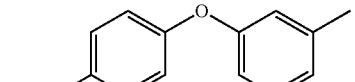 | 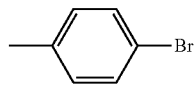 91% | $^1$H NMR (400 MHz, CDCl$_3$) δ 7.30 (s, 2H), 7.08-7.14 (m, 2H), 6.88-6.93 (m, 4H), 2.31 (s, 3H,), 1.32 (s, 9H); $^{13}$C NMR (100 MHz, CDCl$_3$) δ 155.35, 155.08, 145.69, 132.62, 130.22, 126.51, 118.95, 118.65, 117.95, 115.96, 34.32, 31.58, 20.77; GC-MS (EI, m/z): 240.1 (M$^+$). |
| 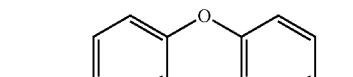 | 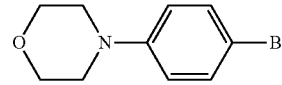 86% | $^1$H NMR (400 MHz, CDCl$_3$) δ 6.91-6.81 (8H, m), 3.85 (4H, m), 3.77 (3H, s), 3.08 (4H, m); $^{13}$C NMR (100 MHz, CDCl$_3$) δ 155.3, 151.6, 151.3, 147.1, 119.6, 119.1, 117.3, 114.6, 66.9, 55.6, 50.2; LC-MS (ESI, m/z): 286.1 (M + H)$^+$. |
| 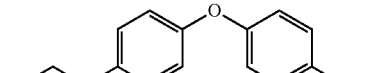 | 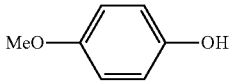 94% | $^1$H NMR (400 MHz, CDCl$_3$) δ 7.56 (d, J = 8.6 Hz, 2H), 7.29-7.25 (m, 1H), 7.04-6.99 (m, 1H), 7.03 (d, J = 8.7 Hz, 2H), 6.87-6.84 (m, 2H), 2.36 (s, 3H); $^{13}$C NMR (100 MHz, CDCl$_3$) δ 160.7, 155.7, 140.4, 129.8, 127.0, 125.3, 124.6, 122.9, 120.6, 117.9, 117.0, 21.4; GC-MS (EI, m/z): 252.1 (M$^+$). |
| 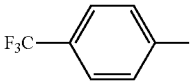 | 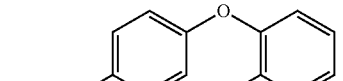 91% | $^1$H NMR (400 MHz, CDCl$_3$) δ 7.38-7.31 (m, 2H), 7.15-7.09 (m, 1H), 7.07-7.02 (m, 2H), 6.23 (t, J = 2.2 Hz, 1H), 6.18 (d, J = 2.2 Hz, 2H), 3.75 (s, 6H); $^{13}$C NMR (100 MHz, CDCl$_3$) δ 161.72, 159.37, 156.82, 129.85, 123.63, 119.37, 97.38, 95.58, 55.54; GC-MS (EI, m/z): 230.1 (M$^+$). |
| 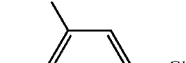 | 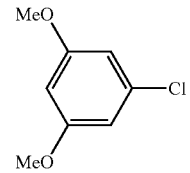 88% | $^1$H NMR (400 MHz, CDCl$_3$) δ 7.01-6.95 (m, 2H), 6.92-6.86 (m, 2H), 6.70 (s, 1H), 6.58 (s, 2H), 3.82 (s, 3H), 2.28 (s, 6H); $^{13}$C NMR (126 MHz, CDCl$_3$) δ 158.61, 155.87, 150.42, 139.57, 124.33, 120.93, 115.44, 114.91, 55.77, 21.46; GC-MS (EI, m/z): 228.1 (M$^{+)}$. |

| aryl bromide and phenol | product and yield | Characterization data of product |
|---|---|---|
| 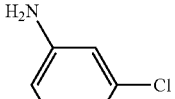 | 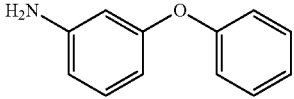  89% | $^1$H NMR (400 MHz, CDCl$_3$) δ 7.37-7.30 (m, 2H), 7.10 (t, J = 8.0 Hz, 2H), 7.06-7.01 (m, 2H), 6.46-6.38 (m, 2H), 6.34 (t, J = 2.2 Hz, 1H), 3.45 (s, 2H); $^{13}$C NMR (126 MHz, CDCl$_3$) δ 158.54, 157.24, 148.06, 130.45, 129.75, 123.26, 119.20, 110.20, 109.01, 105.64, 114.91, 55.77, 21.46; LC-MS (ESI, m/z): 186.1 (M + H)$^+$. |
| 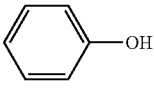 | 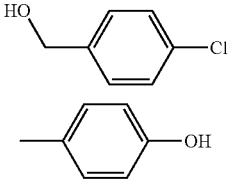  81% | $^1$H NMR (400 MHz, CDCl$_3$) δ 7.31 (d, J = 8.6 Hz, 2H), 7.14 (d, J = 8.6 Hz, 2H), 7.00-6.94 (m, 2H), 6.94-6.88 (m, 2H), 4.65 (s, 2H), 2.34 (s, 3H); $^{13}$C NMR (126 MHz, CDCl$_3$) δ 155.9, 154.0, 134.3, 131.5, 128.7, 128.0, 121.9, 117.1, 21.3; HRMS-ESI: m/z calcd for C$_{14}$H$_{15}$O$_2$ (M + H)$^+$: 215.1072, found: 215.1069. |
| 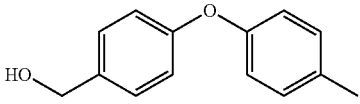 | 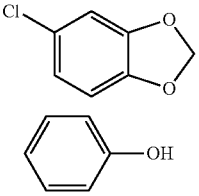  83% | $^1$H NMR (400 MHz, CDCl$_3$) δ 7.33-7.29 (m, 2H), 7.06 (t, J = 7.3 Hz, 1H), 6.96 (d, J = 8.0 Hz, 2H), 6.76 (d, J = 8.4 Hz, 1H), 6.58 (d, J = 2.3 Hz, 1H), 6.50 (dd, J = 2.3 Hz, J = 8.4 Hz, 1H), 5.97 (s, 2H); $^{13}$C NMR (100 MHz, CDCl$_3$) δ 158.63, 151.81, 148.80, 144.19, 130.09, 123.15, 118.25, 112.39, 108.71, 102.62, 101.94; GC-MS (EI, m/z): 214.1 (M$^+$). |
| 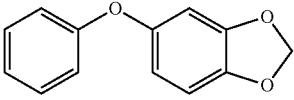 | 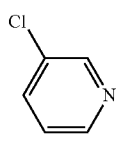  85% | $^1$H NMR (400 MHz, CDCl$_3$) δ 8.60-8.13 (m, 2H), 7.25-7.21 (m, 2H), 7.16 (d, J = 8.2 Hz, 2H), 6.92 (d, J = 8.5 Hz, 2H), 2.34 (s, 3H); $^{13}$C NMR (126 MHz, CDCl$_3$) δ 153.91, 143.98, 141.08, 133.93, 130.60, 130.47, 124.88, 124.12, 119.25, 20.83; HRMS-ESI: m/z calcd for C$_{12}$H$_{12}$NO (M + H)$^+$: 186.0919, found: 186.0916. |
| 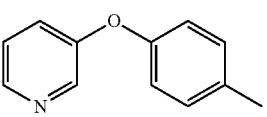 | 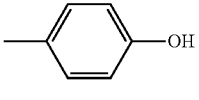  91% | $^1$H NMR (500 MHz, CDCl$_3$) δ 8.81 (s, 1H), 8.08 (d, J = 9.2 Hz, 1H), 7.98 (dd, J = 8.3, 1.5 Hz, 1H), 7.48 (dd, J = 9.2, 2.7 Hz, 1H), 7.34 (dd, J = 8.3, 4.2 Hz, 1H), 7.20 (d, J = 8.2 Hz, 2H), 7.16 (d, J = 2.7 Hz, 1H), 7.00 (d, J = 8.5 Hz, 2H), 2.37 (s, 3H); $^{13}$C NMR (126 MHz, CDCl$_3$) δ 156.23, 153.99, 148.80, 144.96, 135.10, 133.78, 131.23, 130.47, 129.12, 122.99, 121.45, 119.75, 112.00, 20.78; LC-MS (ESI, m/z): 235.1 (M + H)$^+$. |
| 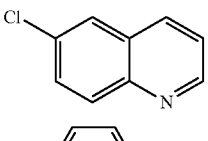 | 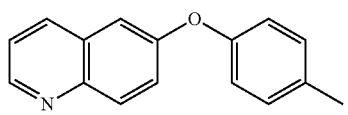  87% | $^1$H NMR (400 MHz, CDCl$_3$) δ 7.81 (d, J = 8.7 Hz, 1H), 7.47 (d, J = 5.5 Hz, 1H), 7.39 (d, J = 2.4 Hz, 1H), 7.24 (dd, J = 5.5, 0.8 Hz, 1H), 7.16 (d, J = 8.5 Hz, 2H), 7.11 (dd, J = 8.7, 2.4 Hz, 1H), 6.95 (d, J = 8.5 Hz, 2H), 2.36 (s, 3H); $^{13}$C NMR (126 MHz, CDCl$_3$) δ 155.51, 155.31, 140.88, 134.53, 132.83, 130.37, 128.03, 123.77, 123.51, 118.88, 117.26, 112.56, 20.84; HRMS-EI: m/z calcd for C$_{15}$H$_{12}$OS (M$^+$): 240.0603, found: 240.0609. |
| 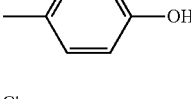 | 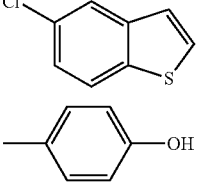  89% | $^1$H NMR (400 MHz, CDCl$_3$) δ 8.43 (1H, d, J = 1.1), 8.25 (1H, d, J = 2.7), 8.11 (1H, dd, J = 2.7, 1.1), 7.24 (2H, d, J = 8.5), 7.07 (2H, d, J = 8.5), 2.39 (3H, s); $^{13}$C NMR (100 MHz, CDCl$_3$) δ 160.5, 150.7, 141.1, 138.3, 135.8, 135.1, 130.3, 121.1, 20.9; HRMS-ESI: m/z calcd for C$_{11}$H$_{11}$N$_2$O (M + H)$^+$: 187.0871, found: 187.0875. |

Example 17 Synthesis of N-4'-methoxyphenylpyrrole Via Coupling Reaction of 4-chloroanisole with Pyrrole

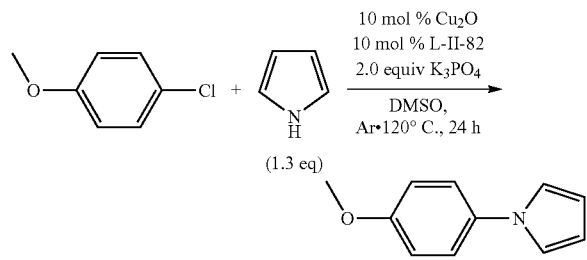

(1.3 eq)

Cuprous oxide (0.1 mmol), ligand (0.1 mmol), potassium phosphate (2.0 mmol) were added into a 10 mL of Schlenk tube. The tube was then evacuated and backfilled with argon (this sequence was repeated three times), and then 4-chloroanisole (1.0 mmol), pyrrole (1.3 mmol) and 0.5 mL of DMSO were added. The reaction mixture was stirred well at 120° C. for 24 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography (petroleum ether:ethyl acetate=50:1) to give the product N-4'-methoxyphenylpyrrole (88 mg, 51% yield).

$^1$H NMR (400 MHz, CDCl$_3$): δ 7.29-7.33 (m, 2H), 6.98-7.01 (m, 2H), 6.90-6.96 (m, 2H), 6.32 (t, J=2.0 Hz, 2H), 3.83 (s, 3H). GC-MS (EI): m/z=173 [M]$^+$.

Example 18 Synthesis of N-4'-methoxyphenylpyrrole Via Coupling Reaction of 4-chloroanisole with Pyrrole The operation of this example was the same as that of Example 17 except different oxalamide ligands was used. The results of the supplemental experiment are shown in the following table.

| Ligand | Yield/% | Ligand | Yield/% | Ligand | Yield/% |
|---|---|---|---|---|---|
| L-II-82 | 51 | L-II-83 | 42 | L-II-84 | 25 |
| L-II-85 | 48 | L-II-86 | 23 | L-II-87 | 18 |
| L-II-88 | 36 | L-II-89 | 17 | L-II-21 | 32 |
| L-II-79 | 28 | L-II-80 | 33 | L-II-81 | 30 |
| L-II-98 | 22 | L-II-99 | 36 | | |

Example 19 Synthesis of N-aryl Heterocycles

Cuprous oxide (0.1 mmol), ligand (0.1 mmol), potassium phosphate (2.0 mmol) were added into a 10 mL of Schlenk tube. The tube was then evacuated and backfilled with argon (three times), and then 4-chloroanisole (1.0 mmol), nitrogen heteroaryl compound (1.3 mmol) and 0.5 mL of DMSO were added. The reaction mixture was stirred well at 120° C. for 24 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography to give the product N-aryl heterocycles.

Different N-heteroaromatic rings were used in this example. The results are given in the following table.

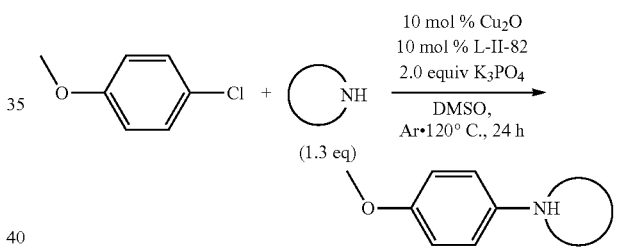

(1.3 eq)

| Product and Yield | Characterization data of product |
|---|---|
| 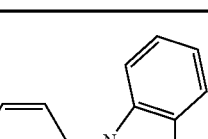 yield: 55% | $^1$H NMR (400 MHz, CDCl$_3$) δ: 7.72 (d, J = 7.5 Hz, 1H), 7.49-7.41 (m, 3H), 7.30 (d, J = 3.3 Hz, 1H), 7.26-7.15 (m, 2H), 7.06-7.03 (m, 2H), 6.68 (d, J = 3.0 Hz, 1H), 3.89 (s, 3H); $^{13}$C NMR (101 MHz, CDCl$_3$) δ: 158.2, 136.3, 132.8, 128.9, 128.3, 125.9, 122.1, 120.9, 120.0, 114.7, 110.3, 102.8, 55.6. HRMS (ESI) Calcd for C$_{15}$H$_{13}$NO (M + H+): 223.0997, found 223.1002. |
|  47% | $^1$H NMR (300 MHz, CDCl$_3$) δ: 8.14 (d, J = 7.8 Hz, 2H), 7.47-7.42 (m, 2H), 7.39-7.36 (m, 2H), 7.33-7.20 (m, 4H), 7.12-7.07 (m, 2H), 3.90 (s, 3H); $^{13}$C NMR (101 MHz, CDCl$_3$) δ: 158.8, 141.3, 130.2, 128.5, 125.8, 123.0, 120.2, 119.6, 115.0, 109.6, 55.6. HRMS (ESI) Calcd for C$_{19}$H$_{15}$NO (M + H+): 273.1154, found 273.1157. |

| Product and Yield | Characterization data of product |
|---|---|
| 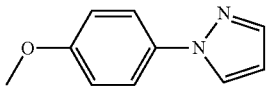 21% | $^1$H NMR (400 MHz, CDCl$_3$, δ ppm): δ 7.81 (d, J = 3.2 Hz, 1H), 7.69 (d, J = 1.6 Hz, 1H), 7.59-7.55 (m, 2H), 6.98-6.93 (m, 2H), 6.42 (t, J = 2.4 Hz, 1H), 3.83 (s, 3H) ppm. 13C NMR (100 MHz, CDCl3, δ ppm): δ 158.2, 140.6, 134.0, 126.8, 119.9, 114.5, 107.2, 55.6. HRMS (ESI) Calcd for C$_{10}$H$_{10}$N$_2$O (M + H+): 174.0793, found 174.0792. |
| 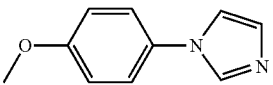 17% | $^1$H NMR (400 MHz, CDCl$_3$) δ: 7.77 (s, 1H), 7.33-7.28 (m, 2H), 7.20 (d, J = 6.6 Hz, 2H), 7.03-6.97 (m, 2H), 3.85 (s, 3H); $^{13}$C NMR (101 MHz, CDCl$_3$) δ: 158.8, 135.8, 130.7, 130.0, 123.2, 118.7, 114.8, 55.6. HRMS (ESI) Calcd for C$_{10}$H$_{10}$N$_2$O (M + H+): 174.0793, found 174.0796. |

Example 20 Synthesis of N-(4-methoxyphenyl)benzamide Via Coupling Reaction of 4-chloroanisole with Benzamide

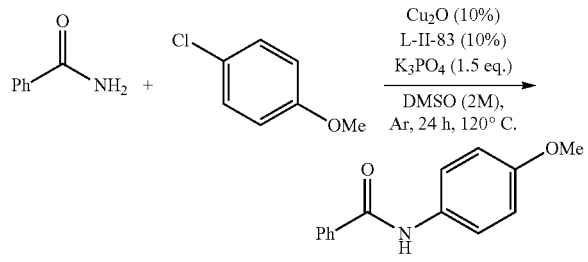

Cuprous oxide (0.1 mmol), ligand L-II-83 (0.1 mmol), potassium phosphate (1.5 mmol) were added into a 10 mL of Schlenk tube. The tube was then evacuated and backfilled with argon (three times), and then 4-chloroanisole (1.0 mmol), benzamide (1.3 mmol) and 0.5 mL of DMSO were added. The reaction mixture was stirred well at 120° C. for 24 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography (petroleum ether:ethyl acetate=2:1) to give the product N-(4-methoxyphenyl)benzamide (127 mg, 56% yield).

$^1$H NMR (400 MHz, CDCl$_3$): δ 7.85 (d, J=7.2 Hz, 3H), 7.55-7.51 (m, 3H), 7.46 (t, J=7.6 Hz, 2H), 6.90 (d, J=8.8 Hz, 2H), 3.81 (s, 3H). LC-MS (ESI, m/z): 228.1 (M+H)$^+$.

Example 21 Synthesis of N-(4-methoxyphenyl)benzamide Via Coupling Reaction of 4-chloroanisole with Benzamide The operation of this example was the same as that of Example 20 except that different oxalic diamide ligands were used. The results of the experiment are shown in the following table.

| Ligand | Yield/% | Ligand | Yield/% | Ligand | Yield/% |
|---|---|---|---|---|---|
| L-II-82 | 53 | L-II-83 | 56 | L-II-84 | 15 |
| L-II-85 | 30 | L-II-86 | 20 | L-II-87 | 32 |
| L-II-88 | 37 | L-II-89 | 35 | L-II-21 | 20 |
| L-II-79 | 25 | L-II-80 | 28 | L-II-81 | 38 |
| L-II-90 | 60 | L-II-90 | 75 (The reaction time was extended to 36 hours) | | |

Example 22 Synthesis of N-(4-methoxyphenyl)benzamide Via Coupling Reaction of 4-chloroanisole with Benzamide

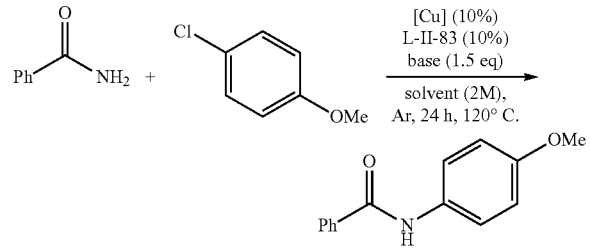

The operation of this example was the same as that of Example 20 except that different copper salt catalysts, bases, solvents and temperatures were used. The results obtained are shown in the following table.

| Entry | Copper salt | Base | Solvent | Temperature/° C. | Yield/% |
|---|---|---|---|---|---|
| 1 | CuI | K$_3$PO$_4$ | DMSO | 120 | 40 |
| 2 | CuBr | K$_3$PO$_4$ | DMSO | 120 | 45 |
| 3 | CuCl | K$_3$PO$_4$ | DMSO | 120 | 41 |
| 4 | CuTc | K$_3$PO$_4$ | DMSO | 120 | 38 |
| 5 | Cu(OAc)$_2$ | K$_3$PO$_4$ | DMSO | 120 | 37 |
| 6 | Cu$_2$O | K$_3$PO$_4$ | DMSO | 120 | 56 |
| 7 | CuBr$_2$ | K$_3$PO$_4$ | DMSO | 120 | 29 |
| 8 | Cu$_2$O | K$_3$PO$_4$ | DMSO | 120 | 28 |
| 9 | Cu$_2$O | K$_3$PO$_4$ | DMSO | 120 | 39 |
| 11 | Cu$_2$O | K$_3$PO$_4$ | DMF | 120 | 28 |
| 12 | Cu$_2$O | K$_3$PO$_4$ | MeCN | 120 | 42 |
| 13 | Cu$_2$O | K$_3$PO$_4$ | DMSO | 130 | 58 |
| 14 | Cu$_2$O | K$_3$PO$_4$ | DMSO | 140 | 55 |

Example 23 Synthesis of N-aryl Benzamides

Cuprous oxide (0.1 mmol), ligand (0.1 mmol) and potassium phosphate (1.5 mmol) were added into a 10 mL of Schlenk tube. The tube was then evacuated and backfilled with argon (three times), and then 1-chloro-4-(methoxyl)

benzene (1.0 mmol), amide (1.3 mmol) and 0.5 mL of DMSO were added. The reaction mixture was stirred well at 120° C. for 24 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography to give N-aryl benzamide.

In this example, different chlorobenzenes and amides were used. The results are given in the following table.

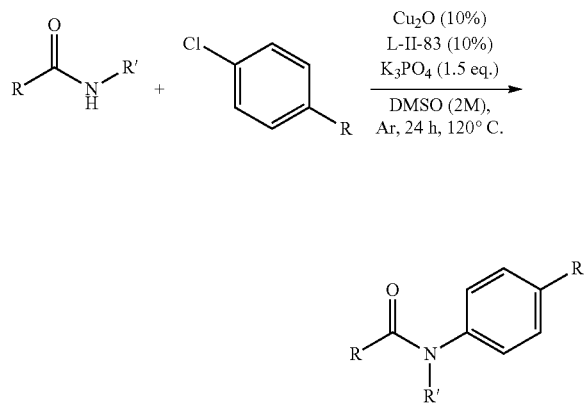

Example 24 Coupling of 4-chloroanisole with Sodium Alkylsulfinate or Sodium Arylsulfinate

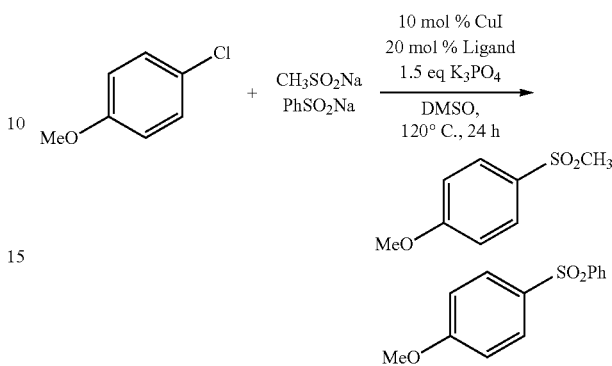

Sodium methanesulfinate (0.6 mmol), copper iodide (0.05 mmol), ligand (0.1 mmol) and potassium phosphate (1.5 mmol) were added into a 10 mL of Schlenk tube. The tube was evacuated and backfilled with argon (three times), and then 4-chloroanisole (0.5 mmol) and 1 mL of DMSO were added. The reaction mixture was stirred well at 120° C. for 24 hours. After cooling, the contents of the of Schlenk tube were washed with ethyl acetate, and filtered through silica

| Product and Yield | Characterization data of product |
|---|---|
| 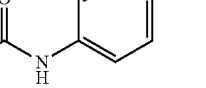 yield: 50% | $^1$H NMR (400 MHz, CDCl$_3$): δ 7.81 (br s, 1H), 7.37 (d, J = 9.0 Hz, 2H), 6.81 (d, J = 9.0 Hz, 2H), 3.76 (s, 3H), 2.10 (s, 3H). LC-MS (ESI, m/z): 165.1 (M + H)$^+$. |
| 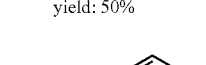 yield: 15% | $^1$H NMR (400 MHz, CDCl$_3$): d = 7.28 (d, J = 7.6 Hz, 2H), 7.20-7.15 (m, 3H), 6.94 (d, J = 8.4 Hz, 2H), 6.72 (d, J = 8.4 Hz, 2H), 3.71 (s, 3H), 3.44 ppm (s, 3H); LC-MS (ESI, m/z): 242.1 (M + H)$^+$. |
| 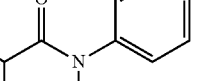 yield: 35% | $^1$H NMR (400 MHz, CDCl$_3$): δ 7.50 (d, J = 9.0 Hz, 2H), 6.91 (d, J = 9.0 Hz, 2H), 3.85-3.80 (m, 5H,), 2.60 (t, 2H, J = 8.0 Hz, J = 8.0 Hz), 2.20-2.14 (m, 2H); LC-MS (ESI, m/z): 192.1 (M + H)$^+$. |
| 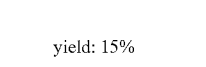 yield: 58% | $^1$H NMR (400 MHz, CDCl$_3$): δ 7.96 (br s, 1H), 7.84 (d, J = 7.2 Hz, 2H), 7.54-7.49 (m, 3H), 7.46-7.41 (m, 2H), 7.14 (d, J = 8.0 Hz, 2H), 2.33 (s, 3H); LC-MS (ESI, m/z): 211.1 (M + H)$^+$. | gel and celite column. The filtrate was concentrated and purified by column chromatography to give the product.

1-methoxy-4-(methylsulfonyl)benzene: $^1$H NMR (400 MHz, CDCl$_3$) δ 3.05 (s, 3H), 3.90 (s, 3H), 7.04 (dd, J=7.5, 2.1 Hz, 2H), 7.88 (dd, J=7.5, 2.1 Hz, 2H); ELMS (m/z) 186 (M+)

1-methoxy-4-(phenylsulfonyl)benzene: $^1$H NMR (400 MHz, CDCl$_3$) δ 3.84 (s, 3H), 6.96 (m, 2H), 7.51 (m, 3H), 7.90 (m, 4H); ELMS (m/z) 248 (M+).

The results obtained by using different ligands are listed in the following table.

| Ligand | Yield/% | Ligand | Yield/% | Ligand | Yield/% |
|---|---|---|---|---|---|
| PhSO$_2$Na | | | | | |
| L-I-16 | 20 | L-II-3 | 30 | L-II-5 | 15 |
| L-II-7 | 10 | L-II-18 | 16 | L-II-19 | 20 |
| L-II-44 | 5 | L-II-47 | 8 | L-II-53 | 15 |
| CH$_3$SO$_2$Na | | | | | |
| L-II-31 | 17 | L-II-37 | 24 | — | — |

Example 25 Synthesis of 4-methoxyphenol by Copper-Catalyzed Reaction of 4-chloroanisole

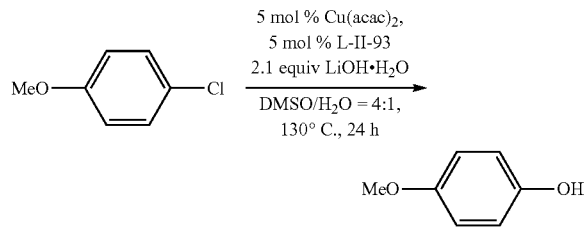

Copper acetylacetonate (Cu(acac)$_2$) (0.025 mmol), ligand L-II-93 (0.025 mmol), lithium hydroxide monohydrate (1.05 mmol) were added into a 10 mL of Schlenk tube. The tube was evacuated and backfilled with argon (three times), and then 4-chloroanisole (0.5 mmol), 0.8 mL of DMSO and 0.2 mL of H$_2$O were added successively under argon. The reaction mixture was stirred well at 130° C. for 24 hours. After cooling, 2 mL of hydrochloric acid (1 mol/L), water and ethyl acetate were added and separated. The aqueous phase was extracted twice with ethyl acetate. The combined organic phase was dried over anhydrous sodium sulfate. After concentration, the residue was purified by column chromatography (dichloromethane:methanol=60:1) to give the product 4-methoxyphenol (46 mg, 74% yield).

$^1$H NMR (400 MHz, CDCl$_3$) δ 6.79-6.61 (m, 4H), 4.96 (br s, 1H), 3.69 (s, 3H); $^{13}$C NMR (100 MHz, CDCl$_3$) δ 55.9, 114.9, 116.1, 149.6, 153.7; ESI-MS: 125.1 (M+H)$^+$

Example 26 Synthesis of 4-methoxyphenol by Copper-Catalyzed Reaction of 4-chloroanisole The operation of this example was the same as that of Example 25 except that different oxalic diamide ligands were used. The results obtained are shown in the following table.

| Ligand | Yield/% | Ligand | Yield/% | Ligand | Yield/% |
|---|---|---|---|---|---|
| L-II-30 | 25 | L-II-34 | 19 | L-II-35 | 4 |
| L-II-58 | 21 | L-II-59 | 5 | L-II-60 | 6 |
| L-II-62 | 23 | L-II-64 | 27 | L-II-65 | 64 |
| L-II-91 | 2 | L-II-92 | 8 | L-II-93 | 74 |
| L-II-94 | 9 | L-II-95 | 2 | L-II-96 | 37 |
| L-II-97 | 41 | | | | |

Example 27 Synthesis of 4-methoxyphenol by Copper-Catalyzed Reaction of 4-chloroanisole The operation of this example was the same as that of Example 25. L-II-93 was chosen as the ligand, and different copper catalysts, bases, solvents were used. The results are shown in the following table.

| Entry | Copper salt | Base | Solvent/mL | Concentration/mol/L | Yield/% |
|---|---|---|---|---|---|
| 1 | Cu(acac)$_2$ | K$_3$PO$_4$ | DMSO/H$_2$O = 0.5/0.5 | 0.5 | 24 |
| 2 | Cu(acac)$_2$ | LiOH•H$_2$O | DMSO/H$_2$O = 0.5/0.5 | 0.5 | 32.5 |
| 3 | Cu(acac)$_2$ | LiOH•H$_2$O | DMSO/H$_2$O = 0.75/0.25 | 0.5 | 56 |
| 4 | Cu(acac)$_2$ | LiOH•H$_2$O | DMSO/H$_2$O = 0.8/0.2 | 0.5 | 75 |
| 5 | Cu(acac)$_2$ | LiOH•H$_2$O | DMSO/H$_2$O = 0.85/0.15 | 0.5 | 62 |
| 6 | Cu(acac)$_2$ | LiOH•H$_2$O | DMSO/H$_2$O = 0.9/0.1 | 0.5 | 58 |
| 7 | Cu(acac)$_2$ | LiOH•H$_2$O | DMSO/H$_2$O = 0.95/0.05 | 0.5 | 58 |
| 8 | Cu(acac)$_2$ | LiOH•H$_2$O | DMSO/H$_2$O = 1/0 | 0.5 | 0 |
| 9 | Cu$_2$S | LiOH•H$_2$O | DMSO/H$_2$O = 0.8/0.2 | 0.5 | 0 |
| 10 | Cu$_2$O | LiOH•H$_2$O | DMSO/H$_2$O = 0.8/0.2 | 0.5 | 75 |
| 11 | CuSCN | LiOH•H$_2$O | DMSO/H$_2$O = 0.8/0.2 | 0.5 | 16 |
| 12 | CuCN | LiOH•H$_2$O | DMSO/H$_2$O = 0.8/0.2 | 0.5 | 38 |
| 13 | CuBr | LiOH•H$_2$O | DMSO/H$_2$O = 0.8/0.2 | 0.5 | 71 |
| 14 | CuCl | LiOH•H$_2$O | DMSO/H$_2$O = 0.8/0.2 | 0.5 | 71 |
| 15 | CuI | LiOH•H$_2$O | DMSO/H$_2$O = 0.8/0.2 | 0.5 | 74 |
| 16 | Cu(OAc)$_2$ | LiOH•H$_2$O | DMSO/H$_2$O = 0.8/0.2 | 0.5 | 49 |
| 17 | CuO | LiOH•H$_2$O | DMSO/H$_2$O = 0.8/0.2 | 0.5 | 76 |
| 18 | CuCl$_2$ | LiOH•H$_2$O | DMSO/H$_2$O = 0.8/0.2 | 0.5 | 74 |
| 19 | CuBr$_2$ | LiOH•H$_2$O | DMSO/H$_2$O = 0.8/0.2 | 0.5 | 80 |
| 20 | CuTc | LiOH•H$_2$O | DMSO/H$_2$O = 0.8/0.2 | 0.5 | 73 |
| 21 | Cu(acac)$_2$ | LiOH•H$_2$O | DMSO/H$_2$O = 0.8/0.2 | 1 | 83 |
| 22 | Cu(acac)$_2$ | LiOH•H$_2$O | DMA/H$_2$O = 0.8/0.2 | 1 | 9 |
| 23 | Cu(acac)$_2$ | LiOH•H$_2$O | DMF/H$_2$O = 0.8/0.2 | 1 | 10 |
| 24 | Cu(acac)$_2$ | LiOH•H$_2$O | DMSO/t-BuOH/H$_2$O = 0.5/0.5/0.1 | 1 | 28 |
| 25 | Cu(acac)$_2$ | LiOH•H$_2$O | DMSO/H$_2$O = 0.8/0.2 | 1.5 | 80 |

Example 28 Synthesis of Substituted Phenol Via Copper-Catalyzed Reaction of Aryl

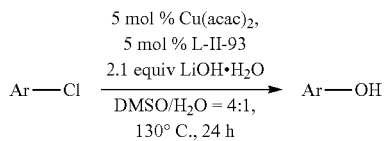

Copper acetylacetonate (Cu(acac)$_2$) (0.025 mmol), ligand L-II-93 (0.025 mmol) and lithium hydroxide monohydrate (1.05 mmol) were added into a 10 mL of Schlenk tube. The tube was then evacuated and backfilled with argon (three times), and then aryl chloride (0.5 mmol), 0.8 mL of DMSO and 0.2 mL of H$_2$ were added successively under argon. The reaction mixture was stirred well at 130° C. for 24 hours. After cooling, 2 mL of hydrochloric acid (1 mol/L), water and ethyl acetate were added and mixture was separated. The aqueous phase was extracted twice with ethyl acetate. The combined organic phase was dried over anhydrous sodium sulfate. After concentration, the residue was purified by column chromatography to give the product substituted phenol.

| Product and Yield | Characterization data of product |
|---|---|
| 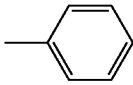<br>65% | $^1$H NMR (400 MHz, CDCl$_3$) δ 7.03 (d, J = 8.1 Hz, 2H), 6.73 (d, J = 8.4 Hz, 2H), 4.93 (br s, 1H), 2.27 (s, 3H); $^{13}$C NMR (100 MHz, CDCl$_3$) δ 20.5, 115.1, 130.0, 130.1, 153.3; ESI-MS: 109.1 (M + H)$^+$ |
| 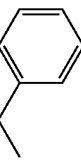<br>74% | $^1$H NMR (400 MHz, CDCl$_3$) δ 7.56-7.48 (m, 2H), 7.34 (t, J = 7.8 Hz, 1H), 7.10 (ddd, J = 8.1, 2.5, 0.9 Hz, 1H), 6.43 (br s, 1H), 2.60 (s, 3H); $^{13}$C NMR (100 MHz, CDCl$_3$) δ 26.8, 114.8, 121.0, 121.1, 130.0, 138.3, 156.5, 199.6; ESI-MS: 137.1 (M + H)$^+$ |
| 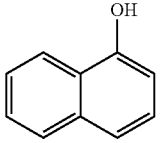<br>68% | $^1$H NMR (400 MHz, CDCl$_3$) δ 8.22-8.14 (m, 1H), 7.83-7.76 (m, 1H), 7.50-7.45 (m, 2H), 7.43 (d, J = 8.3 Hz, 1H), 7.29 (t, J = 7.8 Hz 1H), 6.79 (dd, J = 7.4, 0.6 Hz, 1H), 5.63 (br s, 1H); $^{13}$C NMR (100 MHz, CDCl$_3$) δ 108.7, 120.7, 121.6, 124.4, 125.3, 125.9, 126.5, 127.7, 134.8, 151.5; ESI-MS: 145.1 (M + H)$^+$ |
| <br>83% | $^1$H NMR (400 MHz, CDCl$_3$) δ 6.94-6.86 (m, 2H), 6.80-6.73 (m, 2H), 5.90 (br s, 1H); $^{13}$C NMR (100 MHz, CDCl$_3$) δ 157.38 (d, J = 36.4 Hz), 151.30 (d, J = 2.2 Hz), 116.35 (d, J = 8.1 Hz), 116.07 (d, J = 23.3 Hz); ESI-MS: 111.0 (M − H)$^-$ |

Example 28 Synthesis of Substituted Phenol Via Copper-Catalyzed Reaction of Aryl Iodide/Bromide

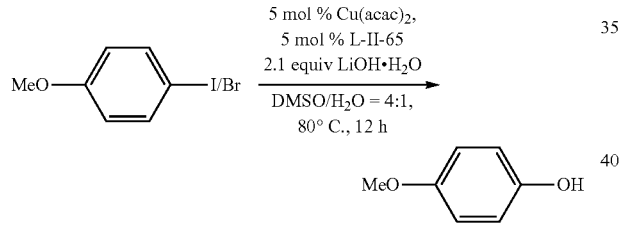

Copper acetylacetonate (Cu(acac)$_2$) (0.1 mmol), ligand L-II-65 (0.1 mmol) and lithium hydroxide monohydrate (4.2 mmol) were added into a 10 mL of Schlenk tube. The tube was evacuated and backfilled with argon (three times), and then 4-iodoanisole or 4-bromoanisole (2 mmol), 1.6 mL of DMSO and 0.4 ml of H$_2$O were added successively under argon. The reaction mixture was stirred well at 80° C. for 12 hours. After cooling, 6 mL of hydrochloric acid (1 mol/L), water and ethyl acetate were added and mixture was separated. The aqueous phase was extracted twice with ethyl acetate. The combined organic phase was dried over anhydrous sodium sulfate. After concentration, the residue was purified by column chromatography to give the product p-methoxy phenol (for 4-iodoanisole: yield 95%, for 4-bromoanisole: yield 93%).

Example 29 Coupling Reaction of 4-bromoanisole with Benzylamine

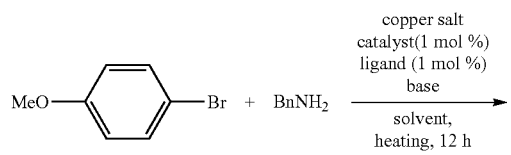

-continued

MeO—⟨⟩—NHBn

Copper catalyst (0.01 mmol), ligand (0.01 mmol) and base (1.5 mmol) were added into a 10 mL of Schlenk tube. The tube was evacuated and backfilled with argon (three times), and then 4-bromoanisole (1.0 mmol), benzylamine (1.5 mmol) and 1 mL of solvent were added. The reaction mixture was stirred well at 80° C. for 12 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography to give the product N-(4-methoxy)phenylbenzylamine.

The results obtained are shown in the following table.

| No. | Copper catalyst | Ligand | Base | Solvent | Temperature/° C. | Yield/% |
|---|---|---|---|---|---|---|
| 1 | CuI | L-II-94 | K$_3$PO$_4$ | DMSO | 80 | 45 |
| 2 | CuI | L-II-94 | KOH | DMSO | 80 | 76 |
| 3 | CuI | L-II-94 | NaOH | DMSO | 80 | 96 |
| 4 | CuI | L-II-94 | NaOAc | DMSO | 80 | 94 |

-continued

| No. | Copper catalyst | Ligand | Base | Solvent | Temperature/° C. | Yield/% |
|---|---|---|---|---|---|---|
| 5 | Cu₂O | L-II-93 | KOH | DMSO | 80 | 98 |
| 6 | Cu₂O | L-II-93 | NaOH | DMSO | 80 | 97 |
| 7 | Cu₂O | L-I-16 | KOH | tBuOH | 80 | 98 |
| 8* | Cu₂O | L-I-16 | NaOH | tBuOH | 70 | 94 |

*Reaction at 70° C. for 24 hours.

Example 30 Coupling Reaction of 4-bromoanisole with Other N-nucleophiles

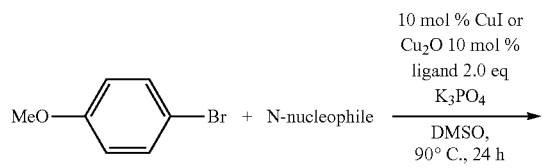

10 mol % CuI or Cu₂O 10 mol %
ligand 2.0 eq
K₃PO₄
DMSO, 90° C., 24 h

Copper catalyst (0.1 mmol), ligand (0.1 mmol) and potassium phosphate (2.0 mmol) were added into a 10 mL of Schlenk tube. The tube was evacuated and backfilled with argon (three times), and then aryl bromide (1.0 mmol), 1 mL of DMSO and coupling reagent (2.0 mmol) were added. The reaction mixture was stirred well at 90° C. for 24 hours. After cooling, water and ethyl acetate were added and mixture was separated. The aqueous phase was extracted twice with ethyl acetate. The combined organic phase was dried over anhydrous sodium sulfate. After concentration, the residue was purified by column chromatography to give the corresponding coupling products. The experimental results are as follows:

| N-nucleophiles | Copper catalyst | Ligand | Product and Yield |
|---|---|---|---|
| NH₃·H₂O | CuI | L-II-71 | MeO—C₆H₄—NH₂  89% |
| pyrrole | Cu₂O | L-II-82 | MeO—C₆H₄—N(pyrrolyl)  74% |
| imidazole | Cu₂O | L-II-82 | MeO—C₆H₄—N(imidazolyl)  83% |
| indole | Cu₂O | L-II-82 | MeO—C₆H₄—N(indolyl)  79% |
| PhC(O)NH₂ | Cu₂O | L-II-90 | MeO—C₆H₄—NHC(O)Ph  81% |

| N-nucleophiles | Copper catalyst | Ligand | Product and Yield |
|---|---|---|---|
| 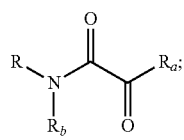 | Cu₂O | L-II-90 | 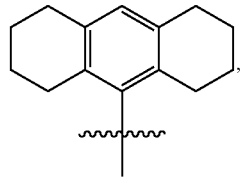 [SMILES: *c1c2c(cc3c1CCCC3)CCCC2]<br>84% |

All publications mentioned herein are incorporated by reference as if each individual document is cited as a reference in the present application. It should also be understood that, after reading the above contents of the present invention, those skilled in the art can make various changes or modifications, equivalents of which falls in the scope of claims as defined in the appended claims.

What we claim:

1. A method of a coupling reaction of an aryl halide, comprising performing the coupling reaction in the presence of copper as a catalyst, and a ligand of following of formula (I):

$$\underset{R_b}{\overset{R}{\underset{|}{N}}}\underset{O}{\overset{O}{\underset{\|}{C}}}\underset{O}{\overset{}{\underset{\|}{C}}}R_a$$ (I)

wherein R is selected from the group consisting of substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure;

$R_a$ is
(a) OR'; wherein R' is substituted or unsubstituted C1-C6 alkyl; or
(b) N(R")₂; wherein each R" is independently selected from the group consisting of H, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group is a monocyclic, polycyclic, spiro or bridged ring structure;

$R_b$ is selected from the group consisting of H, and C1-C6 alkyl;

or $R_b$ and R, together with adjacent nitrogen atom, form a substituted or unsubstituted 3- to 20-membered heteroaryl, or substituted or unsubstituted 3- to 20-membered heterocyclic group;

the term substituted means that one or more hydrogen atoms on the group is substituted by a substituent selected from the group consisting of halogen, C1-C6 alkyl, halogenated C1-C6 alkyl, C1-C6 alkoxy, C6-C10 aryl, C6-C10 aryl-oxy, C2-C10 ester group (alkyl-COO—), C2-C10 acyl-alkoxy (alkyl-OOC—), C2-C10 acyl (alkyl-CO—), C2-C10 acyl amino (alkyl/aryl-NHC(O)—), —COOH, nitro, cyano, hydroxy, amino, and amino substituted by one or two C1-C6 alkyl; and wherein the aryl halide is selected from the group consisting of aryl chloride, aryl bromide, aryl iodide, and a combination thereof.

2. The method of claim 1, wherein R is selected from the group consisting of substituted or unsubstituted phenyl, substituted or unsubstituted naphthyl, substituted or unsubstituted benzyl, substituted or unsubstituted quinolinyl, substituted or unsubstituted

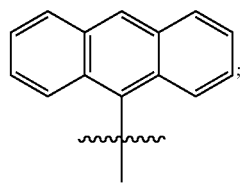 [SMILES: *c1c2ccccc2cc2ccccc12]

substituted or unsubstituted adamantyl, substituted or unsubstituted C1-C6 alkyl, and substituted or unsubstituted

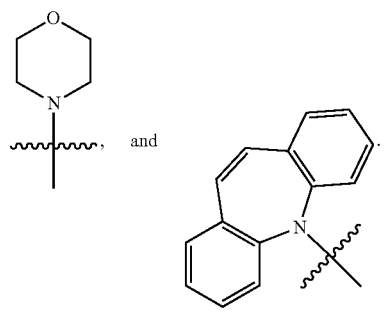 [SMILES: *N1CCOCC1 ; *N1c2ccccc2C=Cc2ccccc21]

or R and $R_b$, together with adjacent nitrogen atom, form a substituted or unsubstituted group selected from the group consisting of 3. The method of claim 1, wherein R is selected from the group consisting of substituted or unsubstituted phenyl, substituted or unsubstituted naphthyl, substituted or unsubstituted benzyl, C1-C4alkyl, pyridyl, and adamantyl;

$R_a$ is
(a) OR'; wherein R' is selected from the group consisting of substituted or unsubstituted C1-C6 alkyl; or
(b) N(R")$_2$; wherein each R" is independently selected from the group consisting of H, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure.

4. The method of claim 1, wherein, in the coupling reaction, the molar ratio of the ligand to the aryl halide is 1-50:100; and/or the molar ratio of the ligand to the copper catalyst is 1-5:1.

5. The method of claim 1, wherein the coupling reaction is characterized as:

in which

is reacted with a coupling reagent in an inert solvent to produce a compound of

wherein X is selected from the group consisting of N, O, and S;

Y is selected from the group consisting of Cl, Br, and I;

is selected from the group consisting of substituted or unsubstituted C6-C20 aryl, and substituted or unsubstituted 3- to 20-membered heteroaryl; wherein the substitution means that one or more hydrogen atoms on the aryl is substituted by a substituent selected from the group consisting of halogen, nitro, cyano, amino unsubstituted or substituted by one or two C1-C6 alkyl or C2-C10 acyl (alkyl-CO—), hydroxy, unsubstituted or halogenated C1-C6 alkyl, C1-C6 alkoxy, C6-C10 aryl, 3- to 20-membered heteroaryl, C6-C10 aryl-oxy, C2-C10 ester group (alkyl-COO—), C2-C10 acyl (alkyl-CO—), C2-C10 acyl-alkoxy (alkyl-OOC—), C2-C10 acylamino (alkyl-NHC(O)—, aryl-NHC(O)—), —COOH, hydroxy-C1-C10 alkylene, MeS—, sulfuryl, and sulfonamido; wherein two hydrogen atoms on two adjacent carbon atoms of the aryl is substituted by —(CH$_2$)$_n$— (n is 1, 2, 3, 4, 5 or 6);

the coupling reagent is selected from the group consisting of ammonium hydroxide, ammonia, ammonium salts (preferably ammonium chloride, ammonium carbonate, ammonium sulfate, ammonium hydrogenphosphate, or the combinations thereof)/hydroxide solution (preferably potassium hydroxide solution), C$^{}$ (having 2 to 19 carbon atoms and may be a saturated, partially unsaturated or aromatic ring), R$_c$C(O)NHR$_2$, R$_1$SO$_2$M (preferably, M is sodium, potassium), sodium azide, NHR$_1$R$_2$, R$_1$OH, R$_1$SH, and hydroxide (preferably lithium hydroxide, or a mixture of potassium phosphate, potassium carbonate, cesium carbonate and water);

each of R$_1$, R$_2$, and R$_c$ is independently selected from the group consisting of H, substituted or unsubstituted C1-C6 alkyl, substituted or unsubstituted C1-C6 alkenyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, substituted or unsubstituted C1-C5 alkyl-C3-C20 cycloalkyl, substituted or unsubstituted 3- to 20-membered heterocyclic group, and substituted or unsubstituted C1-C5 alkyl-3- to 20-membered heterocyclic group;

or R$_1$ and R$_2$, together with adjacent nitrogen atom, form a substituted or unsubstituted 3- to 20-membered heterocyclic group, or substituted or unsubstituted 3- to 20-membered heteroaryl;

or R$_c$ and R$_2$, together with adjacent C(O)NH, form a substituted or unsubstituted 3- to 20-membered heterocyclic group, or substituted or unsubstituted 3- to 20-membered heteroaryl;

wherein the heteroaryl or heterocyclic group has 1 to 5 heteroatoms selected from the group consisting of N, O, and S; the cycloalkyl or heterocyclic group may be a monocyclic, polycyclic, spiro or bridged ring structure;

the term substituted means that one or more hydrogen atoms on the group is substituted by a substituent selected from the group consisting of halogen, cyano, oxo (i.e. two hydrogen atoms on the same carbon atom of the group are substituted by =O), C1-C6 alkyl, halogenated C1-C6 alkyl, C1-C6 alkoxy, C6-C10 aryl, C6-C10 aryl-oxy, C2-C10 ester group (alkyl-COO—), C2-C10 acyl-alkoxy (alkyl-OOC—), C2-C10 acyl (alkyl-CO—), C2-C10 acylamino (alkyl/aryl-NHC(O)—), —COOH, nitro, hydroxy, amino, amino substituted by one or two C1-C6 alkyl, and C1-C6 alkyl-S—.

6. The method of claim 1, wherein the coupling reaction is performed at a temperature of 50-180° C.

7. The method of claim 1 wherein the coupling reaction includes a following reaction (1), (2), (3), (4), (5), (6), (7) or (8):

(1) carrying out a reaction of

with NHR$_1$R$_2$ in an inert solvent to produce

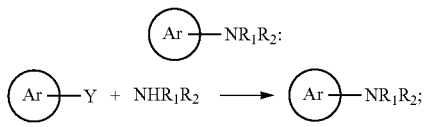

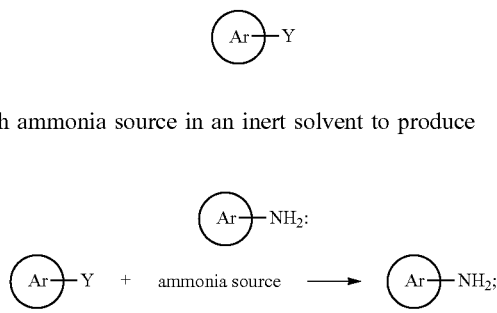

(2) carrying out a reaction of

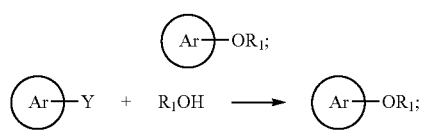

with ammonia source in an inert solvent to produce

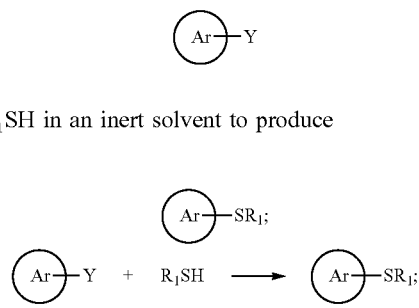

and
wherein the ammonia source is selected from the group consisting of ammonia, ammonium hydroxide, ammonium chloride, ammonium carbonate, ammonium bicarbonate, ammonium sulfate, ammonium nitrate, ammonium phosphate, diammonium hydrogen phosphate, sodium azide, preferably ammonia, ammonium hydroxide, ammonium chloride and diammonium hydrogen phosphate;

(3) carrying out a reaction of (Ar)—Y with R$_1$OH in an inert solvent to produce (Ar)—OR$_1$;

(Ar)—Y + R$_1$OH ⟶ (Ar)—OR$_1$;

(4) carrying out a reaction of (Ar)—Y with R$_1$SH in an inert solvent to produce (Ar)—SR$_1$;

(Ar)—Y + R$_1$SH ⟶ (Ar)—SR$_1$;

(5) carrying out a reaction of

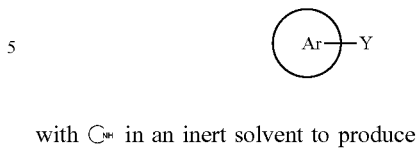

with ◯$^{NH}$ in an inert solvent to produce

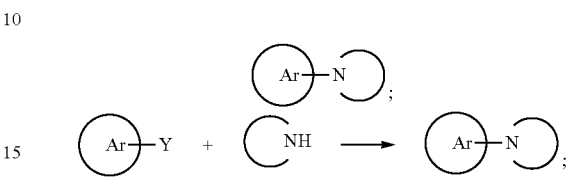

wherein ◯$^{NH}$ is a substituted or unsubstituted 3- to 20-membered ring containing N atom, and the 3- to 20-membered ring is saturated, unsaturated or aromatic;

(6) carrying out a reaction of (Ar)—Y with

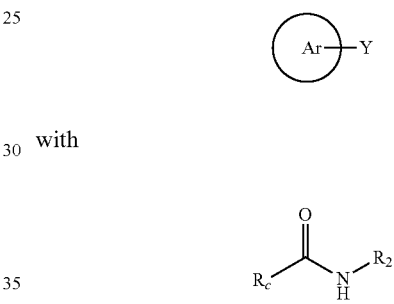

in an inert solvent to produce

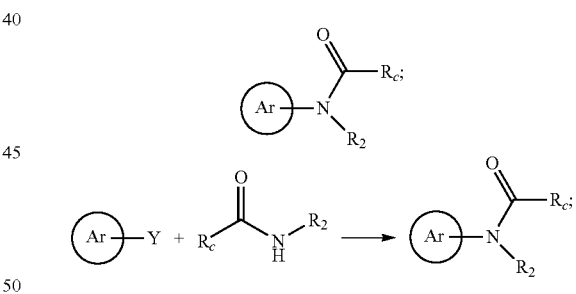

wherein R$_c$ is selected from the group consisting of H, substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group is a monocyclic, polycyclic, spiro or bridged ring structure; or R$_c$ and R$_2$, together with adjacent C(O)NH, form a substituted or unsubstituted 3- to 20-membered heterocyclic group, or substituted or unsubstituted 3- to 20-membered heteroaryl;

the term substituted means that one or more hydrogen atoms on the group is substituted by a substituent selected from the group consisting of halogen, C1-C6 alkyl, C1-C6 alkoxy, C6-C10 aryl, C6-C10 aryl-oxy, C2-C10 ester group (alkyl-COO—), C2-C10 acyl (alkyl-CO—), C2-C10 acyl amino (alkyl-NHC(O)—, aryl-NHC(O)—), and —COOH;

(7) carrying out a reaction of

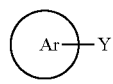

with $R_1SO_2M$ in an inert solvent to produce

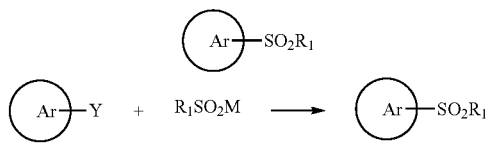

wherein the definition of each group is described as above;

(8) carrying out a reaction of

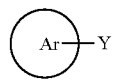

with hydroxide or OH⁻ hydrolyzed from a base in an inert solvent to produce

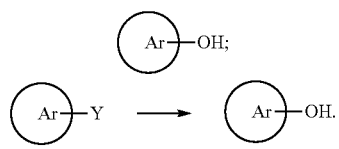

8. The method of claim 4, wherein the molar ratio of the ligand to the aryl halide is 5-20:100.

9. The method of claim 4, wherein the molar ratio of the ligand to the copper catalyst is 1-2:1.

10. The method of claim 6, wherein the coupling reaction is carried out at a temperature ranging from 100-130° C.

11. The method of claim 7, wherein the reaction (1), (2), (3), (4), (5), (6), (7) or (8) is carried out at a temperature ranging from 100-130° C.

12. A catalyst system for an aryl coupling reaction, which comprises: a copper catalyst, a ligand, a base, and an organic solvent;
wherein the copper catalyst is selected from the group consisting of CuI, CuBr, CuCl, CuTc, Cu(OAc)$_2$, CuSO$_4$, Cu$_2$O, CuBr$_2$, CuCl$_2$, CuO, CuSCN, CuCN, Cu(acac)$_2$, and the combinations thereof; and preferably is CuI, Cu$_2$O, or Cu(acac)$_2$;
the base is selected from the group consisting of potassium carbonate, cesium carbonate, potassium phosphate, sodium bicarbonate, potassium bicarbonate, sodium carbonate, lithium hydroxide, sodium hydroxide, tetrabutyl ammonium hydroxide, and/or a hydrate of the base, and the combinations thereof; and preferably is potassium phosphate, cesium carbonate, orlithium hydroxide;
the solvent is selected from the group consisting of DMSO, DMF, DMA, NMP, acetonitrile, isopropanol, 1,4-dioxane, tetrahydrofuran, toluene, tert-butanol, and the combinations thereof; and preferably is DMSO and/or DMF and/or DMSO/H$_2$O;
the ligand is of formula (I):

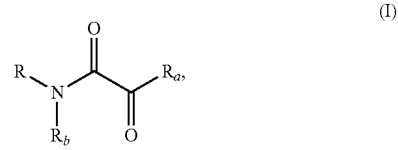

wherein R is selected from the group consisting of substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure;

$R_a$ is selected from (a) or (b):

(a) OR'; wherein R' is selected from the group consisting of substituted or unsubstituted C1-C6 alkyl; or (b) N(R")$_2$; wherein each R" is independently selected from the group consisting of H, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S; the cycloalkyl or heterocyclic group may be a monocyclic, polycyclic, spiro or bridged ring structure (preferably, N(R")$_2$ is NHR");

$R_b$ is selected from the group consisting of H, and C1-C6 alkyl;

or $R_b$ and R, together with adjacent nitrogen atom, form a substituted or unsubstituted 3- to 20-membered heteroaryl, or substituted or unsubstituted 3- to 20-membered heterocyclic group;

the term substituted means that one or more hydrogen atoms on the group is substituted by a substituent selected from the group consisting of halogen, C1-C6 alkyl, halogenated C1-C6 alkyl, C1-C6 alkoxy, C6-C10 aryl, C6-C10 aryl-oxy, C2-C10 ester group (alkyl-COO—), C2-C10 acyl-alkoxy (alkyl-OOC—), C2-C10 acyl (alkyl-CO—), C2-C10 acyl amino (alkyl/aryl-NHC(O)—), —COOH, nitro, hydroxy, amino, and amino substituted by one or two C1-C6 alkyl.

13. A process for preparation of a compound of formula (I):

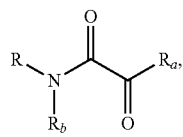
(I)

wherein R is selected from the group consisting of substituted or unsubstituted C1-C6 alkyl, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S: the cycloalkyl or heterocyclic group may be is a monocyclic, polycyclic, spiro or bridged ring structure;

$R_a$ is (a) OR'; wherein R' is selected from the group consisting of Me and Et; or (b) N(R")$_2$; wherein each R" is independently selected from the group consisting of H, substituted or unsubstituted C6-C20 aryl, substituted or unsubstituted 3- to 20-membered heteroaryl, substituted or unsubstituted C7-C25 alkyl-aryl, substituted or unsubstituted C1-C5 alkyl-3- to 20-membered heteroaryl, substituted or unsubstituted C3-C20 cycloalkyl, and substituted or unsubstituted 3- to 20-membered heterocyclic group; wherein the heteroaryl or heterocyclic group has 1 to 5 heteroatoms selected from the group consisting of N, O and S: the cycloalkyl or heterocyclic group is a monocyclic, polycyclic, spiro or bridged ring structure;

$R_b$ is selected from the group consisting of H, and C1-C6 alkyl;

or $R_b$ and R, together with adjacent nitrogen atom, form a substituted or unsubstituted 3- to 20-membered heteroaryl, or substituted or unsubstituted 3- to 20-membered heterocyclic group;

and when $R_a$ is selected from (a) and R' is H, R is naphthyl substituted by methyl;

the term substituted means that one or more hydrogen atoms on the group is substituted by a substituent selected from the group consisting of halogen, C1-C6 alkyl, halogenated C1-C6 alkyl, C1-C6 alkoxy, C6-C10 aryl, C6-C10 aryl-oxy, C2-C10 ester group (alkyl-COO—), C2-C10 acyl-alkoxy (alkyl-OOC—), C2-C10 acyl (alkyl-CO—), C2-C10 acyl amino (alkyl/aryl-NHC(O)—), —COOH, nitro, cyano, hydroxy, amino, and amino substituted by one or two C1-C6 alkyl;

wherein the process is carried out by a method selected from the group consisting of process (i), process (ii) and process (II); wherein:

process (i) comprises a step of:

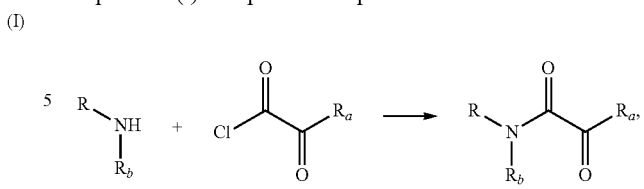

in which
R—NH—$R_b$ is reacted with

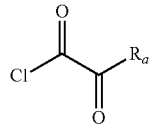

in an inert solvent to produce the compound of formula (I); process (ii) comprises a step of:

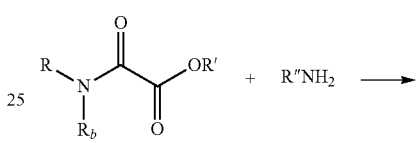

in which
R"—NH$_2$ is reacted with

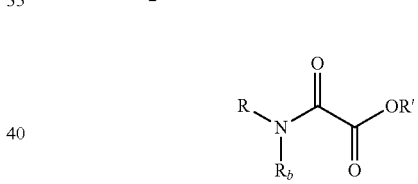

in an inert solvent to produce the compound of formula (I); and
process (II) comprises a step of:

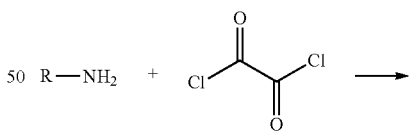

in which
R—NH$_2$ is reacted with oxalyl chloride in an inert solvent to produce the compound of formula (I).

* * * * *